United States Patent
Kawai

(10) Patent No.: US 9,751,942 B2
(45) Date of Patent: Sep. 5, 2017

(54) ANTI-LAMP5 ANTIBODY AND UTILIZATION THEREOF

(71) Applicant: CHUGAI SEIYAKU KABUSHIKI KAISHA, Kita-ku, Tokyo (JP)

(72) Inventor: Shigeto Kawai, Meguro-ku (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/388,649

(22) PCT Filed: Mar. 29, 2013

(86) PCT No.: PCT/JP2013/059516
§ 371 (c)(1),
(2) Date: Jan. 12, 2015

(87) PCT Pub. No.: WO2013/147153
PCT Pub. Date: Oct. 3, 2013

(65) Prior Publication Data
US 2015/0118184 A1    Apr. 30, 2015

(30) Foreign Application Priority Data
Mar. 29, 2012 (JP) ................................. 2012-076735

(51) Int. Cl.
| | | |
|---|---|---|
| *C07K 16/28* | (2006.01) |
| *A61K 39/395* | (2006.01) |
| *C07K 14/54* | (2006.01) |
| *A61K 38/20* | (2006.01) |
| *A61P 35/00* | (2006.01) |
| *C07K 14/705* | (2006.01) |
| *A61K 47/48* | (2006.01) |

(52) U.S. Cl.
CPC ............ *C07K 16/28* (2013.01); *A61K 38/204* (2013.01); *A61K 39/3955* (2013.01); *A61K 47/48561* (2013.01); *C07K 14/5412* (2013.01); *C07K 14/70596* (2013.01); *C07K 16/2896* (2013.01); *C07K 2317/56* (2013.01); *C07K 2317/565* (2013.01); *C07K 2317/732* (2013.01); *C07K 2317/76* (2013.01); *C07K 2317/77* (2013.01); *C07K 2319/00* (2013.01); *C07K 2319/42* (2013.01)

(58) Field of Classification Search
None
See application file for complete search history.

(56) References Cited

U.S. PATENT DOCUMENTS

2012/0128678 A1    5/2012   Aburatani et al.
2012/0328624 A1   12/2012   Yoshida et al.

FOREIGN PATENT DOCUMENTS

| EP | 1932854 A1 | 6/2008 |
| JP | 5-506574 A | 9/1993 |
| JP | 2008-162954 A | 7/2008 |
| WO | 9114438 | 10/1991 |
| WO | 2005/001092 A2 | 1/2005 |
| WO | 2010119691 A1 | 10/2010 |
| WO | 2011093097 A1 | 8/2011 |

OTHER PUBLICATIONS

Data Sheet for mAb 32.4 from eBioscience, no author indicated, available at http://www.ebioscience.com/human-lamp5-antibody-purified-342.htm; 1 page as printed; no date available.*
Journal of Immunology. 2007, 179: 2815-2823.*
Axel Defays et al., BAD-LAMP is a novel biomarker of nonactivated human plasmacytoid dendritic cells, Blood, Jul. 21, 2011, pp. 609-617, vol. 118, No. 3.
International Search Report of PCT/JP2013/059516, Jul. 2, 2013, Japan Patent Office.
Alexandre David et al, BAD-LAMP defines a subset of early endocytic organelles in subpopulations of cortical projection neurons, Journal of Cell Science, 2007, pp. 353-365, vol. 120.
Fabio Facchetti et al., The plasmacytoid monocyte/interferon producing cells, Virchows Arch, Oct. 28, 2003, pp. 703-717, vol. 443.
Teresa Marafioti et al, Novel markers of normal and neoplastic human plasmacytoid dendritic cells, Blood, Jan. 24, 2008, pp. 3778-3792.
Walter Hunziker et al, Intracellular trafficking of lycocomal membrane proteins, BioEssays, 1995, pp. 379-389, vol. 18, No. 5.
Minoru Fukuda, "Lysosomal Membrane Glycoproteins Structure, Biosynthesis, and Intracellular Trafficking", The Journal of Biological Chemistry, Nov. 15, 1991, pp. 21327-21330, vol. 266, No. 32.
Victoria Sarafian et al, Expression of Lamp-1 and Lamp-2 and Their Interactions With Galectin-3 in Human Tumor Cells, International of Journal of Cancer, 1998, pp. 105-111, vol. 75.
Communication dated Oct. 7, 2015 from the European Patent Office in counterpart application No. 13767407.3.
Extended European Search Report dated Jan. 7, 2016, issued by the European Patent Office in corresponding European Application No. 13767407.3.

* cited by examiner

Primary Examiner — Zachary Howard
(74) *Attorney, Agent, or Firm* — Sughrue Mion, PLLC

(57) ABSTRACT

A monoclonal antibody recognizing the extracellular region of LAMP5 was produced. The produced antibody demonstrated antibody-dependent cell-mediated cytotoxic activity, and/or cell growth inhibitory activity in the presence of a toxin-labeled secondary antibody, against a multiple myeloma cell line.

10 Claims, 9 Drawing Sheets

ANTI-LAMP5 ANTIBODY AND UTILIZATION THEREOF

CROSS REFERENCE TO RELATED APPLICATIONS

This application is a National Stage of International Application No. PCT/JP2013/059516 filed Mar. 29, 2013, claiming priority based on Japanese Patent Application No. 2012-076732 filed Mar. 29, 2012, the contents of all of which are incorporated herein by reference in their entirety.

TECHNICAL FIELD

The present invention relates to an anti-LAMP5 antibody, a method for, for example, the treatment of cancer that utilizes that antibody, and a growth inhibitor of cancer cells (and particularly an anticancer drug) having that antibody as an active ingredient thereof.

BACKGROUND ART

Cancer is one of the leading causes of death in advanced countries. Numerous chemotherapeutic agents have been developed in the past 50 years for the purpose of treating cancer. The majority of chemotherapeutic agents are classified into alkylating agents, metabolic antagonists, anthracyclines, plant alkaloids, topoisomerase inhibitors or antitumor agents. All of these pharmaceutical agents exert therapeutic effects through a mechanism that functions in some form by having an effect on cell division or DNA synthesis.

The efficacy of a specific chemotherapeutic agent varies according to the type of cancer, the patient and the elapsed time in an individual patient. Cancer cells that have been exposed to a chemotherapeutic agent may develop tolerance to that chemotherapeutic agent and frequently similarly develop cross-tolerance to a plurality of other chemotherapeutic agents as well. Moreover, depending on the mechanism of these chemotherapeutic agents, there are many cases in which the dosage or usage of a chemotherapeutic agent is restricted in order to control adverse side effects brought about as a result of cell damage to normal cells caused by these chemotherapeutic agents.

Development has been proceeded in recent years on molecular target drugs that target molecules specifically expressed in cancer cells as an alternative to conventional chemotherapeutic agents. The appearance of these molecular target drugs has enabled to treat cancer and thus contributes to patient QOL by avoiding the characteristic adverse side effects of conventional chemotherapeutic agents. These molecular target drugs include small molecule pharmaceutical agents as well as large molecule pharmaceutical agents such as antibodies. Although therapeutic antibodies target molecules expressed on the cell surface, in addition to offering the advantage of low toxicity since antibody molecules per se are molecules that are intrinsically present in the body, therapeutic antibodies also offer the advantage of demonstrating therapeutic effects by specifically damaging target cells by a mechanism of action other than that of a small molecule therapeutic agent, such as cytotoxicity mediated by an effector function, and numerous therapeutic antibodies have been commercially marketed in recent years.

LAMP5 (also known as BAD-LAMP, C20orf103, UNC-43 or NCBI reference sequence: NM 012261 and NM 001199897) is a type I transmembrane protein that was discovered by the group of Philippe Pierre et al. to be a lysosome-associated membrane protein-like (LAMP-like) protein expressed in mouse brain ([NPL 1]). The same group later reported that LAMP5 is also expressed in plasmacytoid dendritic cells (pDCs) in humans (NPL 2). pDCs are cells that are involved in natural immunity, and rapidly produce type I interferons after having detected a viral infection (NPL 3). In addition, although pDCs are mainly present in lymph nodes, small amounts have also been detected in peripheral blood. Although a cell surface marker for detecting pDCs is required to efficiently analyze pDCs present in peripheral blood, there are few specific markers available (NPL 4).

LAMP5 has an intracellular sorting signal sequence on the C-terminal thereof, and is localized in intracellular granules designated as endoplasmic reticulum-Golgi intermediate compartments (ERGIC) within pDCs (NPL 2). On the other hand, LAMP-like proteins are typically localized in lysosomes and endosomes and some of those are also expressed on the cell membrane (NPLs 5 and 6). LAMP1 and LAMP2 have been shown to be expressed on the cell membrane in cancer cell lines in analyses using FACS (NPL 7). However, it is not known as to whether or not LAMP5 is expressed on the cell surface in a state that enables it to be targeted by a molecular target drug.

CITATION LIST

Non Patent Literature

[NPL 1]: BAD-LAMP defines a subset of early endocytic organelles in subpopulations of cortical projection neurons, J. Cell Sci. (2007) 120: 353-65
[NPL 2]: BAD-LAMP is a novel biomarker of nonactivated human plasmacytoid dendritic cells, Blood (2011) 118: 609-17
[NPL 3]: The plasmacytoid monocyte/interferon producing cells, Virchows Arch. (2003) 443: 703-17
[NPL 4]: Novel markers of normal and neoplastic human plasmacytoid dendritic cells, Blood (2008) 111: 3778-92
[NPL 5]: Intracellular trafficking of lysosomal membrane proteins, Bioassays (1996) 18: 379-89
[NPL 6]: Lysosomal membrane glycoproteins: structure, biosynthesis and intracellular trafficking, J. Biol. Chem. (1991) 266: 21327-30
[NPL 7]: Expression of Lamp-1 and Lamp-2 and their interactions with galectin-3 in human tumor cells, Int. J. Cancer (1998) 75: 105-11

SUMMARY OF INVENTION

Technical Problem

With the foregoing in view, an object of the present invention is to provide a monoclonal antibody which binds to LAMP5 expressed on the surface of cells. In addition, an object of the present invention is to provide an anti-LAMP5 antibody having cytotoxic activity against cells that express LAMP5. Moreover, an object of the present invention is to provide an anti-LAMP5 antibody that has internalization activity. Moreover, an object of the present invention is to provide an anti-LAMP5 antibody having internalization activity linked to a cytotoxic substance. Moreover, an object of the present invention is to provide a pharmaceutical composition (and particularly an anticancer drug) that comprises the above-mentioned anti-LAMP5 antibody. Moreover, an object of the present invention is to provide a pharmaceutical composition (and particularly, an anticancer drug) comprising the above-mentioned anti-LAMP5 antibody that is combined with IL-6. Moreover, an object of the present invention is to provide a method for producing the above-mentioned anti-LAMP5 antibody.

Solution to Problem

As a result of conducting extensive studies to solve the above-mentioned problems, the inventor of the present invention found that LAMP5 is expressed in multiple myeloma by microarray analysis. Next, in order to verify whether or not LAMP5 is expressed on the cell membrane, the inventor of the present invention produced a monoclonal antibody that recognizes the extracellular region of LAMP5 and is able to be used in FACS. As a result of examining the expression of LAMP5 in multiple myeloma cell lines using the resulting anti-LAMP5 antibody, LAMP5 was confirmed to be expressed on the cell membrane. Anti-LAMP5 antibody exhibited antibody-dependent cell-mediated cytotoxicity (ADCC) and cell growth inhibitory activity in the presence of toxin-labeled secondary antibody against multiple myeloma cell lines. In addition, cell growth inhibitory activity of anti-LAMP5 antibody was enhanced in the presence of IL-6. On the basis of these results, the inventor of the present invention found that anti-LAMP5 antibody is useful in treatment such as treatment of multiple myeloma, thereby leading to completion of the present invention. More specifically, the present invention relates to that illustrated below.

[1] A monoclonal antibody which binds to an epitope present from position 39 to position 289 of a polypeptide defined in SEQ ID NO: 8 expressed on a cell surface.

[2] The monoclonal antibody according to [1], which binds to an epitope present from position 30 to position 235 of a polypeptide defined in SEQ ID NO: 65 expressed on a cell surface.

[3] The monoclonal antibody according to [1], which has internalization activity.

[4] The monoclonal antibody according to [3], which is linked to a cytotoxic substance.

[5] The monoclonal antibody according to any of [1] to [4], which has cytotoxic activity.

[6] The monoclonal antibody according to [5], wherein the cytotoxic activity is antibody-dependent cell-mediated cytotoxicity (ADCC).

[7] A monoclonal antibody selected from a group consisting of the following (1) to (11):

(1) an antibody comprising a heavy chain variable region comprising the CDR1 defined by SEQ ID NO: 35, the CDR2 defined by SEQ ID NO: 36 and the CDR3 defined by SEQ ID NO: 37, and a light chain variable region comprising the CDR1 defined by SEQ ID NO: 38, the CDR2 defined by SEQ ID NO: 39 and the CDR3 defined by SEQ ID NO: 40;

(2) an antibody comprising a heavy chain variable region comprising the CDR1 defined by SEQ ID NO: 41, the CDR2 defined by SEQ ID NO: 42 and the CDR3 defined by SEQ ID NO: 43, and a light chain variable region comprising the CDR1 defined by SEQ ID NO: 44, the CDR2 defined by SEQ ID NO: 45 and the CDR3 defined by SEQ ID NO: 46;

(3) an antibody comprising a heavy chain variable region comprising the CDR1 defined by SEQ ID NO: 47, the CDR2 defined by SEQ ID NO: 48 and the CDR3 defined by SEQ ID NO: 49, and a light chain variable region comprising the CDR1 defined by SEQ ID NO: 50, the CDR2 defined by SEQ ID NO: 51 and the CDR3 defined by SEQ ID NO: 52;

(4) an antibody comprising a heavy chain variable region comprising the CDR1 defined by SEQ ID NO: 53, the CDR2 defined by SEQ ID NO: 54 and the CDR3 defined by SEQ ID NO: 55, and a light chain variable region comprising the CDR1 defined by SEQ ID NO: 56, the CDR2 defined by SEQ ID NO: 57 and the CDR3 defined by SEQ ID NO: 58;

(5) the monoclonal antibody according to any of (1) to (4), comprising a heavy chain comprising a heavy chain constant region of human IgG and/or a light chain comprising a light chain constant region of human antibody;

(6) the monoclonal antibody according to (5), wherein the heavy chain comprising a heavy chain constant region of human IgG is a heavy chain comprising the heavy chain constant region defined by SEQ ID NO: 68;

(7) the monoclonal antibody according to (5) or (6), wherein the light chain comprising a light chain constant region of human antibody is a light chain comprising the light chain constant region defined by SEQ ID NO: 73;

(8) a monoclonal antibody in which one or more amino acids are substituted, deleted, added and/or inserted in the antibody according to any of (1) to (7) and which has binding activity equivalent to that of the monoclonal antibody according to any of (1) to (7) with respect to an epitope present at position 39 to position 289 of the polypeptide defined in SEQ ID NO: 8 expressed on a cell surface;

(9) the monoclonal antibody according to (5) or (7), wherein the heavy chain comprising a heavy chain constant region of human IgG is a heavy chain that comprises at least one substitution of an amino acid selected from the group of amino acids at position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440, as defined by the EU numbering system, in the heavy chain constant region of SEQ ID NO: 68;

(10) a monoclonal antibody which binds to the same epitope as the epitope bound by the antibody according to any of (1) to (9); or,

(11) a monoclonal antibody that competes with the antibody according to any of (1) to (9) for binding to an epitope present from position 39 to position 289 of the polypeptide defined in SEQ ID NO: 8 expressed on a cell surface.

[8] A vector selected from a group consisting of the following (1) to (8):

(1) a vector comprising a polynucleotide encoding a heavy chain variable region selected from a group consisting of the following (a) to (d):

(a) a heavy chain variable region comprising the CDR1 defined by SEQ ID NO: 35, the CDR2 defined by SEQ ID NO: 36 and the CDR3 defined by SEQ ID NO: 37;

(b) a heavy chain variable region comprising the CDR1 defined by SEQ ID NO: 41, the CDR2 defined by SEQ ID NO: 42 and the CDR3 defined by SEQ ID NO: 43;

(c) a heavy chain variable region comprising the CDR1 defined by SEQ ID NO: 47, the CDR2 defined by SEQ ID NO: 48 and the CDR3 defined by SEQ ID NO: 49; or, (d) a heavy chain variable region comprising the CDR1 defined by SEQ ID NO: 53, the CDR2 defined by SEQ ID NO: 54 and the CDR3 defined by SEQ ID NO: 55;

(2) a vector comprising a polynucleotide encoding the heavy chain variable region according to any of (a) to (d) of (1) above and the heavy chain constant region of SEQ ID NO: 68;

(3) a vector comprising a variant nucleotide encoding at least one substitution of an amino acid selected from the group of amino acids at position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440, as defined by the EU numbering system, in a polynucleotide encoding the heavy chain variable region according to any of (a) to (d) of (1) above and the heavy chain constant region of SEQ ID NO: 68;

(4) a vector comprising a polynucleotide encoding a light chain variable region selected from a group consisting of the following (e) to (h):

(e) a light chain variable region comprising the CDR1 defined by SEQ ID NO: 38, the CDR2 defined by SEQ ID NO: 39 and the CDR3 defined by SEQ ID NO: 40;

(f) a light chain variable region comprising the CDR1 defined by SEQ ID NO: 44, the CDR2 defined by SEQ ID NO: 45 and the CDR3 defined by SEQ ID NO: 46;

(g) a light chain variable region comprising the CDR1 defined by SEQ ID NO: 50, the CDR2 defined by SEQ ID NO: 51 and the CDR3 defined by SEQ ID NO: 52; or, (h) a light chain variable region comprising the CDR1 defined by SEQ ID NO: 56, the CDR2 defined by SEQ ID NO: 57 and the CDR3 defined by SEQ ID NO: 58;

(5) a vector comprising a polynucleotide encoding the light chain variable region according to any of (e) to (h) of (4) above and the light chain constant region of SEQ ID NO: 73;

(6) a vector comprising a polynucleotide encoding the heavy chain variable region and light chain variable region selected from a group consisting of the following (i) to (l):

(i) a heavy chain variable region comprising the CDR1 defined by SEQ ID NO: 35, the CDR2 defined by SEQ ID NO: 36 and the CDR3 defined by SEQ ID NO: 37, and a light chain variable region comprising the CDR1 defined by SEQ ID NO: 38, the CDR2 defined by SEQ ID NO: 39 and the CDR3 defined by SEQ ID NO: 40;

(j) a heavy chain variable region comprising the CDR1 defined by SEQ ID NO: 41, the CDR2 defined by SEQ ID NO: 42 and the CDR3 defined by SEQ ID NO: 43, and a light chain variable region comprising the CDR1 defined by SEQ ID NO: 44, the CDR2 defined by SEQ ID NO: 45 and the CDR3 defined by SEQ ID NO: 46;

(k) a heavy chain variable region comprising the CDR1 defined by SEQ ID NO: 47, the CDR2 defined by SEQ ID NO: 48 and the CDR3 defined by SEQ ID NO: 49, and a light chain variable region comprising the CDR1 defined by SEQ ID NO: 50, the CDR2 defined by SEQ ID NO: 51 and the CDR3 defined by SEQ ID NO: 52; or, (l) a heavy chain variable region comprising the CDR1 defined by SEQ ID NO: 53, the CDR2 defined by SEQ ID NO: 54 and the CDR3 defined by SEQ ID NO: 55, and a light chain variable region comprising the CDR1 defined by SEQ ID NO: 56, the CDR2 defined by SEQ ID NO: 57 and the CDR3 defined by SEQ ID NO: 58;

(7) a vector comprising a polynucleotide encoding the heavy chain variable region and light chain variable region according to any of (i) to (l) of (6) above, and a polynucleotide encoding the light chain constant region of SEQ ID NO: 73, and/or a polynucleotide encoding the heavy chain constant region of SEQ ID NO: 68; or, (8) a vector comprising a variant nucleotide encoding at least one substitution of an amino acid selected from the group of amino acids at position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440, as defined by the EU numbering system, in a polynucleotide encoding the heavy chain variable region and light chain variable region according to any of (i) to (l) of (6) above, and a polynucleotide encoding the light chain constant region of SEQ ID NO: 73, and/or a polynucleotide encoding the heavy chain constant region of SEQ ID NO: 68.

[9] A host cell comprising a vector selected from a group consisting of the following (1) to (4):

(1) the vector according to (1) of [8] and the vector according to (4) of [8];

(2) the vector according to (2) of [8] and the vector according to (5) of [8];

(3) the vector according to (3) of [8] and the vector according to (5) of [8]; or, (4) the vector according to any of (6) to (8) of [8].

[10] The host cell according to [9], wherein the host cell is a host cell having a poor ability to add fucose to a sugar chain.

[11] The host cell according to [10], wherein the host cell having poor ability to add fucose to a sugar chain is a cell deficient in one or more functional proteins selected from the group consisting of fucosyltransferase, fucose transporter, GDP-mannose 4,6-dehydratase (GMD), GDP-keto-6-deoxymannose 3,5-epimellase-4-reductase (Fx) and GDP-β-L-fucose pyrophosphorylase (GFPP).

[12] The host cell according to [9], wherein the host cell is a host cell having activity that forms a sugar chain comprising a bisecting N-acetylglucosamine structure in the sugar chain.

[13] The host cell according to [12], wherein the host cell having activity that forms a sugar chain comprising a bisecting N-acetylglucosamine structure in the sugar chain has β(1,4)-galactosyltransferase activity and comprises a vector comprising a polynucleotide encoding a functional Golgi localization domain of a Golgi resident polypeptide.

[14] The host cell according to [13], wherein the host cell is a host cell comprising a vector comprising a polynucleotide encoding a functional Golgi localization domain selected from the group consisting of a localization domain of mannosidase II, a localization domain of β(1,2)-N-acetylglucosaminyltransferase I, a localization domain of β(1,2)-N-acetylglucosaminyltransferase II, a localization domain of mannosidase I and a localization domain of a core α1-6 fucosyltransferase, and a polynucleotide encoding a fused polypeptide comprising a catalytic domain of β(1,4)-galactosyltransferase.

[15] A method for producing the monoclonal antibody according to any of [1] to [7] comprising recovering from a culture fluid of the host cell according to any of [9] to [14].

[16] A monoclonal antibody produced according to the method according to [15].

[17] A pharmaceutical composition comprising the monoclonal antibody according to any of [1] to [7] and [16] as an active ingredient thereof.

[18] The pharmaceutical composition according to [17], which is combined with IL-6 or a fragment, variant, fused protein, functional derivative or salt thereof.

[19] An anticancer drug comprising the monoclonal antibody according to any of [1] to [7] and [16] as an active ingredient thereof.

[20] The anticancer drug according to [19], wherein the cancer is multiple myeloma.

[21] The anticancer drug according to [19] or [20], which is administered with IL-6 or a fragment, variant, fused protein, functional derivative or salt thereof.

One Embodiment of Advantageous Effects of Invention

According to the present invention, a monoclonal antibody is provided which binds to LAMP5. The monoclonal antibody of the present invention is able to exhibit cytotoxicity and internalization activity by binding to LAMP5 expressed on a cell surface. Thus, according to the present invention, novel anticancer drugs and novel treatment methods and the like can be developed for cancer such as multiple myeloma.

Figure 1:
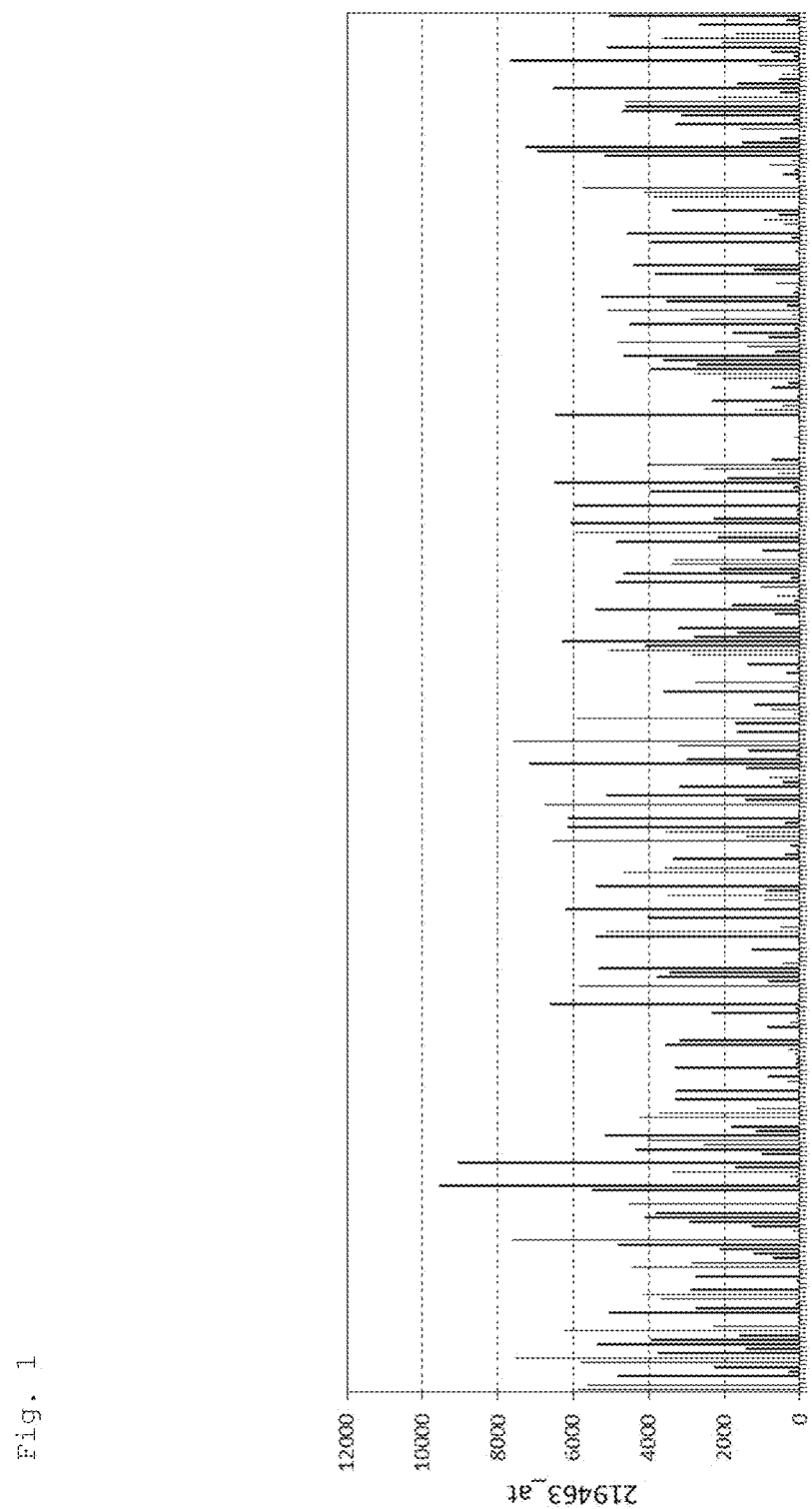
FIG. 1 is a graph illustrating expression of LAMP5 in multiple myeloma clinical specimens using the Human Genome U133 Plus 2.0 Array.

The following definitions and detailed explanation are provided to facilitate understanding of the present invention as explained in the present description.

DEFINITIONS

Amino Acids

In the present description, amino acids are illustrated with a single-letter code, three-letter code or both as is represented by Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I or Val/V. Furthermore, although amino acids comprised in amino acid sequences illustrated in the present invention may be subjected to alteration following translation (for example, alteration of an N-terminal glutamine to pyroglutamic acid by pyroglutamylation is well known by persons with ordinary skill in the art), such cases of an amino acid being altered following translation are naturally also comprised in the amino acid sequences illustrated in the present invention.

Antigen

The antibody provided by the present invention binds to LAMP5. The amino acid sequence of LAMP5 is disclosed in GenBank Accession No. NP_036393.1 (SEQ ID NO: 65). In the present invention, the full length protein and a fragment thereof are both comprised in the definition of LAMP5. A fragment refers to a polypeptide comprising an arbitrary region of LAMP5 and is not required to have the function of naturally-occurring LAMP5. An example of a fragment is a fragment comprising an extracellular region of LAMP5.

The full length protein of LAMP5 consists of 280 amino acids (SEQ ID NO: 65), positions 1 to 29 correspond to a signal sequence, the extracellular region corresponds to positions 30 to 235, the transmembrane region corresponds to positions 236 to 256, and the intracellular region corresponds to positions 257 to 280.

An amino acid sequence obtained by inserting an HA tag sequence (amino acid sequence YPYDVPDYA) immediately under the signal sequence (positions 1 to 29) of LAMP5 is illustrated in SEQ ID NO: 8. The amino acid sequence of LAMP5 protein from which the signal sequence has been removed corresponds to positions 30 to 280 of SEQ ID NO: 65 and positions 39 to 289 of SEQ ID NO: 8.

In the present invention, an epitope as referring to an antigen determinant present in an antigen refers a region in an antigen bound by an antigen-binding domain in the anti-LAMP5 antibody disclosed in the present description. Accordingly, an epitope can be defined, for example, by the structure thereof. In addition, that epitope can also be defined by the binding activity of anti-LAMP5 antibody recognizing said epitope to an antigen. In the case the antigen is a peptide or polypeptide, the epitope can also be specified by the amino acid residues forming said epitope. In addition, in the case an epitope is a sugar chain, the epitope can also be specified by a specific sugar chain structure.

A linear epitope is, for example, an epitope recognized from the primary sequence of an amino acid in the manner of an epitope formed by a plurality of contiguous amino acids in the primary sequence of an amino acid. Typically, a linear epitope comprises at least three, and more usually comprises at least five (for example, 8 to 10 or 6 to 20) amino acids in a unique sequence.

In contrast to linear epitopes, a conformational epitope is epitope wherein the primary sequence of amino acids comprising the epitope is not the sole defining component of the recognized epitope (such as an epitope wherein the primary sequence of amino acids is not necessarily recognized by the antibody that defines the epitope). A conformation epitope typically encompasses an increased number of amino acids relative to a linear epitope. With respect to recognition of a conformational epitope, antibody recognizes a three-dimensional structure of the peptide or protein. For example, when a protein molecule folds to form a three-dimensional structure, certain amino acids and/or the polypeptide backbone forming the conformational epitope become juxtaposed enabling the antibody to recognize that epitope. Examples of Methods of determining the three-dimensional structure of an epitope include, but are not limited to, X-ray crystallography, two-dimensional nuclear magnetic resonance spectroscopy, site-directed spin labeling and electron paramagnetic resonance spectroscopy. Refer to, for example, Epitope Mapping Protocols in Methods in Molecular Biology (1996), Vol. 66, Morris, G., ed.).

Binding Activity

Although the following lists an example of a method used to confirm binding of antibody to LAMP5 (namely, to an epitope present in an LAMP5 molecule), the present invention is not limited to the following method, but rather a person with ordinary skill in the art can suitably use a known method used to measure binding of antibody to antigen.

Recognition of a linear epitope present in an LAMP5 molecule by anti-LAMP5 antibody can be confirmed, for example, in the manner illustrated below. A linear peptide composed of an amino acid sequence that composes the extracellular domain of LAMP5 is synthesized for the above-mentioned purpose. This peptide can be chemically synthesized. Alternatively, this peptide can be synthesized using a genetic engineering technique by utilizing a region that encodes an amino acid sequence corresponding to the extracellular domain present in cDNA encoding LAMP5 (an example of which is NM_012261.2 (SEQ ID NO: 66)). Next, binding activity is evaluated between the linear peptide composed of an amino acid sequence that forms the extracellular domain and anti-LAMP5 antibody. Binding activity of the antibody to the peptide can be evaluated by, for example, ELISA using an immobilized linear peptide as an antigen. Alternatively, binding activity to a linear peptide can be determined based on the level of inhibition by the linear peptide during binding of the antibody to LAMP5-expressing cells. Binding activity of the antibody to a linear peptide can be determined by these methods.

In addition, recognition of a conformational epitope by anti-LAMP5 antibody can be confirmed in the manner illustrated below. Cells expressing LAMP5 are prepared for the above-mentioned purpose. Although anti-LAMP5 antibody strongly binds to the LAMP5-expressing cells when contact is made with the cells, the antibody does not substantially bind to a linear peptide composed of an amino acid sequence that forms an immobilized extracellular domain of LAMP5. Here, "does not substantially bind" refers to binding activity to LAMP5-expressing cells of 80% or less, normally 50% or less, preferably 30% or less and particularly preferably 15% or less.

Examples of methods used to measure the binding activity of anti-LAMP5 antibody to LAMP5-expressing cells are illustrated in Antibodies: A Laboratory Manual (Ed Harlow, David Lane, Cold Spring Harbor Laboratory (1988) 359-420). Namely, binding activity can be evaluated based on the principle of ELISA or fluorescence activated cell sorting (FACS) using LAMP5-expressing cells as antigen.

In the ELISA format, binding activity of anti-LAMP5 antibody to LAMP5-expressing cells can be evaluated quantitatively by comparing signal levels generated by an enzyme reaction. Namely, a test antibody is added to an ELISA plate immobilized with LAMP5-expressing cells, and the test antibody bound to the cells is detected by utilizing an enzyme-labeled antibody that recognizes the test antibody. Alternatively, in FACS, a series of dilution of a test antibody is prepared and an antibody binding titer with respect to LAMP5-expressing cells is determined thereby making it possible to compare binding activities of test antibodies to LAMP5-expressing cells.

Binding activity of a test antibody to an antigen expressed on the surface of cells suspended in a buffer and the like can be detected by flow cytometry. Apparatuses like those illustrated below are known to be examples of flow cytometers.

FACSCanto™ II
FACSAria™
FACSArrayII™
FACSVantage™ SE
FACSCalibur™
(All of the above are trade names of BD Biosciences Inc.)
EPICS ALTRA HyPerSort
Cytomics FC 500
EPICS XL-MCL ADC EPICS XL ADC
Cell Lab Quanta/Cell Lab Quanta SC
(All of the above are trade names of Beckman Coulter Inc.)

The following illustrates an example of a suitable method for measuring binding activity of anti-LAMP5 antibody to LAMP5. First, secondary antibody labeled with FITC that recognizes a test antibody that has reacted with cells expressing LAMP5 is stained. The anti-LAMP5 antibody is used after adjusting to a desired concentration by suitably diluting the test antibody with a preferable buffer. For example, the anti-LAMP5 antibody can be used at any concentration within the range of 10 µg/ml to 10 ng/ml. Next, fluorescence intensity and cell count are measured with FACSCalibur (BD Inc.). The amount of antibody bound to the cells is reflected in the value of fluorescence intensity, namely the value of the geometric mean thereof, obtained by analyzing using CELL QUEST software (BD Inc.). Thus, by obtaining the value of the geometric mean, binding activity of the test antibody can be measured as represented by the bound amount of test antibody. The above-mentioned method can be used to confirm whether or not a test antibody binds to an epitope present at positions 30 to 285 of LAMP 5 (SEQ ID NO: 65) (positions 39 to 289 of SEQ ID NO: 8) expressed on the cell surface.

The following antibodies illustrate examples of preferable embodiments of the anti-LAMP5 antibody of the present invention:

(i) antibody retaining the same CDRs as the D1 antibody illustrated in the examples (antibody comprising a heavy chain variable region comprising the CDR1 defined by SEQ ID NO: 35, the CDR2 defined by SEQ ID NO: 36 and the CDR3 defined by SEQ ID NO: 37 and a light chain variable region comprising the CDR1 defined by SEQ ID NO: 38, the CDR2 defined by SEQ ID NO: 39 and the CDR3 defined by SEQ ID NO: 40);

(ii) antibody retaining the same CDRs as D2 antibody illustrated in the examples (antibody comprising a heavy chain variable region comprising the CDR1 defined by SEQ ID NO: 41, the CDR2 defined by SEQ ID NO: 42 and the CDR3 defined by SEQ ID NO: 43 and a light chain variable region comprising the CDR1 defined by SEQ ID NO: 44, the CDR2 defined by SEQ ID NO: 45 and the CDR3 defined by SEQ ID NO: 46);

(iii) antibody retaining the same CDRs as D9 antibody illustrated in the examples (antibody comprising a heavy chain variable region comprising the CDR1 defined by SEQ ID NO: 47, the CDR2 defined by SEQ ID NO: 48 and the CDR3 defined by SEQ ID NO: 49 and a light chain variable region comprising the CDR1 defined by SEQ ID NO: 50, the CDR2 defined by SEQ ID NO: 51 and the CDR3 defined by SEQ ID NO: 52); and, (iv) antibody retaining the same CDRs as D10 antibody illustrated in the examples (antibody comprising a heavy chain variable region comprising the CDR1 defined by SEQ ID NO: 53, the CDR2 defined by SEQ ID NO: 54 and the CDR3 defined by SEQ ID NO: 55 and a light chain variable region comprising the CDR1 defined by SEQ ID NO: 56, the CDR2 defined by SEQ ID NO: 57 and the CDR3 defined by SEQ ID NO: 58).

Figure 2A:
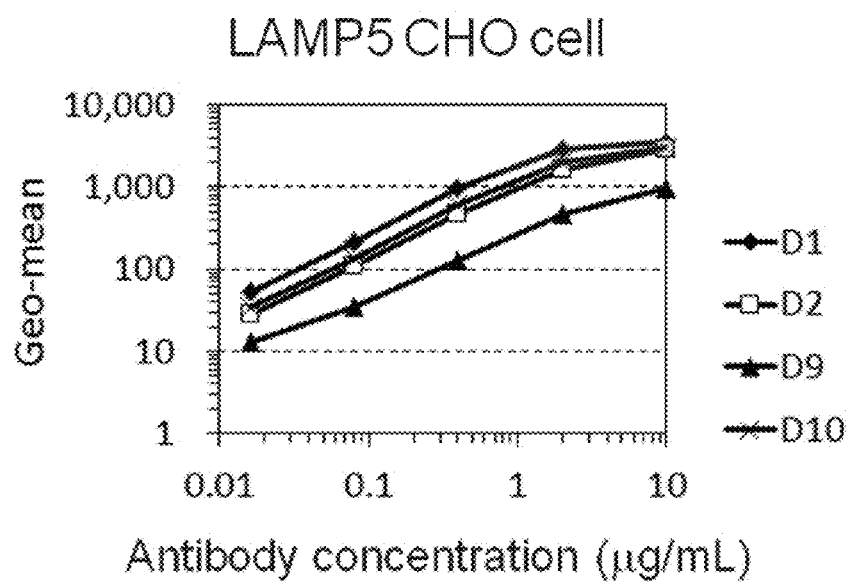
FIG. 2A is a graph illustrating the results of FACS for evaluating binding of anti-LAMP5 monoclonal antibodies D1, D2, D9 and D10 to LAMP5 CHO cells.
Figure 2B:
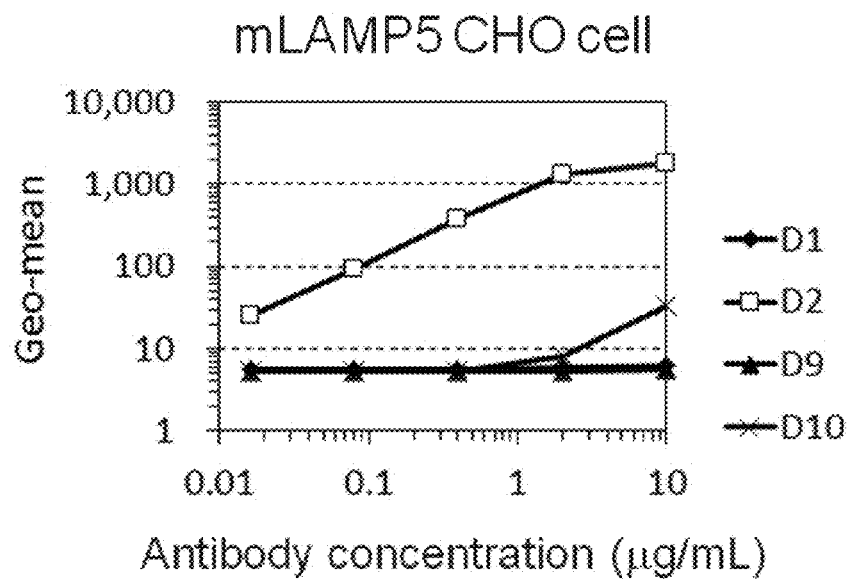
FIG. 2B is a graph illustrating the results of FACS for evaluating binding of anti-LAMP5 monoclonal antibodies D1, D2, D9 and D10 to mLAMP5 CHO cells.

In the FACS analysis illustrated in Example 4-2, clones D1, D2, D9 and D10 all bound concentration-dependently to LAMP5 (FIG. 2A). Clones D1, D2 and D10 in particular bound strongly as compared with clone D9 (FIG. 2A). On the other hand, although clone D2 strongly bound to mouse-origined LAMP5 (mLAMP5), clones D1 and D9 did not bind (FIG. 2B). Clone D10 only weakly bound to mLAMP5 (FIG. 2B).

Thus, the above-mentioned antibodies are antibodies that have binding activity to LAMP5.

Anti-LAMP5 antibodies have been confirmed to share a certain antibody and epitope through competitive bonding of both to the same epitope. Competitive binding between antibodies is detected by, for example, a cross-blocking assay. A competitive ELISA assay is a preferable example of a cross-blocking assay.

More specifically, in a cross-blocking assay, a test antibody is added after pre-incubating LAMP5 protein coated onto the wells of a microtiter plate in the presence or absence of a candidate competing antibody. The amount of test antibody bound to LAMP5 protein in the wells correlates indirectly with the binding capacity of the candidate competing antibody that competes for binding to the same epitope. Namely, the greater the affinity of the competing antibody for the same epitope, the lower the binding activity of the test antibody to the wells coated with LAMP5 protein.

The amount of test antibody bound to the wells through LAMP5 protein can be measured easily by labeling the antibody in advance. For example, biotin-labeled antibody is measured by using avidin-peroxidase conjugate and a suitable substrate. Cross-blocking assays using peroxidase or other enzyme labeling in particular are referred to as competitive ELISA assays. Antibody can be labeled with another labeling substance that enables detection or measurement. Known specific examples thereof include radioactive labeling and fluorescence labeling.

After comparing with binding activity obtained in a reference test carried out in the absence of the candidate competing antibody, if binding of antibody to LAMP5 is able to be blocked by the competing antibody by at least 20%, preferably at least 30%, more preferably at least 40% and even more preferably at least 50%, then the test antibody is an antibody that either binds to substantially the same epitope as the competing antibody or competes for binding to the same epitope.

In the case the structure of an epitope bound by anti-LAMP5 antibody has been identified, sharing of an epitope by a test antibody and reference antibody can be evaluated by comparing the binding activities of both antibodies to a peptide in which an amino acid mutation has been introduced into a peptide that composes the epitope.

An example of a method used to measure such binding activity consists of measuring binding activity by comparing the binding activities of a test antibody and reference antibody to a linear peptide introduced with a mutation using the above-mentioned ELISA format. As an example of a method other than ELISA, binding activity to a mutant peptide bound to a column can be measured by quantifying antibody eluted into a solution after passing a test antibody and reference antibody through the column. A known method consists of adsorbing a mutant peptide in the form of a fused peptide with GST, for example, onto a column.

In addition, in the case an identified epitope is a conformational epitope, sharing of an epitope by a test antibody and reference antibody can be evaluated by the method illustrated below. First, cells expressing LAMP5 and cells expressing LAMP5 in which a mutation is introduced into an epitope are prepared. The test antibody and reference antibody are added to a cell suspension obtained by suspending these cells in a suitable buffer such as PBS. Next, after washing the cell suspension with a suitable buffer, FITC-labeled antibody that is able to recognize the test antibody and reference antibody is added to the washed cell suspension. Fluorescence intensity and cell count of those cells stained by the labeled antibody are measured with FACSCalibur (BD Inc.). The concentrations of the test antibody and reference antibody are adjusted to a desired concentration by suitably diluting with a preferable buffer prior to use. For example, the test antibody and reference antibody are used at any concentration within the range of 10 µg/ml to 10 ng/ml. The amount of labeled antibody which binds to the cells is reflected in the fluorescence intensity obtained by analyzing using CELL QUEST Software (BD Inc.), namely in the value of the geometric mean thereof. Thus, the binding activities of the test antibody and reference antibody as represented by the amount of bound labeled antibody can be measured by obtaining values of the geometric mean.

In this method, "substantially does not bind to variant LAMP5-expressing cells" can be determined, for example, according to the method illustrated below. First, a test antibody and reference antibody bound to variant LAMP5-expressing cells are stained with a labeled antibody. Next, the fluorescence intensity of the cells is detected. In the case of using the FACSCalibur for flow cytometry when detecting fluorescence, the resulting fluorescence intensity can be analyzed using CELL QUEST Software. The rate of increase in fluorescence intensity attributable to antibody binding can be determined by calculating a comparative value (ΔGeo-Mean) from the values of the geometric mean in the presence and absence of antibody.

ΔGeo-Mean=Geo-Mean(presence of antibody)/Geo-Mean (absence of antibody)

The geometric mean comparative value (ΔGeo-Mean of variant LAMP5 molecule) reflecting the amount of test antibody bound to the variant LAMP5-expressing cells as obtained by analysis is compared with the ΔGeo-Mean comparative value that reflects the amount of test antibody bound to LAMP5-expressing cells. In this case, the concentrations of test antibody used when determining ΔGeo-Mean comparative values for the variant LAMP5-expressing cells and LAMP5-expressing cells are particularly preferably adjusted to mutually the same or substantially the same concentration. An antibody which has been preliminarily confirmed to recognize an epitope in LAMP5 is used for the reference antibody.

The test antibody "does not substantially bind to variant LAMP5-expressing cells" if the ΔGeo-Mean comparative value of the test antibody to the variant LAMP5-expressing cells is smaller than 80%, preferably smaller than 50%, more preferably smaller than 30% and particularly preferably smaller than 15% of the ΔGeo-Mean comparative value of the test antibody to LAMP5-expressing cells. The calculation formula for determining geometric mean (Geo-Mean) values is illustrated in the CELL QUEST Software User's Guide (BD Biosciences Inc.). If the comparative values are to a degree that they can be considered to be substantially the same as a result of a comparison thereof, then the epitopes of the test anti-LAMP5 antibody and reference anti-LAMP5 antibody can be evaluated as being the same.

Antibody

In the present description, an antibody refers to a naturally-occurring antibody or an immunoglobulin produced by partial or complete synthesis. Antibodies can be isolated from natural resources such as plasma or serum in which they are naturally present or from the culture supernatants of hybridoma cells that produce antibodies, or they can be partially or completely synthesized using techniques such as gene recombination. Preferable examples of antibodies include isotypes of immunoglobulins and subclasses of those isotypes. Nine classes (isotypes) of human immunoglobulins are known, consisting of IgG1, IgG2, IgG3, IgG4, IgA1, IgA2, IgD, IgE and IgM. Among these isotypes, IgG1, IgG2, IgG3 and IgG4 are comprised in the antibodies of the present invention.

Methods for producing antibodies having a desired binding activity are known by persons with ordinary skill in the art. The following illustrates a non-limiting example of a method for producing antibody which binds to LAMP5 (anti-LAMP5 antibody).

Anti-LAMP5 antibody can be obtained in the form of polyclonal antibody or monoclonal antibody using known means. A mammalian monoclonal antibody can be preferably produced for use as anti-LAMP5 antibody. Monoclonal antibodies produced by hybridomas and those produced by host cells that have been transformed with an expression vector comprising an antibody gene by a genetic engineering technique are included in the mammalian monoclonal antibody. Furthermore, "humanized antibody" and "chimeric antibody" are included in the monoclonal antibody of the present invention.

A hybridoma producing monoclonal antibody can be produced in the manner illustrated below, for example, using a known art. Namely, a mammal is immunized in accordance with an ordinary immunization method using LAMP5 protein as sensitizing antigen. The resulting immune cells are fused with known parent cells according to a known cell fusion method. Next, cells producing monoclonal antibody which bind to an epitope in a LAMP5 molecule are screened by an ordinary screening method, thereby making it possible to select a hybridoma that produces anti-LAMP5 monoclonal antibody.

Production of monoclonal antibody is carried out, for example, in the manner illustrated below. First, LAMP5 protein represented by SEQ ID NO: 65, which is used as a sensitizing antigen during obtaining antibody, can be obtained by expressing LAMP5 gene for which the nucleotide sequence thereof has been disclosed in SEQ ID NO: 66. Namely, suitable host cells are transformed by inserting a gene sequence encoding LAMP5 into a known expression vector. A desired LAMP5 protein is purified using a known method from the host cells or culture supernatant thereof. In order to obtain soluble LAMP5 from a culture supernatant, a protein composed of amino acids at positions 30 to 235 in the LAMP5 polypeptide sequence represented by SEQ ID NO: 65, for example, is expressed instead of the LAMP5 protein represented by SEQ ID NO: 65. In addition, purified naturally-occurring LAMP5 protein can also be similarly used as sensitizing antigen.

The purified LAMP5 protein can be used as sensitizing antigen that is used to immunize a mammal. A partial peptide of LAMP5 can also be used as sensitizing antigen. At this time, the partial peptide can be obtained by chemical synthesis from the amino acid sequence of LAMP5. In addition, a partial peptide can also be obtained by incorporating a portion of LAMP5 gene in an expression vector and expressing therein. Moreover, although a partial peptide can also be obtained by digesting LAMP5 protein using a protease, the region and size of the LAMP5 peptide used as a partial peptide are not particularly limited to a specific manner. An arbitrary sequence can be selected from the amino acid sequence corresponding to amino acids at positions 30 to 235 in the amino acid sequence represented in SEQ ID NO: 65 as a preferable region. The number of amino acids that form the peptide to be used as sensitizing antigen is at least 5 or more, for example 6 or more and preferably 7 or more. More specifically, a peptide consisting of 8 to 50 residues, and preferably 10 to 30 residues, can be used as sensitizing antigen.

In addition, a fused protein obtained by fusing a desired partial polypeptide of LAMP5 protein and a polypeptide having a different peptide can be used as sensitizing antigen. An antibody Fc fragment or peptide tag, for example, can be preferably used to produce a fused protein for use as sensitizing antigen. A vector that expresses the fused protein can be produced by fusing genes encoding two or more types of desired polypeptide fragments in-frame and inserting the fused gene into an expression vector as previously illustrated. Methods for producing fused proteins are illustrated in Molecule Cloning, 2nd edition (Sambrook, J. et al., Molecular Cloning 2nd ed., 9.47-9.58 (1989), Cold Spring Harbor Laboratory Press).

Although the mammal immunized with the sensitizing antigen is not limited to a specific animal, it is preferably selected in consideration of compatibility with the parent cells used in cell fusion. In general, rodent cells (such as mouse, rat or hamster cells) or rabbit or monkey cells are used preferably.

The above-mentioned animal is immunized with sensitizing antigen in accordance with a known method. A typical example thereof consists of carrying out immunization by administering the sensitizing antigen by intraperitoneal or subcutaneous injection into a mammal. More specifically, after diluting at a suitable dilution factor with phosphate-buffered saline (PBS) or physiological saline and the like, the sensitizing antigen is combined with an ordinary adjuvant such as Freund's complete adjuvant as desired and emulsified therein followed by administering the sensitizing antigen into a mammal multiple times every 4 to 21 days. In addition, a suitable carrier can be used when immunizing with the sensitizing antigen. In the case of using a partial peptide having low molecular weight as sensitizing antigen in particular, there are cases in which it is desirable to immunize with a sensitizing antigen peptide bound to a carrier protein such as albumin or keyhole limpet hemocyanin.

In addition, a hybridoma that produces a desired antibody can be produced in the manner illustrated below using DNA immunization. DNA immunization is an immunization method for imparting immune stimulation in an immune animal by expressing a sensitizing antigen within the body of the immune animal that has been administered vector DNA constructed in a manner such that a gene encoding antigen protein can be expressed in the immune animal. DNA immunization is expected to be superior to ordinary immunization methods consisting of administering a protein antigen into an immune animal for the reasons illustrated below.

Immune stimulation can be imparted while maintaining the structure of a membrane protein in the manner of LAMP5.

It is not necessary to purify the immunizing antigen.

DNA expressing LAMP5 protein is first administered to an immune animal in order to obtain the monoclonal antibody of the present invention by DNA immunization. DNA encoding LAMP5 can be synthesized by a known method such as PCR. The resulting DNA is inserted into a suitable expression vector and then administered to an immune animal. Examples of expression vectors that can be used preferably include commercially available expression vectors such as pcDNA3.1. A commonly used method can be used to administer the vector into the body. For example, DNA immunization is carried out by introducing gold particles having an expression vector adsorbed thereto into the cells of an individual immune animal with a gene gun.

After immunizing a mammal in this manner and confirming an increase in the serum titer of antibody which binds to LAMP5, immune cells are collected from the mammal and subjected to cell fusion. Spleen cells can be used particularly preferably as immune cells.

Mammalian myeloma cells are used for the cells that are fused with the above-mentioned immune cells. The myeloma cells are preferably provided with a suitable selection marker for screening. A selection marker refers to a trait by which the cell is able (or unable) to survive under specific culturing conditions. Known examples of selection markers include hypoxanthine-guanine phosphoribosyltransferase deficiency (to be abbreviated as HGPRT deficiency) and thymidine kinase deficiency (to be abbreviated as TK deficiency). Cells having a deficiency of HGPRT or TK exhibit hypoxanthine-aminopterin-thymidine sensitivity (to be abbreviated as HAT sensitivity). Although HAT-sensitive cells are unable to carry out DNA synthesis in HAT selective medium and die out as a result thereof, when fused with normal cells, these cells grow even in HAT selective medium since they are able to sustain DNA synthesis by using the salvage pathway of the normal cells.

HGPRT-deficient or TK-deficient cells can be selected in medium comprising 6-thioguanine, 8-azaguanine or 5'-bromodeoxyuridine. Normal cells that incorporate these pyrimidine analogues into their DNA end up dying. On the other hand, cells deficient in the above-mentioned enzymes that are unable to incorporate these pyrimidine analogues are able to survive in this selective medium. In addition, a selection marker referred to as G418 tolerance imparts tolerance to 2-deoxystreptamine-based antibiotics (gentamycin analogues) through a neomycin resistance gene. Various types of myeloma cells are known that are preferable for cell fusion.

Examples of such myeloma cells that can be used preferably include P3 (P3×63Ag8.653) (J. Immunol. (1979) 123(4), 1548-1550), P3×63Ag8U.1 (Current Topics in Microbiology and Immunology (1978) 81, 1-7), NS-1 (C. Eur. J. Immunol. (1976) 6(7), 511-519), MPC-11 (Cell (1976) 8(3), 405-415), SP2/0 (Nature (1978) 276 (5685), 269-270), FO (J. Immunol. Methods (1980) 35(1-2), 1-21), S194/5.XXO.BU.1 (J. Exp. Med. (1978) 148(1), 313-323) and R210 (Nature (1979) 277(5692), 131-133).

The above-mentioned immune cells and myeloma cells are basically fused in accordance with, for example, the method of Kohler and Millstein (Methods Enzymol. (1981) 73, 3-46).

More specifically, the above-mentioned cell fusion can be carried out in ordinary nutrient culture medium in the presence of a cell fusion promoting agent, for example. Examples of cell fusion promoting agent used include polyethylene glycol (PEG) and Sendai virus (HVJ), and an assistant such as dimethylsulfoxide may be added as desired to further enhance fusion efficiency.

The ratio at which the immune cells and myeloma cells are used can be set arbitrarily. For example, the number of immune cells is preferably 1 to 10 times the number of myeloma cells. RPMI1640 culture medium or MEM culture medium preferable for the proliferation of the above-mentioned myeloma cells, or ordinary culture medium used for this type of cell culturing, is used for the culture medium used in the above-mentioned cell fusion, and a serum complement such as fetal calf serum (FCS) can also be preferably added.

In the case of cell fusion, prescribed amounts of the above-mentioned immune cells and myeloma cells are combined well in the above-mentioned culture medium followed by the addition of PEG solution (such as that having an average molecular weight of about 1000 to 6000) prewarmed to a temperature of 37° C. and normally at a concentration of 30% (w/v) to 60% (w/v). The desired fused cells (hybridomas) are formed by gently inverting the combined fluid. Next, cell fusion agents and the like undesirable for hybridoma growth can be removed by repeating a procedure consisting of successively adding the suitable culture media as previously illustrated, centrifuging and removing the supernatant.

A hybridoma obtained in this manner can be selected by culturing in ordinary selective culture medium such as HAT culture medium (culture medium comprising hypoxanthine, aminopterin and thymidine). Culturing using the above-mentioned HAT culture medium can be continued for an amount of time sufficient for eliminating cells (non-fused cells) other than the desired hybridoma (normally, several days to several weeks are required). Next, screening and monocloning of hybridoma producing the desired antibody are carried out by an ordinary limiting dilution technique.

A hybridoma obtained in this manner can be selected by using a selective culture medium corresponding to the selection marker possessed by the myeloma used for cell fusion. For example, HGPRT-deficient or TK-deficient cells can be selected by culturing in HAT culture medium (culture medium comprising hypoxanthine, aminopterin and thymidine). Namely, in the case of using HAT-sensitive myeloma cells in cell fusion, those cells that undergo successful cell fusion with normal cells in HAT culture medium are able to grow selectively. Culturing using the above-mentioned HAT culture medium is continued for an amount of time sufficient for eliminating cells (non-fused cells) other than the desired hybridoma cells. More specifically, the desired hybridoma can typically be selected by culturing for several days to several weeks. Next, screening and monocloning of hybridoma producing the desired antibody are carried out by an ordinary limiting dilution technique.

Screening and monocloning of the desired antibody can be preferably carried out according to a screening method based on a known antigen-antibody reaction. For example, monoclonal antibody which binds to LAMP5 can be bound to LAMP5 expressed on the cell surface. Such a monoclonal antibody can be screened by fluorescence activated cell sorting (FACS). FACS is a system that makes it possible to measure binding of antibody to a cell surface by analyzing cells that have contacted a fluorescent antibody with laser light and measuring fluorescence emitted by individual cells.

Cells expressing LAMP5 are first prepared in order to screen for hybridomas producing the monoclonal antibody of the present invention by FACS. Mammalian cells that strongly express LAMP5 are preferable for screening. Binding activity of antibody to LAMP5 on the cell surface can be selectively detected by using non-transformed mammalian cells used as host cells as a reference. Namely, hybridoma producing LAMP5 monoclonal antibody can be obtained by selecting a hybridoma that produces antibody which binds to the cells strongly expressing LAMP5 without binding to the host cells.

Alternatively, binding activity of antibody to immobilized LAMP5-expressing cells can be evaluated based on the principle of ELISA. For example, LAMP5-expressing cells are immobilized in the wells of an ELISA plate. Hybridoma culture supernatant is then contacted with the immobilized cells in the wells of the ELISA plate and antibody which binds to the immobilized cells is detected. In the case a monoclonal antibody is obtainable from mice, antibody which binds to the cells can be detected by anti-mouse immunoglobulin antibody. A hybridoma selected by these screening procedures that produces a desired antibody having binding capacity with respect to antigen can be cloned by a limiting dilution technique and the like.

A hybridoma that produces antibody produced in this manner can be subcultured in ordinary culture medium. In addition, the hybridoma can be stored over a long period of time in liquid nitrogen.

The hybridoma can be cultured in accordance with ordinary methods and a desired monoclonal antibody can be obtained from the culture supernatant thereof. Alternatively, the hybridoma can be allowed to proliferate by administering to a mammal having compatibility therewith and monoclonal antibody can be obtained from the ascites thereof. The former method is preferable for obtaining highly pure antibody.

Antibody can also be preferably used that is encoded by an antibody gene cloned from antibody-producing cells such as the above-mentioned hybridoma. Antibody encoded by a cloned antibody gene is expressed by incorporating the gene in a vector and introducing into a host. Methods for isolating the antibody gene, introducing into a vector and transforming host cells have already been established by, for example, Vandamme et al. (Eur. J. Biochem. (1990) 192 (3), 767-775). The method for producing recombinant antibody illustrated below is also known.

For example, cDNA encoding a variable region (V region) of anti-LAMP5 antibody is obtained from hybridoma cells producing anti-LAMP5 antibody. In order to accomplish this, normally total RNA is first extracted from the hybridoma. Methods like those illustrated below can be used to extract mRNA from cells:

guanidine ultracentrifugation (Biochemistry (1979) 18(24), 5294-5299); and, acid-guanidine/phenol/chloroform (AGPC) extraction (Anal. Biochem. (1987) 162(1), 156-159).

Extracted mRNA can be purified using an mRNA purification kit (GE Healthcare Bio-Sciences Corp.). Alternatively, kits such as the QuickPrep mRNA Purification Kit (GE Healthcare Bio-Sciences Corp.) are commercially available for directly extracting total mRNA from cells. mRNA is obtained from a hybridoma using such a kit. cDNA encoding antibody V region can be synthesized from the resulting mRNA using reverse transcriptase. The cDNA can be synthesized with, for example, the AMV Reverse Transcriptase First-strand cDNA Synthesis Kit (SEIKAGAKU CORPORATION). In addition, the SMART RACE cDNA Amplification Kit (Clontech Laboratories, Inc.) and the 5'-RACE method using PCR (Proc. Natl. Acad. Sci. USA (1988) 85(23), 8998-9002; Nucleic Acids Res. (1989) 17(8), 2919-2932) can be suitably used to synthesize and amplify cDNA. Moreover, suitable restriction enzyme sites to be subsequently illustrated can be introduced onto both terminals of the cDNA during the course of this cDNA synthesis.

A target cDNA fragment is purified from the resulting PCR product and then linked with vector DNA. After producing such a recombinant vector, introducing into Escherichia coli and the like and selecting the resulting colonies, a desired recombinant vector can be prepared from the E. coli that has formed the colonies. A known method such as dideoxynucleotide chain termination is used to confirm whether or not the recombinant vector retains the nucleotide sequence of the target cDNA.

The 5'-RACE method using a primer for amplifying a variable region gene can be easily used to obtain a gene encoding a variable region. First, cDNA is synthesizing by using as template RNA extracted from hybridoma cells to obtain a 5'-RACE cDNA library. A commercially available kit such as a SMART RACE cDNA amplification kit is suitably used to synthesize the 5'-RACE cDNA library.

The antibody gene is amplified by PCR by using the resulting 5'-RACE cDNA library as template. Primers for amplifying mouse antibody gene can be designed based on a known antibody gene sequence. These primers have nucleotide sequences that differ for each subclass of immunoglobulin. Thus, it is desirable to determine subclass in advance using a commercially available kit such as the Iso Strip Mouse Monoclonal Antibody Isotyping Kit (Roche Diagnostics GmbH).

More specifically, when desiring to obtain a gene encoding mouse IgG, for example, a primer can be used that is capable of amplifying genes encoding heavy chains consisting of γ1, γ2a, γ2b and γ3 and light chains consisting of κ chain and λ chain. In order to amplify a variable region gene of IgG, a primer is typically used for the 3'-side primer that anneals to a portion corresponding to a constant region near the variable region. On the other hand, a primer provided with a 5'-RACE cDNA library production kit is used for the 5'-side primer.

Immunoglobulin composed of a combination of heavy chain and light chain can be reconfigured by using a PCR product amplified in this manner. Screening for a desired antibody can then be carried out by using binding activity of the reconfigured immunoglobulin to LAMP5 as an indicator. When desiring to obtain antibody to LAMP5, binding of the antibody to LAMP5 is more preferably specific. Antibody to LAMP5 can be screened, for example, using a process consisting of the steps illustrated below:

(1) a step for contacting an antibody comprising a V region encoded by cDNA obtained from a hybridoma with LAMP5-expressing cells,
(2) a step for detecting binding between the LAMP5-expressing cells and the antibody, and
(3) a step for selecting antibody which binds with the LAMP5-expressing cells.

Methods for detecting binding between an antibody and LAMP5-expressing cells are known. More specifically, binding between antibody and LAMP5-expressing cells can be detected by a technique such as FACS as previously illustrated. An immobilized specimen of LAMP5-expressing cells is suitably used to evaluate antigen binding activity.

A panning method using a phage vector is preferably used to screen antibody using binding activity as an indicator. In the case of obtaining antibody gene from a population of polyclonal antibody-producing cells in the form of a library of heavy chain and light chain subclasses, a screening method that uses a phage vector may be advantageous. A single chain Fv (scFv) can be formed by linking genes encoding heavy chain and light variable regions with a suitable linker sequence. A phage that expresses scFv on the surface thereof can be obtained by inserting a gene encoding scFv into a phage vector. After contacting this phage with a desired antigen, DNA encoding scFv having a target binding activity can be recovered by recovering phage that has bound to the antigen. An scFv having a desired binding activity can be concentrated by repeating this procedure as necessary.

After having obtained cDNA encoding the V region of a desired anti-LAMP5 antibody, the cDNA is digested by restriction enzyme recognizing restriction sites inserted into both terminals of the cDNA. A preferable restriction enzyme digests the cDNA by recognizing a nucleotide sequence that appears at a low frequency in the nucleotide sequence that composes the antibody gene. Moreover, a restriction enzyme that imparts a sticky end is preferably inserted in order to insert a single copy of the digested fragment into a vector in the proper direction. An antibody expression vector can be obtained by inserting cDNA encoding the V region of anti-LAMP5 antibody digested in the manner illustrated above into an expression vector. At this time, a chimeric antibody is obtained if a gene encoding the antibody constant region (C region) and a gene encoding the above-mentioned antibody V region are fused in-frame. Here, a "chimeric antibody" refers to an antibody in which the constant region and variable are from different origins. Thus, in addition to heterogeneous chimeric antibodies in the manner of mouse-human chimeric antibodies, human-human homogeneous chimeric antibodies are also included in chimeric antibodies in the present invention. A chimeric antibody expression vector can be constructed by inserting the above-mentioned V region gene into an expression vector preliminarily retaining a constant region. More specifically, a restriction enzyme recognition sequence of a restriction enzyme that digests the above-mentioned V region gene can be suitably arranged on the 5'-side of an expression vector that retains DNA encoding a desired antibody constant region (C region), for example. A chimeric antibody expression vector is constructed by fusing both genes that have been digested with the same combination of restriction enzymes in-frame.

Figure 7:
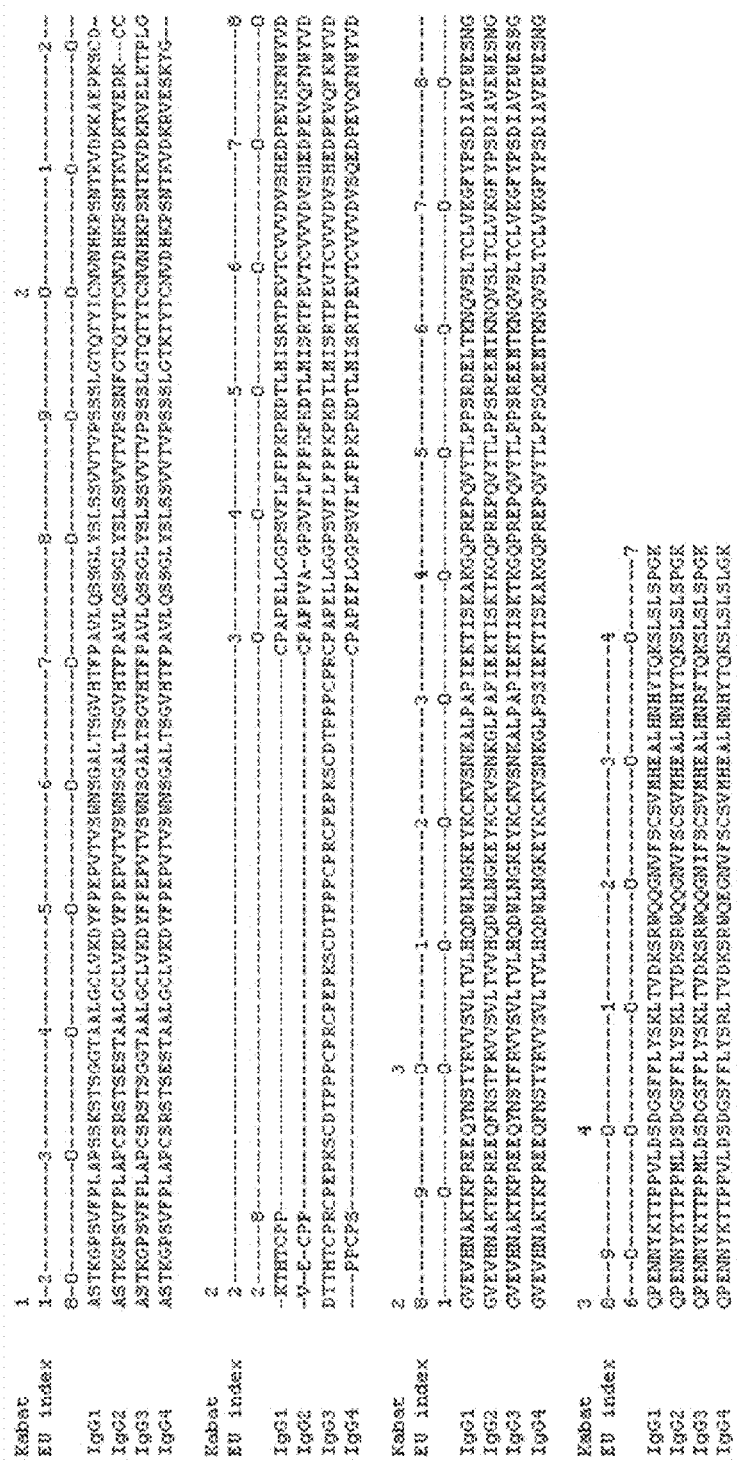
FIG. 7 is a diagram illustrating the sequences and 25 alignments of the constant regions of human antibodies: IgG1 (SEQ ID NO: 68), IgG2 (SEQ ID NO: 69), IgG3 (SEQ ID NO: 70; and IgG4 (SEQ ID NO:71).

The isotype of an antibody is determined according to the structure of the antibody constant region. The antibody constant regions of each of the isotypes of IgG1, IgG2, IgG3 and IgG4 are respectively referred to as Cγ1, Cγ2, Cγ3 and Cγ4. The polypeptide sequences of those regions that form the antibody constant regions of human Cγ1, Cγ2, Cγ3 and Cγ4 are illustrated in SEQ ID NO: 68, 69, 70 and 71. The relationships between the amino acid residues that form each of the polypeptide sequences and the Kabat and EU numbering systems are illustrated in FIG. 7. In addition, constant regions of the λ chain and κ chain are suitably used for the light chain antibody constant regions. The polypeptide sequences that form the human λ and κ antibody constant regions are illustrated in SEQ ID NO: 72 and 73.

In order to produce monoclonal antibody which binds to LAMP5, an antibody gene is inserted into an expression vector so that it is expressed under the control of an expression regulatory domain. An expression regulatory domain for expressing antibody comprises, for example, an enhancer or promoter. In addition, a suitable signal sequence can be added to the amino terminal so that the expressed peptide is secreted outside the cells. The expressed polypeptide is cleaved at the carboxyl terminal portion of the above-mentioned sequence and the cleaved polypeptide can be secreted outside the cells in the form of a mature polypeptide. Next, recombinant cells that express DNA encoding anti-LAMP5 antibody can be obtained by transforming suitable host cells with this expression vector.

In order to express antibody gene, DNA encoding antibody heavy chain (H chain) and antibody light chain (L chain) are respectively incorporated in different expression vectors. Antibody molecules provided with an H chain and L chain can be expressed by co-transfecting the same host cells with vectors incorporating the H chain and L chain. Alternatively, host cells can be transfected by incorporating DNA encoding H chain and L chain in a single expression vector (see WO 1994/011523).

Numerous combinations of host cells and expression vectors are known for producing antibody by introducing an isolated antibody gene into suitable host cells. All of these expression systems can be applied to isolation of the antigen binding domain of the present invention. In the case of using eukaryotic cells for the host cells, animal cells, plant cells or fungal cells can be used suitably. More specifically, examples of animal cells include the cells illustrated below:
 (1) mammalian cells: CHO, COS, myeloma, baby hamster kidney (BHK), Hela, Vero and human embryonic kidney (HEK) 293 cells;
 (2) amphibian cells: *Xenopus laevis* oocytes; and
 (3) insect cells: sf9, sf21 and Tn5.

Alternatively, known examples of plant cells include antibody gene expression systems using cells obtainable from plants of the genus *Nicotiana* such as *Nicotiana tabacum*. Cells cultured in the form of callus cells can be suitably used to transform plant cells.

Moreover, the following lists examples of fungal cells that can be used:
 yeast: *Saccharomyces* species such as *Saccharomyces cerevisiae* and *Pichia* species such as *Pichia pastoris*; and
 molds: *Aspergillus* species such as *Aspergillus niger*.

In addition, antibody gene expression systems are also known that use prokaryotic cells. For example, in the case of using bacterial cells, bacterial cells such as *E. coli* cells or *B. subtilis* cells can be used suitably. An expression vector comprising a target antibody gene is introduced into these cells by transformation. A desired antibody can be obtained from a culture of the transformed cells by culturing the transformed cells in vitro.

Transgenic animals can be used to produce a transformant in addition to the above-mentioned host cells. Namely, a desired antibody can be obtained from an animal introduced with a gene encoding the antibody. For example, an antibody gene can be constructed in the form of a fused gene by inserting in-frame into a gene that encodes a protein characteristically produced in breast milk. An example of a protein secreted into breast milk that can be used is goat β-casein. A DNA fragment comprising a fused gene inserted with antibody gene is injected into a goat embryo and the injected embryo is introduced into a female goat. The desired antibody can be obtained in the form of a fused protein with breast milk protein from breast milk produced by a transgenic goat (or progeny thereof) born from the goat that received the embryo. In addition, hormones can be administered to a transgenic goat to increase the amount of breast milk comprising the desired antibody produced by the transgenic coat (Bio/Technology (1994), 12(7), 699-702).

In the case of administering the anti-LAMP5 antibody illustrated in the present description to a human, an artificially modified gene recombinantly-obtainable antigen binding domain can preferably be employed as the antigen binding domain in the antibody for the purpose of lowering heteroantigenicity to humans. The gene recombinant includes, for example, humanized antibody. These modified antibodies can be suitably produced using known methods.

Antibody variable region used to produce the antigen binding domain in the anti-LAMP5 antibody of the present invention is normally composed of three complementarity-determining regions (CDR) interposed among four framework regions (FR). A CDR is a region that substantially determines the binding specificity of an antibody. The amino acid sequences of CDR are extremely diverse. On the other hand, the amino acid sequences that form FR frequently exhibit high identity even among antibodies having different binding specificities. Consequently, the binding specificity of a certain antibody is generally considered to be able to be grafted to another antibody by grafting CDR.

Humanized antibodies are also referred to as reshaped human antibodies. More specifically, humanized antibodies are known that are obtained by grafting the CDR of an antibody of a non-human animal such as a mouse to human antibody. Common gene recombination techniques for obtaining humanized antibodies are also known. More specifically, a known example of a method for grafting a CDR of mouse antibody to a human FR is overlap extension PCR. In overlap extension PCR, a nucleotide sequence encoding the CDR of a mouse antibody to be grafted is added to a primer for synthesizing an FR of human antibody. Primers are prepared for each of the four FR. In general, when grafting mouse CDR to human FR, the selection of a human FR having high identity with mouse FR is considered to be advantageous in terms of maintaining CDR function. Namely, it is generally preferable to use human FR comprising an amino acid sequence having high identity with the amino acid sequence of an FR adjacent to the mouse CDR to be grafted.

In addition, linking nucleotide sequences are designed so as to be connected in-frame. Human FR is individually synthesized by respective primers. As a result, products are obtained in which DNA encoding mouse CDR is added to each FR. Nucleotide sequences encoding mouse CDR of each product are designed to as to mutually overlap. Continuing, the overlapping CDR portions of products synthesized by using human antibody gene as template are mutually annealed followed by carrying out a complementary strand synthesis reaction. Human FR are linked through a mouse CDR sequence by this reaction.

Finally, the 5'-terminal and 3'-terminal of the V region gene, in which three CDR and four FR are linked, are annealed and the entire length thereof is amplified by a primer to which has been added a suitable restriction enzyme recognition sequence. A human antibody expression vector can be produced by inserting DNA obtained in the manner illustrated above and DNA encoding human antibody C region into an expression vector so that they are fused in-frame. After introducing the incorporated vector into host cells to establish recombinant cells, humanized antibody is produced in a culture of cultured cells by culturing the recombinant cells and expressing DNA encoding the humanized antibody (see European Patent Publication No. EP239400 and WO 1996/002576).

Human antibody FR can be preferably selected so that a CDR forms a favorable antigen binding region when linked through the CDR by quantitatively or qualitatively measuring and evaluating binding activity to antigen of humanized antibody produced in the manner illustrated above. Amino acid residues of the FR can also be substituted so that the CDR of reshaped human antibody forms a suitable antigen binding region. For example, an amino acid sequence mutation can be introduced into an FR by applying PCR used to graft mouse CDR to human FR. More specifically, a mutation of a partial nucleotide sequence can be introduced into a primer that is annealed to an FR. The nucleotide sequence mutation is introduced into the FR synthesized by that primer. A variant FR sequence having a desired property can be selected by measuring and evaluating binding activity of the variant antibody in which an amino acid has been substituted to antigen using the above-mentioned method (Cancer Res. (1993) 53, 851-856).

In addition, a desired human antibody can be obtained by DNA immunization by using for the immune animal a transgenic animal having the entire repertoire of human antibody genes (see WO 1993/012227, WO 1992/003918, WO 1994/002602, WO 1994/025585, WO 1996/034096 and WO 1996/033735).

Moreover, a technology is known for obtaining human antibody by panning using a human antibody library. For example, a V region of human antibody is expressed in the form of a single chain antibody (scFv) on the surface of a phage by the phage display method. A phage can be selected that expresses an scFv which binds to an antigen. The DNA sequence encoding the V region of the human antibody which binds to the antigen can be determined by analyzing the genes of the selected phage. After having determining the DNA sequence of the scFv which binds to the antigen, an expression vector can be produced by fusing the V region sequence with the sequence of a desired human antibody C region in-frame followed by inserting into a suitable expression vector. Human antibody is obtained by introducing the expression vector into preferable expressing cells as previously illustrated followed by expressing a gene that encodes the human antibody. These methods are already known (see WO 1992/001047, WO 1992/020791, WO 1993/006213, WO 1993/011236, WO 1993/019172, WO 1995/001438 and WO 1995/015388).

In addition, a B cell cloning technique like that illustrated in Bernasconi et al. (Science (2002) 298, 2199-2202) or WO 2008/081088 (such as the identification and cloning of each antibody encoding sequence, the isolation thereof, and the use thereof for constructing expression vectors for producing each antibody (and particularly IgG1, IgG2, IgG3 or IgG4)) can be suitably used to obtain antibody gene in addition to the above-mentioned methods.

EU Numbering and Kabat Numbering

According to the method used in the present invention, amino acid positions assigned to antibody CDR and FR are defined in accordance with the Kabat numbering system (Sequences of Proteins of Immunological Interest (National Institute of Health, Bethesda, Md., 1987 and 1991). In the present description, amino acids of the variable region of anti-LAMP5 antibody are represented in accordance with the Kabat numbering system while amino acids of the constant region are represented in accordance with the EU numbering system in accordance with the amino acid positions of the Kabat numbering system.

Amino Acid Alteration

Known methods such as site-specific mutagenesis (Kunkel, et al. (Proc. Natl. Acad. Sci. USA (1985) 82, 488-492)) or overlap extension PCR can be suitably employed to alter amino acids in an antibody amino acid sequence. In addition, a plurality of known methods can also be employed as methods for altering amino acids substituted for amino acids other than naturally-occurring amino acids (Annu. Rev. Biophys. Biomol. Struct. (2006) 35, 225-249; Proc. Natl. Acad. Sci. USA (2003) 100(11), 6353-6357). For example, a cell-free translation system (Clover Direct (Protein Express)) and the like are preferable that comprise tRNA in which a non-naturally-occurring amino acid is bound to complementary amber suppressor tRNA of a stop codon in the form of a UAG codon (amber codon).

In the present description, the definition of the term "and/or" used when representing an amino acid alteration site includes all combinations in which "and" and "or" are suitably combined. More specifically, "substitution of the amino acid at position 33, position 55 and/or position 96" includes the following amino acid alteration variations:

(a) position 33, (b) position 55, (c) position 96, (d) position 33 and position 55, (e) position 33 and position 96, (f) position 55 and position 96 and (g) position 33, position 55 and position 96.

Cytotoxic Activity

The antibody used in the present invention is preferably an antibody having cytotoxic activity.

Examples of cytotoxic activity in the present invention include antibody-dependent cell-mediated cytotoxicity (ADCC) activity and complement-dependent cytotoxicity (CDC) activity. In the present invention, CDC activity refers to cytotoxicity induced by the complement system. On the other hand, ADCC activity refers to activity that imparts toxicity to a target cell as a result of Fcγ receptor-retaining cells (such as immune cells) binding to the Fc portion of the target cell through Fcγ receptors when a specific antibody has adhered to a cell surface antigen of the target cell.

Whether or not anti-LAMP5 antibody has ADCC activity or whether or not anti-LAMP5 antibody has CDC activity can be measured using a known method (such as that illustrated in Current Protocols in Immunology, Chapter 7, Immunologic studies in humans, editors, John E. Coligan, et al., John Wiley & Sons, Inc. (1993)).

More specifically, effector cells, complement solution and target cells are first prepared.

(1) Preparation of Effector Cells

The spleen is excised from a CBA/N mouse and the like, and the excised spleen cells are separated in RPMI1640 medium (Invitrogen Corp.). After washing with the same medium comprising 10% fetal bovine serum (FBS, Hyclone Laboratories, Inc.), the cell concentration is adjusted to 5×10/ml to prepare effector cells.

(2) Preparation of Complement Solution

Baby rabbit complement (Cedarlane Laboratories Ltd.) is diluted 10-fold with medium comprising 10% FBS (Invitrogen Corp.) to prepare a complement solution.

(3) Preparation of Target Cells

Cells expressing LAMP5 protein are cultured for 1 hour at 37° C. in DMEM medium comprising 10% FBS together with 0.2 mCi of sodium chromate Cr51 (GE Healthcare Bio-Sciences Corp.) to radioactively label the target cells. Cells transformed with a gene that encodes LAMP5 protein, primary multiple myeloma cells or metastatic multiple myeloma cells can be used for the cells expressing LAMP5 protein. Following radioactive labeling, the cells are washed three times with RPMI1640 medium comprising 10% FBS and cell concentration is adjusted to $2\times10^5$/ml to prepare the target cells.

ADCC activity or CDC activity can be measured according to the methods illustrated below. In the case of measuring ADCC activity, 50 µl aliquots of the target cells and anti-LAMP5 antibody are added to each well of a 96-well round bottom plate (Becton, Dickinson and Company) followed by allowing the plate to stand undisturbed for 15 minutes on ice. Subsequently, 100 µl of effector cells are added to each well followed by incubating the plate for 4 hours in a carbon dioxide gas incubator. The final concentration of antibody can be adjusted to 0 µg/ml or 10 µg/ml. Following incubation, radioactivity in 100 µl of recovered supernatant is measured using a gamma counter (CobraII Auto-Gamma, Model D5005, Packard Instrument Company, Inc.). Cytotoxic activity (%) is calculated using the resulting value based on the calculation formula: $(A-C)/(B-C) \times 100$. A represents the level of radioactivity (cpm) in each sample, B represents the level of radioactivity (cpm) in a sample to which has been added 1% NP-40 (Nacalai Tesque, Inc.), and C represents the level of radioactivity (cpm) in a sample that only comprises the target cells.

On the other hand, in the case of measuring CDC activity, 50 µl aliquots of target cells and anti-LAMP5 antibody are added to each well of a 96-well flat bottom plate (Becton, Dickinson and Company) followed by allowing the plate to stand undisturbed for 15 minutes on ice. Subsequently, 100 µl of complement solution are added to each well followed by incubating the plate for 4 hours in a carbon dioxide gas incubator. The final concentration of antibody is adjusted to 0 µg/ml or 3 µg/ml. Following incubation, radioactivity in 100 µl of recovered supernatant is measured using a gamma counter. Cytotoxic activity is calculated in the same manner as measurement of ADCC activity.

Examples of preferable embodiments of anti-LAMP5 antibody having cytotoxic activity in the present invention include the antibodies illustrated below:

(i) antibody retaining the same CDRs as the D1 antibody illustrated in the examples (antibody comprising a heavy chain variable region comprising the CDR1 defined by SEQ ID NO: 35, the CDR2 defined by SEQ ID NO: 36 and the CDR3 defined by SEQ ID NO: 37 and a light chain variable region comprising the CDR1 defined by SEQ ID NO: 38, the CDR2 defined by SEQ ID NO: 39 and the CDR3 defined by SEQ ID NO: 40);

(ii) antibody retaining the same CDRs as D2 antibody illustrated in the examples (antibody comprising a heavy chain variable region comprising the CDR1 defined by SEQ ID NO: 41, the CDR2 defined by SEQ ID NO: 42 and the CDR3 defined by SEQ ID NO: 43 and a light chain variable region comprising the CDR1 defined by SEQ ID NO: 44, the CDR2 defined by SEQ ID NO: 45 and the CDR3 defined by SEQ ID NO: 46);

(iii) antibody retaining the same CDRs as D10 antibody illustrated in the examples (antibody comprising a heavy chain variable region comprising the CDR1 defined by SEQ ID NO: 53, the CDR2 defined by SEQ ID NO: 54 and the CDR3 defined by SEQ ID NO: 55 and a light chain variable region comprising the CDR1 defined by SEQ ID NO: 56, the CDR2 defined by SEQ ID NO: 57 and the CDR3 defined by SEQ ID NO: 58).

Figure 5:
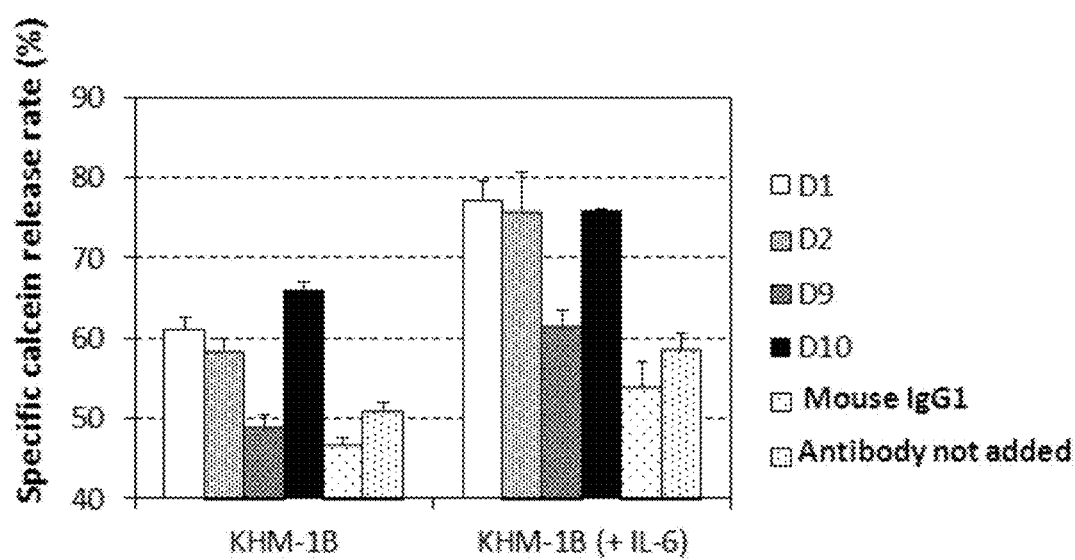
FIG. 5 is a graph illustrating ADCC activity of anti-LAMP5 monoclonal antibodies D1, D2, D9 and D10 against KHM-1B cells (with or without IL-6 stimulation).

As illustrated in Example 6-1, it was shown that clones D1, D2 and D10 may induce ADCC against KHM-1B cells (FIG. 5). In addition, ADCC activity was observed regardless of IL-6 stimulation of KHM-1B cells (FIG. 5).

The calcein release rate of anti-LAMP5 antibody in the present invention according to the evaluation illustrated in Example 6-1 is preferably 50% or more, more preferably 55% or more, even more preferably 60% or more and most preferably 65% or more in the case of the absence of IL-6 stimulation, and preferably 60% or more, more preferably 65% or more, even more preferably 70% or more and most preferably 75% or more in the case of the presence of IL-6 stimulation.

Anti-LAMP5 Antibody Having Enhanced ADCC Activity

Anti-LAMP5 antibody having enhanced ADCC activity can be preferably used for the anti-LAMP5 antibody of the present invention. As was previously illustrated, since ADCC activity refers to activity that imparts toxicity to a target cell as a result of Fcγ receptor-retaining cells (such as immune cells) binding to the Fc portion of the target cell through Fcγ receptors when a specific antibody has adhered to a cell surface antigen of the target cell, by enhancing binding activity of immune cells and other Fcγ receptor-expressing cells to Fcγ receptors, ADCC activity mediated by anti-LAMP5 antibody can be enhanced. At least three known methods illustrated below can be used to enhance binding activity of immune cell and other Fcγ receptor-expressing cells to Fcγ receptors.

(1) Anti-LAMP5 Antibody Having Altered Fc Region Amino Acids

Anti-LAMP5 antibody can be obtained for which binding activity to Fcγ receptors is enhanced by altering the amino acids of an Fc region comprised in the anti-LAMP5 antibody of the present invention. Examples of IgG immunoglobulin Fc regions preferable for alteration include the Fc regions of human IgG (IgG1, IgG2, IgG3 or IgG4 and variants thereof).

With respect to other amino acid alterations, alternation can be made for amino acids at any position, provided binding activity to Fcγ receptors is enhanced. In the case the anti-LAMP5 antibody of the present invention comprises an Fc region of human IgG1 for the human Fc region, in binding to Fcγ receptors an alteration is preferably comprised that demonstrates the effect of further enhancing binding activity of the Fc region obtainable from human IgG1. Examples of amino acid alterations for enhancing binding activity to Fcγ receptors are reported in WO 2007/024249, WO 2007/021841, WO 2006/031370, WO 2000/042072, WO 2004/029207, WO 2004/099249, WO 2006/105338, WO 2007/041635, WO 2008/092117, WO 2005/070963, WO 2006/020114, WO 2006/116260 and WO 2006/023403.

Examples of amino acids capable of being altered as represented with the EU numbering system include at least one amino acid selected from the group of amino acids at position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440. Binding of an Fc region of the anti-LAMP5 antibody of the present invention to Fcγ receptors can be enhanced by these amino acid alterations.

Particularly preferable examples of alterations for use in the present invention when representing an Fc region of the anti-LAMP5 antibody of the present invention with the EU numbering system include alterations of at least one or more amino acids selected from the group consisting of:

Lys or Tyr at position 221;
Phe, Trp, Glu or Tyr at position 222;
Phe, Trp, Glu or Lys at position 223;
Phe, Trp, Glu or Tyr at position 224;
Glu, Lys or Trp at position 225;
Glu, Gly, Lys or Tyr at position 227;
Glu, Gly, Lys or Tyr at position 228;
Ala, Glu, Gly or Tyr at position 230;
Glu, Gly, Lys, Pro or Tyr at position 231;
Glu, Gly, Lys or Tyr at position 232;
Ala, Asp, Phe, Gly, His, Ile, Lys, Leu, Met, Asn, Gln, Arg, Ser, Thr, Val, Trp or Tyr at position 233;
Ala, Asp, Glu, Phe, Gly, His, Ile, Lys, Met, Asn, Pro, Gln, Arg, Ser, Thr, Val, Trp or Tyr at position 234;
Ala, Asp, Glu, Phe, Gly, His, Ile, Lys, Met, Asn, Pro, Gln, Arg, Ser, Thr, Val, Trp or Tyr at position 235;
Ala, Asp, Glu, Phe, His, Ile, Lys, Leu, Met, Asn, Pro, Gln, Arg, Ser, Thr, Val, Trp or Tyr at position 236;
Asp, Glu, Phe, His, Ile, Lys, Leu, Met, Asn, Pro, Gln, Arg, Ser, Thr, Val, Trp or Tyr at position 237;
Asp, Glu, Phe, Gly, His, Ile, Lys, Leu, Met, Asn, Gln, Arg, Ser, Thr, Val, Trp or Tyr at position 238;
Asp, Glu, Phe, Gly, His, Ile, Lys, Leu, Met, Asn, Pro, Gln, Arg, Thr, Val, Trp or Tyr at position 239;
Ala, Ile, Met or Thr at position 240;
Asp, Glu, Leu, Arg, Trp or Tyr at position 241,
Leu, Glu, Leu, Gln, Arg, Trp or Tyr at position 243;
His at position 244;
Ala at position 245;
Asp, Glu, His or Tyr at position 246;
Ala, Phe, Gly, His, Ile, Leu, Met, Thr, Val or Tyr at position 247;
Glu, His, Gln or Tyr at position 249;
Glu or Gln at position 250;
Phe at position 251;
Phe, Met or Tyr at position 254;
Glu, Leu or Tyr at position 255;
Ala, Met or Pro at position 256;
Asp, Glu, His, Ser or Tyr at position 258;
Asp, Glu, His or Tyr at position 260;
Ala, Glu, Phe, Ile or Thr at position 262;
Ala, Ile, Met or Thr at position 263;
Asp, Glu, Phe, Gly, His, Ile, Lys, Leu, Met, Asn, Pro, Gln, Arg, Ser, Thr, Trp or Tyr at position 264;
Ala, Leu, Phe, Gly, His, Ile, Lys, Leu, Met, Asn, Pro, Gln, Arg, Ser, Thr, Val, Trp or Tyr at position 265;
Ala, Ile, Met or Thr at position 266;
Asp, Glu, Phe, His, Ile, Lys, Leu, Met, Asn, Pro, Gln, Arg, Thr, Val, Trp or Tyr at position 267;
Asp, Glu, Phe, Gly, Ile, Lys, Leu, Met, Pro, Gln, Arg, Thr, Val or Trp at position 268;
Phe, Gly, His, Ile, Lys, Leu, Met, Asn, Pro, Arg, Ser, Thr, Val, Trp or Tyr at position 269;
Glu, Phe, Gly, His, Ile, Leu, Met, Pro, Gln, Arg, Ser, Thr, Trp or Tyr at position 270;
Ala, Asp, Glu, Phe, Gly, His, Ile, Lys, Leu, Met, Asn, Gln, Arg, Ser, Thr, Val, Trp or Tyr at position 271;
Asp, Phe, Gly, His, Ile, Lys, Leu, Met, Pro, Arg, Ser, Thr, Val, Trp or Tyr at position 272;
Phe or Ile at position 273;
Asp, Glu, Phe, Gly, His, Ile, Leu, Met, Asn, Pro, Arg, Ser, Thr, Val, Trp or Tyr at position 274;
Leu or Trp at position 275;
Asp, Glu, Phe, Gly, His, Ile, Leu, Met, Pro, Arg, Ser, Thr, Val, Trp or Tyr at position 276;
Asp, Glu, Gly, His, Ile, Lys, Leu, Met, Asn, Pro, Gln, Arg, Ser, Thr, Val, or Trp at position 278;
Ala at position 279;
Ala, Gly, His, Lys, Leu, Pro, Gln, Trp or Tyr at position 280;
Asp, Lys, Pro or Tyr at position 281;
Glu, Gly, Lys, Pro or Tyr at position 282;
Ala, Gly, His, Ile, Lys, Leu, Met, Pro, Arg or Tyr at position 283;
Asp, Glu, Leu, Asn, Thr or Tyr at position 284;
Asp, Glu, Lys, Gln, Trp or Tyr at position 285;
Glu, Gly, Pro or Tyr at position 286;
Asn, Asp, Glu or Tyr at position 288;
Asp, Gly, His, Leu, Asn, Ser, Thr, Trp or Tyr at position 290;
Asp, Glu, Gly, His, Ile, Gln or Thr at position 291;
Ala, Asp, Glu, Pro, Thr or Tyr at position 292;
Phe, Gly, His, Ile, Leu, Met, Asn, Pro, Arg, Ser, Thr, Val, Trp or Tyr at position 293;
Phe, Gly, His, Ile, Lys, Leu, Met, Asn, Pro, Arg, Ser, Thr, Val, Trp or Tyr at position 294;
Asp, Glu, Phe, Gly, His, Ile, Lys, Met, Asn, Pro, Arg, Ser, Thr, Val, Trp or Tyr at position 295;
Ala, Asp, Glu, Gly, His, Ile, Lys, Leu, Met, Asn, Gln, Arg, Ser, Thr, or Val at position 296;
Asp, Glu, Phe, Gly, His, Ile, Lys, Leu, Met, Pro, Gln, Arg, Ser, Thr, Val, Trp or Tyr at position 297;
Ala, Asp, Glu, Phe, His, Ile, Lys, Met, Asn, Gln, Arg, Thr, Val, Trp or Tyr at position 298;
Ala, Asp, Glu, Phe, Gly, His, Ile, Lys, Leu, Met, Asn, Pro, Gln, Arg, Ser, Val, Trp or Tyr at position 299;
Ala, Asp, Glu, Gly, His, Ile, Lys, Leu, Met, Asn, Pro, Gln, Arg, Ser, Thr, Val or Trp at position 300;
Asp, Glu, His or Tyr at position 301;
Ile at position 302;
Asp, Gly or Tyr at position 303;
Asp, His, Leu, Asn or Thr at position 304;
Glu, Ile, Thr or Tyr at position 305;
Ala, Asp, Asn, Thr, Val or Tyr at position 311;
Phe at position 313;
Leu at position 315;
Glu or Gln at position 317;
His, Leu, Asn, Pro, Gln, Arg, Thr, Val or Tyr at position 318;
Asp, Phe, Gly, His, Ile, Leu, Asn, Pro, Ser, Thr, Val, Trp or Tyr at position 320;
Ala, Asp, Phe, Gly, His, Ile, Pro, Ser, Thr, Val, Trp or Tyr at position 322;
Ile at position 323;
Asp, Phe, Gly, His, Ile, Leu, Met, Pro, Arg, Thr, Val, Trp or Tyr at position 324;
Ala, Asp, Glu, Phe, Gly, His, Ile, Lys, Leu, Met, Pro, Gln, Arg, Ser, Thr, Val, Trp or Tyr at position 325;
Ala, Asp, Glu, Gly, Ile, Leu, Met, Asn, Pro, Gln, Ser, Thr, Val, Trp or Tyr at position 326;
Ala, Asp, Glu, Phe, Gly, His, Ile, Lys, Leu, Met, Asn, Pro, Arg, Thr, Val, Trp or Tyr at position 327;
Ala, Asp, Glu, Phe, Gly, His, Ile, Lys, Met, Asn, Pro, Gln, Arg, Ser, Thr, Val, Trp or Tyr at position 328;
Asp, Glu, Phe, Gly, His, Ile, Lys, Leu, Met, Asn, Gln, Arg, Ser, Thr, Val, Trp or Tyr at position 329;
Cys, Glu, Phe, Gly, His, Ile, Lys, Leu, Met, Asn, Pro, Arg, Ser, Thr, Val, Trp or Tyr at position 330;

Asp, Phe, His, Ile, Leu, Met, Gln, Arg, Thr, Val, Trp or Tyr at position 331;
Ala, Asp, Glu, Phe, Gly, His, Lys, Leu, Met, Asn, Pro, Gln, Arg, Ser, Thr, Val, Trp or Tyr at position 332;
Ala, Asp, Glu, Phe, Gly, His, Ile, Leu, Met, Pro, Ser, Thr, Val, or Tyr at position 333;
Ala, Glu, Phe, Ile, Leu, Pro or Thr at position 334;
Asp, Phe, Gly, His, Ile, Leu, Met, Asn, Pro, Arg, Ser, Val, Trp or Tyr at position 335;
Glu, Lys or Tyr at position 336;
Glu, His or Asn at position 337;
Asp, Phe, Gly, Ile, Lys, Met, Asn, Gln, Arg, Ser or Thr at position 339;
Ala or Val at position 376;
Gly or Lys at position 377;
Asp at position 378;
Asn at position 379;
Ala, Asn or Ser at position 380;
Ala or Ile at position 382;
Glu at position 385;
Thr at position 392;
Leu at position 396;
Lys at position 421;
Asn at position 427;
Phe or Leu at position 428;
Met at position 429;
Trp at position 434;
Ile at position 436; and,
Gly, His, Ile, Leu or Tyr at position 440.

In addition, there are no particular limitations on the number of altered amino acids, and an amino acid at only a single location can be altered or amino acids at two or more locations can be altered. Examples of combinations of amino acids altered at two or more locations include the combinations illustrated in Tables 1 and 2.

TABLE 1

| Amino Acid Combination | Amino Acid Combination |
|---|---|
| K370E/P396L/D270E | S239Q/I332Q |
| Q419H/P396L/D270E | S267D/I332E |
| V240A/P396L/D270E | S267E/I332E |
| R255L/P396L/D270E | S267L/A327S |
| R255L/P396L/D270E | S267Q/A327S |
| R255L/P396L/D270E/R292G | S298A/I332E |
| R255L/P396L/D270E | S304T/I332E |
| R255L/P396L/D270E/Y300L | S324G/I332D |
| F243L/D270E/K392N/P396L | S324G/I332E |
| F243L/R255L/D270E/P396L | S324I/I332D |
| F243L/R292P/Y300L/V305I/P396L | S324I/I332E |
| F243L/R292P/Y300L/P396L | T260H/I332E |
| F243L/R292P/Y300L | T335D/I332E |
| F243L/R292P/P396L | V240I/V266I |
| F243L/R292P/V305I | V264I/I332E |
| F243L/R292P | D265F/N297E/I332E |
| S298A/E333A/K334A | D265Y/N297D/I332E |
| E380A/T307A | F243L/V262I/V264W |
| K326M/E333S | N297D/A330Y/I332E |
| K326A/E333A | N297D/T299E/I332E |
| S317A/K353A | N297D/T299F/I332E |
| A327D/I332E | N297D/T299H/I332E |
| A330L/I332E | N297D/T299I/I332E |
| A330Y/I332E | N297D/T299L/I332E |
| E258H/I332E | N297D/T299V/I332E |
| E272H/I332E | P230A/E233D/I332E |
| E272I/N276D | P244H/P245A/P247V |
| E272R/I332E | S239D/A330L/I332E |
| E283H/I332E | S239D/A330Y/I332E |
| E293R/I332E | S239D/H268E/A330Y |
| F241L/V262I | S239D/I332E/A327A |
| F241W/F243W | S239D/I332E/A330I |
| F243L/V264I | S239D/N297D/I332E |

TABLE 1-continued

| Amino Acid Combination | Amino Acid Combination |
|---|---|
| H268D/A330Y | S239D/S298A/I332E |
| H268E/A330Y | S239D/V264I/I332E |
| K246H/I332E | S239E/N297D/I332E |
| L234D/I332E | S239E/V264I/I332E |
| L234E/I332E | S239N/A330L/I332E |
| L234G/I332E | S239N/A330Y/I332E |
| L234I/I332E | S239N/S298A/I332E |
| L234I/L235D | S239Q/V264I/I332E |
| L234Y/I332E | V264E/N297D/I332E |
| L235D/I332E | V264I/A330L/I332E |
| L235E/I332E | V264I/A330Y/I332E |
| L235I/I332E | V264I/S298A/I332E |
| L235S/I332E | Y296D/N297D/I332E |

TABLE 2

| | |
|---|---|
| L328A/I332D | Y296E/N297D/I332E |
| L328D/I332D | Y296H/N297D/I332E |
| L328D/I332E | Y296N/N297D/I332E |
| L328E/I332D | Y296Q/N297D/I332E |
| L328E/I332E | Y296T/N297D/I332E |
| L328F/I332D | D265Y/N297D/T299L/I332E |
| L328F/I332E | F241E/F243Q/V262T/V264E |
| L328H/I332E | F241E/F243R/V262E/V264R |
| L328I/I332D | F241E/F243Y/V262T/V264R |
| L328I/I332E | F241L/F243L/V262I/V264I |
| L328M/I332D | F241R/F243Q/V262T/V264R |
| L328M/I332E | F241S/F243H/V262T/V264T |
| L328N/I332D | F241W/F243W/V262A/V264A |
| L328N/I332E | F241Y/F243Y/V262T/V264T |
| L328Q/I332D | I332E/A330Y/H268E/A327A |
| L328Q/I332E | N297D/I332E/S239D/A330L |
| L328T/I332D | N297D/S298A/A330Y/I332E |
| L328T/I332E | S239D/A330Y/I332E/K326E |
| L328V/I332D | S239D/A330Y/I332E/K326T |
| L328V/I332E | S239D/A330Y/I332E/L234I |
| L328Y/I332D | S239D/A330Y/I332E/L235D |
| L328Y/I332E | S239D/A330Y/I332E/V240I |
| N297D/I332E | S239D/A330Y/I332E/V264T |
| N297E/I332E | S239D/A330Y/I332E/V266I |
| N297S/I332E | S239D/D265F/N297D/I332E |
| P227G/I332E | S239D/D265H/N297D/I332E |
| P230A/E233D | S239D/D265I/N297D/I332E |
| Q295E/I332E | S239D/D265L/N297D/I332E |
| R255Y/I332E | S239D/D265T/N297D/I332E |
| S239D/I332D | S239D/D265V/N297D/I332E |
| S239D/I332E | S239D/D265Y/N297D/I332E |
| S239D/I332N | S239D/I332E/A330Y/A327A |
| S239D/I332Q | S239D/I332E/H268E/A327A |
| S239E/D265G | S239D/I332E/H268E/A330Y |
| S239E/D265N | S239D/N297D/I332E/A330Y |
| S239E/D265Q | S239D/N297D/I332E/K326E |
| S239E/I332D | S239D/N297D/I332E/L235D |
| S239E/I332E | S239D/V264I/A330L/I332E |
| S239E/I332N | S239D/V264I/S298A/I332E |
| S239E/I332Q | S239E/V264I/A330Y/I332E |
| S239N/I332D | F241E/F243Q/V262T/V264E/I332E |
| S239N/I332E | F241E/F243R/V262E/V264R/I332E |
| S239N/I332N | F241E/F243Y/V262T/V264R/I332E |
| S239N/I332Q | F241R/F243Q/V262T/V264R/I332E |
| S239Q/I332D | S239D/I332E/H268E/A330Y/A327A |
| S239Q/I332E | S239E/V264I/S298A/A330Y/I332E |
| S239Q/I332N | F241Y/F243Y/V262T/V264T/N297D/I332E |

In the present description, "enhanced binding activity of an Fc region of anti-LAMP5 antibody to Fcγ receptors" means that binding activity of an Fc region of anti-LAMP5 antibody for which amino acids have been altered as illustrated above to any human Fcγ receptor among FcγRI, FcγRIIa, FcγRIIb, FcγRIIIa and/or FcγRIIIb is higher than the binding activity of an Fc region of anti-LAMP5 antibody prior to amino acids being altered as illustrated above to these human Fcγ receptors. For example, this refers to binding activity such that binding activity of anti-LAMP5 antibody after alteration in comparison with binding activity of anti-LAMP5 antibody prior to alteration serving as a reference is 105% or more, preferably 110% or more, 115% or more, 120% or more, 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, 2 times or more, 2.5 times or more, 3 times or more, 3.5 times or more, 4 times or more, 4.5 times or more, 5 times or more, 7.5 times or more, 10 times or more, 20 times or more, 30 times or more, 40 times or more, 50 times or more, 60 times or more, 70 times or more, 80 times or more, 90 times or more or 100 times or more based on the above-mentioned analysis method.

(2) Anti-LAMP5 Antibody Having Decreased Fucose in Sugar Chain Bound to Fc Region An example of a non-limiting preferable embodiment of the anti-LAMP5 antibody of the present invention is an anti-LAMP5 antibody in which the composition of a sugar chain bound to an Fc region of the anti-LAMP5 antibody is modified so that the ratio of the Fc region bound to a fucose-deficient sugar chain becomes high. Affinity to FcγIIIa is known to be enhanced when a fucose residue is removed from N-acetylglucosamine on an N-glycoside-linked complex sugar chain reducing terminal which binds to antibody Fc region (J. Biol. Chem. (2003) 278, 3466-3473). Since IgG1 antibody comprising such an Fc region is known to demonstrate enhanced ADCC activity as is subsequently illustrated, anti-LAMP5 antibody comprising that Fc region is also useful as the anti-LAMP5 antibody comprised in the pharmaceutical composition of the present invention. An example of a non-limiting preferable embodiment of an antibody in which a fucose residue has been removed from N-acetylglucosamine on the N-glycoside-linked complex sugar chain reducing terminal which binds to an antibody Fc region is a glycosylated antibody (WO 1999/054342).

A different example of a non-limiting preferable embodiment of an antibody in which a fucose residue has been removed from N-acetylglucosamine on the N-glycoside-linked complex sugar chain reducing terminal which binds to antibody Fc region is an antibody deficient in fucose that adds to a sugar chain (WO 2000/061739, WO 2002/031140, WO 2006/067913). As a result of altering the activity for forming a sugar chain structure of a polypeptide subjected to sugar chain modification, host cells having a low ability to add fucose to a sugar chain are used to produce antibodies deficient in fucose added to a sugar chain. Antibody deficient in fucose in the sugar chain thereof can then be recovered from a culture fluid of the host cells by expressing a desired antibody gene in the host cells. Non-limiting preferable examples of activity for forming a sugar chain structure of a polypeptide include activities of the enzymes or transporters selected from the group consisting of fucosyltransferase (EC2.4.1.152), fucose transporter (SLC35C1), GDP-mannose 4,6-dehydratase (GMD) (EC4.2.1.47), GDP-keto-6-deoxymannose 3,5-epimerase-4-reductase (Fx) (EC1.1.1.271) and GDP-β-L-fucose pyrophosphorylase (GFPP) (EC2.7.7.30). The structures of these enzymes or transporters are not necessarily specified provided they are able to demonstrate the activity thereof. In the present description, proteins able to demonstrate these activities are referred to as functional proteins. An example of a non-limiting embodiment of a method for modifying these activities includes loss of that activity. A known method such as a method for disrupting the genes of these functional proteins to make them dysfunctional can be suitably employed to produce host cells in which these activities have been lost (WO 2000/061739, WO 2002/031140, WO 2006/067913). Such host cells that have lost activity can be produced by a method that disrupts the genes of these functional proteins to make them dysfunctional that are intrinsic to such cells as CHO cells, BHK cells, NS0 cells, SP2/0 cells, YO myeloma cells, P3X63 mouse myeloma cells, PER cells, PER.C6 cells or hybridoma cells.

Anti-LAMP5 antibody in which a fucose residue has been removed from N-acetylglucosamine on the N-glycoside-linked complex sugar chain reducing terminal which binds to antibody Fc region can be recovered by recovering from the culture supernatant of the above-mentioned host cells that have been transformed with an expression vector comprising anti-LAMP5 antibody gene.

(3) Anti-LAMP5 Antibody Comprising Fc Region Having Bisecting N-Acetylglucosamine Added Thereto Another example of a non-limiting preferable embodiment of the anti-LAMP5 antibody of the present invention is anti-LAMP5 antibody comprising an Fc region to which bisecting N-acetylglucosamine has been added. Antibodies having a sugar chain comprising a bisecting GlcNAc structure are known (WO 2002/079225). Host cells having activity that forms a sugar chain comprising a bisecting GlcNAc structure are used to produce antibody to which a sugar chain comprising a bisecting GlcNAc structure has been added. In a non-limiting preferable embodiment thereof, host cells are produced that express a gene encoding a functional protein having β-1,4-mannosyl-glycoprotein 4-β-N-acetylglucosaminyltransferase (GnTIII) (EC2.4.1.144) activity or β-1,4-galactosyltransferase (GalT) (EC2.4.1.38) activity. In another non-limiting preferable embodiment, in addition to above-mentioned functional protein, host cells are produced that co-express a gene encoding a functional protein having human mannosidase II (ManII) (3.2.1.114) activity, a gene encoding a functional protein having β-1,2-acetylglucosaminyltransfease I (GnTI) (EC2.4.1.94) activity, a gene encoding a functional protein having β-1,2-acetylglucosaminyltransferase II (GnTII) (EC2.4.1.143) activity, a gene encoding a functional protein having mannosidase (ManI) (EC3.2.1.113) activity and α-1,6-fucosyltransferase (EC2.4.1.68) (WO 2004/065540). Host cells having activity that forms a sugar chain comprising a bisecting GlcNAc structure as illustrated above can be produced by transforming CHO cells, BHK cells, NS0 cells, SP2/0 cells, YO myeloma cells, P3X63 mouse myeloma cells, PER cells, PER.C6 cells or hybridoma cells and the like with an expression vector comprising a gene encoding the above-mentioned functional proteins.

Anti-LAMP5 antibody comprising an Fc region to which has been added bisecting N-acetylglucosamine is recovered by recovering from a culture supernatant of the above-mentioned host cells transformed with an expression vector comprising anti-LAMP5 antibody gene.

Known methods can be used to analyze a sugar chain structure linked to an antibody. In a non-limiting embodiment thereof, a sugar chain binding to anti-LAMP5 antibody is released from a protein by allowing N-glycosidase F (Roche Diagnostics K.K.) to act on the anti-LAMP5 antibody of the present invention (J. Pharm. Sci. (1994) 83(12), 1670-1675). Following a deproteinization procedure using ethanol (J. Clin. Invest. (2001), 108(11), 1687-95), free sugar chain is concentrated and dried to a solid followed by carrying out fluorescent labeling with 2-aminopyridine (Anal. Biochem. (1995) 230(2), 229-238). The resulting 2-AB-labeled sugar chain is removed of reagent by solid phase extraction using a cellulose cartridge followed by concentrating by centrifuging and submitting for subsequent analysis in the form of a purified 2-AB-labeled sugar chain. Next, an agalactosyl 2-AB-labeled sugar chain is prepared by allowing β-galactosidase (SEIKAGAKU CORPORATION) to act on the purified agalactosyl 2-AB-labeled sugar chain. Agalactosyl 2-AB-labeled sugar chain prepared by using as a starting material a sugar chain released from the anti-LAMP5 antibody of the present invention is analyzed by forward phase HPLC using a TSKgel Amide-80 amide column (TOSOH CORPORATION) followed by comparison of the chromatogram thereof.

Antibody Having Internalization Activity

The antibody used in the present invention is preferably antibody that has internalization activity. In the present invention, internalization activity refers to activity by which the antibody of the present invention is incorporated into a cell (into the cytoplasm, vesicles or other organelles) by a mechanism such as endocytosis when the antibody of the present invention has bound to LAMP5 expressed on the cell surface. Whether or not the anti-LAMP5 antibody of the present invention has internalization activity can be confirmed by a person with ordinary skill in the art using a known method. For example, this can be confirmed by a method for confirming whether or not a labeling substance has been incorporated within a cell by contacting anti-LAMP5 antibody linked to a labeling substance with cell expressing LAMP5, or by a method for confirming whether or not cell death has been induced in cells expressing LAMP5 by contacting anti-LAMP5 antibody linked to a cytotoxic substance with cells expressing LAMP5.

Non-limiting preferable examples of cytotoxic substances that demonstrate cytotoxic activity by linking to anti-LAMP5 antibody include chemotherapeutic agents and toxic peptides. Examples of chemotherapeutic agents include azaribine, anastrozole, azacytidine, bleomycin, bortezomib, bryostatin-1, busulfan, camptothecin, 10-hydroxycampothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, maytansinoid, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine and vincristine.

In the present invention, a preferable chemotherapeutic agent is a small molecule chemotherapeutic agent. Small molecule chemotherapeutic agents have little possibility of interfering with antibody function even after binding to an antibody. In the present invention, the small molecular chemotherapeutic agent normally has a molecular weight of 100 to 2000 and preferably 200 to 1000. The chemotherapeutic agents illustrated here are all small molecule chemotherapeutic agents. These chemotherapeutic agents in the present invention include prodrugs that are converted to an active chemotherapeutic agent in the body. Activation of a prodrug can be by enzymatic conversion or non-enzymatic conversion.

In addition, antibody can also be modified with a toxic peptide (toxin). Preferable examples of toxic peptides include Diphtheria Toxin A Chain (Langone, J. J. et al., Methods in Enzymology (1983) 93, 307-308), Pseudomonas Exotoxin (Nature Medicine (1996) 2, 350-353), Ricin A Chain (Fulton, R. J. et al., J. Biol. Chem. (1986) 261, 5314-5319; Sivam, G. et al., Cancer Res. (1987) 47, 3169-3173; Cumber A. J. et al., J. Immunol. Methods (1990) 135, 15-24; Wawrzynczak E. J. et al., Cancer Res. (1990) 50, 7519-7562); Gheeite V. et al., J. Immunol. Methods (1991) 142, 223-230), Deglycosylated RicinA Chain (Thorpe, P. E. et al., Cancer Res. (1987) 47, 5924-5931), Abrin A Chain (Wawrzynczak E. J. et al., Br. J. Cancer (1992) 66, 361-366; Wawrzynczak E. J. et al., Cancer Res. (1990) 50, 7519-7562; Sivam G. et al., Cancer Res (1987) 47, 3169-3173; Thorpe, P. E. et al., Cancer Res. (1987) 47, 5924-5931), Gelonin (Sivam, G. et al., Cancer Res. (1987) 47, 3169-3173; Cumber, A. J. et al., J. Immunol. Methods (1990) 135, 15-24; Wawrzynczak E. J. et al., Cancer Res. (1990) 50, 7519-7562; Bolognesi, A. et al., Clin. Exp. Immunol. (1992) 89, 341-346), Pokeweed anti-viral protein from seeds (PAP-s) (Bolognesi, A. et al., Clin. Exp. Immunol. (1992) 89, 341-346), Briodin (Bolognesi, A. et al., Clin. Exp. Immunol. (1992) 89, 341-346), Saporin (Bolognesi, A. et al., Clin. Exp. Immunol. (1992) 89, 341-346), Momordin (Cumber, A. J. et al., J. Immunol. Methods (1990) 135, 15-24; Wawrzynczak E. J. et al., Cancer Res. (1990) 50, 7519-7562; Bolognesi, A. et al., Clin. Exp. Immunol. (1992) 89, 341-346), Momorcochin (Bolognesi, A. et al., Clin. Exp. Immunol. (1992) 89, 341-346), Dianthin 32 (Bolognesi, A. et al., Clin. Exp. Immunol. (1992) 89, 341-346), Dianthin 30 (Stirpe, F., Barbieri, L., FEBS Letters (1986) 195, 1-8), Modeccin (Stirpe, F., Barbieri, L., FEBS Letters (1986) 195, 1-8), Viscumin (Stirpe, F., Barbieri, L., FEBS Letters (1986) 195, 1-8), Volkesin (Stirpe, F., Barbieri, L., FEBS Letters (1986) 195, 1-8), Dodecandrin (Stirpe, F., Barbieri, L., FEBS Letters (1986) 195, 1-8), Tritin (Stirpe, F., Barbieri, L., FEBS Letters (1986) 195, 1-8), Luffin (Stirpe, F., Barbieri, L., FEBS Letters (1986) 195, 1-8) and Trichokirin (Casellas, P., et al., Eur. J. Biochem. (1988) 176, 581-588; Bolognesi, A., et al., Clin. Exp. Immunol. (1992) 89, 341-346).

In addition, in a different embodiment, antibody can be modified by respectively combining one or two or more small molecule chemotherapeutic agents or toxic peptides. Covalent bonding or non-covalent bonding can be used to link anti-LAMP5 antibody with the above-mentioned small molecule chemotherapeutic agents. Methods for producing antibody linked to these chemotherapeutic agents are known.

Moreover, proteinaceous pharmaceutical agents and toxins can be linked with antibody by genetic engineering techniques. More specifically, a recombinant vector can be constructed that is incorporated in an expression vector by fusing DNA encoding the above-mentioned toxic peptide with DNA encoding anti-LAMP5 antibody in-frame. The incorporated DNA is expressed by introducing the vector into host cells and culturing the resulting transformed cells. In this manner, anti-LAMP5 antibody linked with a toxic peptide can be obtained in the form of a fused protein. In the case of obtaining a protein fused with an antibody, the proteinaceous pharmaceutical agent or toxin is typically linked to the C-terminal side of the antibody. A peptide linker or chemical crosslinking agent can be interposed between the antibody and the proteinaceous pharmaceutical agent or toxin.

An arbitrary sequence can be suitable employed for the amino acid sequence that composes a peptide linker provided it does not impair the binding action of anti-LAMP5 antibody. In the case of a peptide linker, examples of amino acid sequences that can be used include:

```
Ser

Gly·Ser

Gly·Gly·Ser

Ser·Gly·Gly (SEQ ID NO: 74)
Gly·Gly·Gly·Ser (SEQ ID NO: 75)
Ser·Gly·Gly·Gly (SEQ ID NO: 76)
Gly·Gly·Gly·Gly·Ser (SEQ ID NO: 77)
Ser·Gly·Gly·Gly·Gly (SEQ ID NO: 78)
Gly·Gly·Gly·Gly·Gly·Ser (SEQ ID NO: 79)
Ser·Gly·Gly·Gly·Gly·Gly (SEQ ID NO: 80)
Gly·Gly·Gly·Gly·Gly·Gly·Ser (SEQ ID NO: 81)
Ser·Gly·Gly·Gly·Gly·Gly·Gly (Gly·Gly·Gly·Gly·Ser) n (Ser·Gly·Gly·Gly·Gly) n
```

(n represents an integer of 1 or more.)

The amino acid sequence of the peptide linker can be suitably selected by a person with ordinary skill in the art. For example, n, which determines the length of the above-mentioned peptide linkers, is normally 1 to 5, preferably 1 to 3 and more preferably 1 or 2.

Alternatively, anti-LAMP5 antibody and a cytotoxic substance can be linked by using a synthetic chemical linker (chemical crosslinking agent). Crosslinking agents normally used, as represented by a peptide compound, are preferably used in the present invention. For example, the chemical crosslinking agents illustrated below are known. These chemical crosslinking agents are commercially available.

N-hydroxysuccinimide (NHS),
Disuccinimidyl suberate (DSS)
Bis(sulfosuccinimidyl) suberate (BS3)
Dithiobis(succinimidyl propionate) (DSP)
Dithiobis(sulfosuccinimidyl propionate) (DTSSP)
Ethylene glycol bis(succinimidyl succinate) (EGS)
Ethylene glycol bis(sulfosuccinimidyl succinate) (Sulfo-EGS)
Disuccinimidyl tartrate (DST),
Disulfosuccinimidyl tartrate (Sulfo-DST),
Bis[2-(succinimidooxycarbonyloxy)ethyl]sulfone (BSOCOES), and
Bis[2-(sulfosuccinimidooxycarbonyloxy)ethyl]sulfone (Sulfo-BSOCOES), and others Pharmaceutical Composition In another aspect, the present invention provides a pharmaceutical composition comprising the anti-LAMP5 antibody of the present invention as an active ingredient thereof. In addition, the present invention relates to a cell growth inhibitor (and particularly an anticancer drug) comprising the anti-LAMP5 antibody of the present invention as an active ingredient thereof. The cell growth inhibitor (and particular, an anticancer drug) of the present invention is preferably administered to a subject that is affected by cancer or has the potential for being affected by cancer.

In the present invention, the cell growth inhibitor comprising anti-LAMP5 antibody as an active ingredient thereof can also be expressed as a method for inhibiting cell growth that includes a step for administering anti-LAMP5 antibody to a subject, or the use of anti-LAMP5 antibody in the production of a cell growth inhibitor.

In addition, in the present invention, an anticancer drug comprising anti-LAMP5 antibody as an active ingredient thereof can also be expressed as a method for preventing or treating cancer that includes a step for administering anti-LAMP5 antibody to a subject, or the use of anti-LAMP5 antibody in the production of an anticancer drug.

In the present invention, comprising anti-LAMP5 antibody as an active ingredient thereof means that anti-LAMP5 antibody is comprised as the principal active ingredient and does not limit the content of anti-LAMP5 antibody. There are no particular limitations on the antibody comprised in the pharmaceutical composition of the present invention (such as a cell growth inhibitor and particularly an anticancer drug, to apply similarly hereinafter) provided it binds to LAMP5 protein, and examples thereof include the antibodies illustrated in the present description.

The anti-LAMP5 antibody of the present invention can be used in combination with IL-6 (for example, the polypeptide represented by SEQ ID NO: 67) or a fragment, variant, fused protein, functional derivative or salt thereof. The anti-LAMP5 antibody and IL-6 or fragment, variant, fused protein, functional derivative or salt thereof can be used in combination either simultaneously, separately or sequentially in the treatment of cancer. In the present invention, the anti-LAMP5 antibody and IL-6 or fragment, variant, fused protein, functional derivative or salt thereof can be provided in the form of a compound drug in which both are in combination. In addition, a pharmaceutical agent comprising anti-LAMP5 antibody and a pharmaceutical agent comprising IL-6 or a fragment, variant, fused protein, functional derivative or salt thereof can be supplied separately and these pharmaceutical agents can be used simultaneously, separately or sequentially. Moreover, a pharmaceutical agent comprising anti-LAMP5 antibody and a pharmaceutical agent comprising IL-6 or a fragment, variant, fused protein, functional derivative or salt thereof can also be provided in the form of a kit composed thereof. In the case of using separately or sequentially, although there are no limitations on the time interval at which they are used, IL-6 or a fragment, variant, fused protein, functional derivative or salt thereof is preferably used prior to using anti-LAMP5 antibody. The time interval can be suitably set by a person with ordinary skill in the art.

IL-6 is a multifunctional cytokine produced and secreted by several types of cell types. This multifaceted cytokine plays a central role in the cell defense mechanism, including immune response, acute phase response and hematopoiesis. IL-6 is a 20 kDa to 26 kDa glycoprotein having 185 amino acids that has already been cloned. IL-6 has been previously referred to as B-cell stimulating factor 2 (BSF-2), interferon beta 2 and hepatocyte stimulating factor. IL-6 is secreted by a various types of tissues, including the liver, spleen and bone marrow, and by a diverse range of cell types, including monocytes, fibroblasts, endothelial cells, B cells and T cells. IL-6 is activated at the transcription level by various types of signals, including viruses, double-stranded RNA, bacteria and bacterial lipopolysaccharides, and inflammatory cytokines such as IL-1 and TNF.

The biological activity of IL-6 is mediated by a membrane receptor system comprising two types of proteins, with one being referred to as IL-6 receptor (or gp80) and the other referred to as gp130. gp130 is a transmembrane protein having an amino acid length of 918 amino acids that comprises an intracellular domain consisting of 277 amino acids, and is a subunit component of a plurality of cytokine receptors that include IL-6, IL-11, LIF, oligostatin M, ciliary neurotrophic factor (CNTF) and CT-1 receptors. IL-6 is a prototype of cytokine that acts through gp130, and this cytokine family is also referred to as "IL-6-type cytokines".

gp130 is involved in the formation of high-affinity receptors of the above-mentioned cytokines by binding to low-affinity receptor chains. Thus, gp130 is referred to as an "affinity converter". A ligand which binds to a cytokine receptor brings about dimerization of gp130 (in the case of IL-6 receptors) or heterodimerization with a gp130-related protein known as LIFR beta subunit (in the case of LIF, oncostatin M and CNTF receptors). Binding of individual ligands is accompanied by activation/association of a member of the tyrosine kinase family known as Janus kinase (JAK) in the initial step of intracellular signal transduction. The intracellular signal transduction process includes a tyrosine phosphorylation reaction and activating factors referred to as STATs (signal transducer and activator of transcription).

Human gp130 gene is thought to be positioned as a gene homologous to two different chromosomal loci on chromosomes 5 and 17. The existence of two different gp130 gene sequences is limited to primates and is not observed in other vertebrates.

The signal transmission activity of IL-6, IL-11, CNTF, oncostatin M and LIF can be interrupted by various types of monoclonal antibodies which bind to gp130 in particular. In addition, the existence of monoclonal antibodies that activate gp130 directly has also been observed irrespective of the presence of cytokines or receptors thereof.

Other gp130-directed monoclonal antibodies are known to inhibit the mediator function of IL-6. Soluble gp130 (sgp130) having molecular weights of 90 kDa and 110 kDa is observed in human serum. These, along with gp130 as a component thereof, are able to inhibit the biological functions of these cytokines that use a receptor system.

The soluble form of IL-6R (soluble IL-6R) corresponding to the extracellular domain of IL-6R is natural product of the body that is observed in the form of a glycoprotein in blood and urine. One of the exceptional characteristics of sIL-6R molecules is that they have a large number of cell types, including human cells, and act as potent agonists of IL-6. Despite the absence of the intracytoplasmic domain of IL-6R, sIL-6R is able to induce dimerization of gp130 by reacting with IL-6 and further mediates subsequent IL-6-specific signal transmission and biological effects. sIL-6R has two types of interaction with gp130 that are essential for IL-6-specific biological activity, and an activated IL-6 receptor complex has been advocated that consists of a hexamer structure formed by two gp130 chains, two IL-6R and two IL-6 ligands.

The circulating concentration of sIL-6R (agonist) in normal subjects is comparatively high and is comparable to the circulating concentration of 10 ng/ml of the above-mentioned soluble gp130 (natural IL-6 antagonist) (Corbi, et al., Eur. J. Cardiotherac. Surg. (2000) 18(1), 98-103). In contrast, the circulating concentration of IL-6 is low at about 10 pg/ml or lower (Kado, et al., Acta Diabetol. (1999) (1-2), 67-72). In this manner, there are cases in which the effect of IL-6 in the case of administering to patients in vivo alone without concomitant administration of sIL-6R is effective and cases in which it is ineffective, and varies according to the concentrations of soluble agonist and antagonist of a specific disease and at a specific site in the body.

A chimeric molecule which binds sIL-6R and IL-6 has been developed (Chebath, et al., Eur. Cytokine Netw. (1997) (4), 359-365), and has been named "IL-6R/IL-6". IL-6R/IL-6 is formed by fusing the entire encoding regions of cDNA encoding sIL-6R and IL-6 (see FIG. 4). Recombinant IL-6R/IL-6 has been produced in CHO cells (Chebath, et al., WO 1999/002552). IL-6R/IL-6 binds to the gp130 chain in vivo at higher efficiency than a mixture of sIL-6R and IL-6 (Kollet, et al., Blood (1999) 94(3), 923-31). Molecules in the manner of IL-6R/IL-6, for example, are included in the variants, fused protein and functional derivatives of IL-6 of the present invention.

The "IL-6R/IL-6" used in the present invention is a chimeric molecule having the soluble portion of gp80 fused to the entirety of IL-6 or the biologically active fraction thereof. This portion of the chimeric molecule can be mutually fused directly or fused by disulfide crosslinking or an arbitrary suitable linker such as a polypeptide linker. The linker is a short linker peptide and may be as short as 1 to 3 amino acid residues or may be as comparatively long as 13 to 18 amino acid residues. The linker may be, for example, a tripeptide in the manner of E-F-M (Glu-Phe-Met) or a peptide consisting of 13 amino acids in the manner of Glu-Phe-Gly-Ala-Gly-Leu-Val-Leu-Gly-Gly-Gln-Phe-Met that is introduced between the amino acid sequence of sIL-6R and the amino acid sequence of IL-6. Examples of IL-6R/IL-6 are widely known in the art and are illustrated in detail in WO 1999/02552 or WO 1997/32891.

The term "variant" used in the present invention represents an analogue of IL-6 or IL-6R/IL-6 such that one or more amino acid residues of naturally-occurring components of IL-6 or IL-6R/IL-6 are substituted with a different amino acid residue or deleted, or one or more amino acid residues are added to the original sequence of IL-6 or IL-6R/IL-6 without causing a significant change in the biological activity of the original IL-6 or IL-6R/IL-6. These variants are produced according to a previously known synthesis method and/or site-specific mutagenesis technique or other preferable known art.

A variant according to the present invention comprises a protein encoded by a nucleic acid (such as DNA or RNA) that hybridizes with a complementary strand of a nucleic acid (such as DNA or RNA) that encodes IL-6 or IL-6R/IL-6 under moderately stringent conditions or stringent conditions. The term "stringent conditions" represents hybridization and subsequent washing conditions conventionally expressed as "stringent" by a person with ordinary skill in the art. Refer to Ausubel, et al. (Current Protocols in Molecular Biology, Supra, Interscience, N.Y., §§6.3 and 6.4 (1987, 1992) and Sambrook, et al. (Sambrook, J. C., Fritsch, E. F. and Maniatis, T. (1989) Molecular Cloning: A Laboratory Manual, Cold Spring Harbor Laboratory Press, Cold Spring Harbor, N.Y.).

In a non-limiting embodiment, an example of stringent conditions includes washing conditions at a temperature 12° C. to 20° C. lower than the calculated Tm value of the test hybrid such as for 5 minutes in 2×SSC and 0.5% SDS, 15 minutes in 2×SSC and 0.1% SDS, 30 minutes to 60 minutes at 37° C. in 0.1×SSC and 0.5% SDS, and finally 30 minutes to 60 minutes at 68° C. in 0.1×SSC and 0.5% SDS. It is understood by a person with ordinary skill in the art that stringent conditions vary according to the DNA sequence, oligonucleotide probe length (such as 10 to 40 bases) or the length of the mixed nucleotide probe. In the case of using a mixed probe, tetramethyl ammonium chloride (TMAC) is preferably used instead of SSC (refer to the above-mentioned Ausubel, et al.). "Moderately stringent conditions" refer to washing conditions at a lower temperature or lower salt or detergent conditions, such as in the case of 42° C. in 0.2×SSC and 0.1% SDS. (Refer to Ausubel, et al. above.)

Such variants preferably have an amino acid sequence that is substantially similar or adequately duplicates the sequence of IL-6 or IL-6R/IL-6 so as to have favorable activity in comparison with IL-6 or IL-6R/IL-6.

A characteristic activity of IL-6 is the ability to bind to IL-6R (gp80 element), and a characteristic activity of IL-6R/IL-6 is the ability to bind to gp130. ELISA for measuring binding of IL-6R/IL-6 to gp130 is explained in detail in WO 1999/02552, the contents of which are completely incorporated in the present description by reference. A variant can be considered to be provided with activity similar to that of IL-6 or IL-6R/IL-6 provided it demonstrates substantial binding activity to the individual binding regions of IL-6R or gp130. Thus, as is illustrated in WO 1999/02552, an evaluation can be made as to whether a given variant is provided at least substantially with the same activity as IL-6 or IL-6R/IL-6 by a routine experimental means comprising applying to such a variant a simple sandwich binding test for judging whether or not the variant binds to immobilized IL-6R or gp130.

For example, a 96-well microtiter plate (Nunc Inc.) is first coated with anti-human IL-6R monoclonal antibody followed by the addition of 50 ng/ml of IL-6R (both available from R&D Systems Inc.). After washing with phosphate-buffered physiological saline, IL-6 is applied to each well at various concentrations within the range of 0.1 ng/ml to 50 ng/ml. After incubating overnight at 40° C., rabbit polyclonal anti-IL-6 antibody is added followed by the addition of goat anti-rabbit Ig bound to horseradish peroxidase that is detected by a coloring reaction (Sigma-Aldrich Co. LLC.). After incubating and washing, a chromogenic substrate corresponding to horseradish peroxidase (such as 3,3',5,5'-tetramethylbenzidine (TMB)) is added followed by measuring absorbance and the like to evaluate activity at which IL-6 binds to the immobilized IL-6R.

In a preferred embodiment, all such variants have identity or homology of at least 40% with the sequence of the mature IL-6 or IL-6R/IL-6 chimeric molecules included in WO 1999/02552. All such variants have identity or homology of more preferably at least 50%, at least 60%, at least 70% or at least 80%, and most preferably at least 90%.

Identity reflects the relationship between two or more polypeptide sequences or two or more polynucleotide sequences determined by a comparison thereof. In general, identity refers to the correct matching between nucleotides and nucleotides or between amino acids and amino acids of two polynucleotide sequences or two polypeptide sequences, respectively, over the entire length of the compared sequences.

A certain percentage of identity can be determined for those sequences that do not correctly match. In general, two sequences to be compared are aligned so as to obtain the maximum correlation between the sequences. This includes the insertion of gaps in any one or both of the sequences in order to enhance the degree of alignment. The percentage of identity may be determined over the entire length of compared sequence (so-called global alignment) or may be determined over a shorter defined length (so-called local alignment). Global alignment is particularly suitable for sequences having identical or extremely similar lengths, while local alignment is more suitable for sequences having unequal lengths.

Methods for comparing the identity and homology of two or a larger number of sequences are known in the art. Thus, a program able to be used with the Wisconsin Sequence Analysis Package, Version 9.1 (Devereux, J., et al., 1984), such as the BESTFIT or GAP program, can be used to determine the percentage of identity between two polynucleotides or the percentage of identity and percentage of homology between two polypeptides. BESTFIT uses the "local homology" algorithm developed by Smith and Waterman (1991) and is used to find a single region of optimum homology between two sequences. Other programs for determining identity and/or homology between sequences are also known by persons with ordinary skill in the art, examples of which include the BLAST family of programs (accessible from the web site of NCBI at ncbi.nlm.nih.gov) and FASTA.

Chimeric variants of IL-6 or IL-6R/IL-6, or nucleic acids encoding the same, able to be used according to the present invention include a finite number of substantially corresponding sequences in the form of substituted peptides or nucleotides able to be routinely obtained by persons with ordinary skill in the art without excessive experimentation based on the teachings and guidelines expressed in the present description.

"Conservative substitutions" are known to be preferable changes in a variant according to the present invention. Conservative amino acid substitutions of IL-6 or IL-6R/IL-6 chimera can include synonymous amino acids within the range of a group of amino acids having sufficiently similar physicochemical properties, and substitutions among members of that group most likely to preserve the biological function of molecules. In the case of only a comprising a small number of 30 or fewer, and preferably 10 or fewer, insertions or deletions of amino acids in particular, such as when not deleting or substituting an important amino acid in the functional conformation such as a cysteine residue, amino acid insertion and deletion clearly occurs within the above-mentioned sequence without causing a change in the function thereof. Proteins and variants thereof produced as a result of such deletions and/or insertions are within the scope of the present invention. Conservative amino acid substitution is widely known by persons with ordinary skill in the art.

Production examples of amino acid substitutions at the protein level that can be used to obtain an IL-6 or IL-6R/IL-6 chimeric mutein for use in the present invention include known methods and procedures illustrated in U.S. Pat. No. 4,959,314, U.S. Pat. No. 4,588,585 and U.S. Pat. No. 4,737,462 by Mark, et al., U.S. Pat. No. 5,116,943 by Koths, et al., U.S. Pat. No. 4,965,195 by Namen, et al., U.S. Pat. No. 4,879,111 by Chong, et al. and U.S. Pat. No. 5,017,691 by Lee, et al., and lysine-substituted proteins illustrated in U.S. Pat. No. 4,904,584 (Shaw, et al.).

There are also illustrations regarding specific variants of IL-6 used in relation to the present invention (WO 1994/03492). Moreover, European Patent No. 667872(B1) illustrates mutant IL-6 having improved biological activity in comparison with wild type IL-6. In addition, European Patent No. 656117(B1) illustrates a method for isolating an IL-6 superantagonist. A mutant or superantagonist may be used in accordance with the present invention.

The term "fused protein" refers to a polypeptide composed of IL-6, IL6R/IL-6 or a variant or fragment thereof that is fused with another protein having a long retention time in body fluid, for example. Thus, IL-6 or IL6R/IL-6 can be, for example, fused with other proteins or polypeptides in the manner of immunoglobulin or a fragment thereof.

In the case of using in the present description, a "functional derivative" includes derivatives, or variants and fused proteins thereof, of IL-6 or IL-6R/IL-6 chimera able to be produced from a functional group present as a side chain, N-terminal or C-terminal of a residue using a method known in the art, and provided they are pharmacologically acceptable, namely provided they do not disrupt the activity of proteins substantially similar to the activity of IL-6 or IL-6R/IL-6 and do not impart toxicity in a composition comprising the same, are included in the present invention.

Examples of these derivatives include polyethylene glycol side chains able to block an antigen region and prolong the retention time of IL-6R/IL-6 in body fluid. Other examples of derivatives include aliphatic esters of a carboxyl group, amides of an aminoxyl group obtained by reacting with ammonia, primary amine or secondary amine, N-acyl derivatives of a free amino group of amino acid residues formed together with an acrylic component (such as an alkanoyl group or carbocyclic alloyl group), and O-acyl derivatives of a free hydroxyl group formed together with an acyl component (such as derivatives of seryl residue or threonyl residue).

A "fragment" according to the present invention may be, for example, an active fragment of IL-6 or IL-6R/IL-6. The term "fragment" represents any subunit of a molecule, or in other words, a short peptide retaining a desired biological activity that has the activity of a gp130 agonist. A fragment can be immediately produced by removing an amino acid from either terminal of IL-6 or IL-6R/IL-6, testing for a property thereof with the remaining fragment, and respectively binding to IL-6R or gp130. Proteases for removing a single amino acid in a single step from either the N-terminal or C-terminal of a polypeptide are well known in the art, and therefore an ordinary experiment can be easily carried out in order to assess a fragment retaining a desired biological activity.

The fragment of IL-6 or IL-6R/IL-6, or variant or fused protein thereof, can be in a form in which it is also present with a protein per se or an accessory molecule. In addition, a sugar residue, phosphate residue or protein molecule can be in a form in which it is linked to that residue. In addition, a protein molecule or sugar residue moiety thereof can be in a form in which it forms an aggregate. Any of these forms can be included in the fragment of IL-6 or IL-6R/IL-6 of the present invention, or variant or fused protein thereof, provided it exhibits agonistic activity on gp130.

The term "salt" in the present description represents both a salt of a carboxyl group and an acid addition salt of an amino group of IL-6 or IL-6R/IL-6 or analogue thereof. A salt of a carboxyl group can be formed by a known means in the art, and examples thereof include inorganic salts such as sodium salts, calcium salts, ferric salts or zinc salts, and salts having an organic base in the form of a base formed with an amine such as triethanolamine, arginine, lysine, piperidine or procaine. Examples of acid addition salts include salts having an inorganic acid such as hydrochloric acid or sulfuric acid and salts having an organic acid such as acetic acid or oxalic acid. Naturally, any such salts are required to retain biological activity of IL-6 or IL-6R/IL-6, or in other words, the ability to transmit signals through gp130.

In a preferable embodiment of the present invention, the IL-6 of the present invention, or a fragment, variant, fused protein or salt thereof, is glycosylated at one or more sites.

The glycosylated form of IL-6R/IL-6 is extremely preferably a chimeric molecule according to the present invention and is illustrated in WO 1999/02552. The IL-6R/IL-6 illustrated in the present description is a recombinant glycoprotein of human origin obtained by fusing the entire encoding sequence of naturally-occurring soluble IL-6 receptor δ-Val to the entire encoding sequence of mature, naturally-occurring IL-6. A person with ordinary skill in the art is able to produce glycosylated IL-6 by a recombinant means, namely by expressing in a eukaryotic expression system.

According to the present invention, an agonist can be produced in suitable eukaryotic or prokaryotic cell types such as yeast cells, insect cells or bacteria. Although the agonist is preferably produced in mammalian cells, as is illustrated with respect to IL-6R/IL-6 in WO 1999/02552, it is most preferably produced in gene recombinant CHO cells. Although human-obtainable protein is preferable, a person with ordinary skill in the art would understand that any other similar fused protein of biological origin can also be used according to the present invention provided it retains the biological activity illustrated in the present description.

In another embodiment of the present invention, the IL-6 of the present invention, or fragment, variant, fused protein or salt thereof, is not glycosylated. In this case, although chimeric molecules do not synthesize a glycosyl residue, since they can normally be produced in bacterial cells provided with the ability to produce a high yield of produced recombinant protein, they are favorable for use. The production of non-glycosylated IL-6 is illustrated in detail, for example, in the specification of European Patent No. 504751 (B1).

In still another embodiment, the IL-6 of the present invention, or fragment, variant, fused protein or salt thereof, includes a fused immunoglobulin, or in other words, a molecule according to the present invention is fused to an entire immunoglobulin or portion thereof, and particularly to an Fc fragment of an immunoglobulin. Methods for producing immunoglobulin are well known in the art, and an example thereof is illustrated in WO 2001/03737. A person with ordinary skill in the art would understand that a fused protein produced in the present invention has the biological activity of IL-6 or IL-6R/IL-6 (namely retains the ability to stimulate gp130 signal transmission). The produced fused protein ideally has improved properties such as prolonging retention time (half-life) in body fluid, increasing specific activity, improving expression level or promoting purification of fused protein.

The IL-6 of the present invention, or fragment, variant, fused protein or salt thereof is preferably fused to a constant region of an Ig molecule. It may also be fused to a heavy chain region such as CH2 or CH3 of human IgG1. IgG2 or IgG4 isomers, IgM or IgA isomers, other Ig molecule subunits or other isomers of Ig molecules are also preferable for producing fused protein according to the present invention. Thus, the fused protein may be any of a monomer, multimer, heteromultimer or homomultimer.

The properties of proteins, such as stability, half-life, bioavailability, human tolerance or immunogenicity, can be improved by comprising the IL-6 of the present invention, or a fragment, variant, fused protein or salt thereof, in a polymer.

Thus, a preferable embodiment of the present invention relates to a functional derivative of the IL-6 of the present invention, or a fragment, variant, fused protein or salt thereof, which has at least one portion thereof that is bound to one or more functional groups present in one or more side chains of an amino acid residue.

A particularly preferable aspect of the present invention relates to the IL-6 according to the present invention, or a fragment, variant, fused protein or salt thereof, that is bound to polyethylene glycol (PEG). Binding to polyethylene glycol may be carried out by a commonly known method such as the method illustrated in WO 1992/13095.

The pharmaceutical composition of the present invention can be administered to a patient by either oral or parenteral administration. Parenteral administration is preferable. Specific examples of parenteral administration include injection administration, transnasal administration, transpulmonary administration and transcutaneous administration. Examples of injection administration include intravenous injection, intramuscular injection, intraperitoneal injection and subcutaneous injection, and the pharmaceutical composition of the present invention can be administered systemically or locally. In addition, the administration method can be suitably selected according to patient age and symptoms. The dosage can be selected within a range of, for example, 0.0001 mg to 1000 mg per 1 kg of body weight per administration. Alternatively, the dosage can be selected within the range of 0.001 mg to 100000 mg per patient. However, the dosage of the pharmaceutical composition of the present invention is not limited thereto.

The pharmaceutical composition of the present invention can be prepared in accordance with ordinary methods (such as illustrated in Remington's Pharmaceutical Science, Latest edition, Mark Publishing Company, Easton, U.S.A.), and may also comprise pharmacologically acceptable carriers and additives. Examples of pharmacologically acceptable carriers and additives include surfactants, vehicles, colorants, fragrances, preservatives, stabilizers, buffers, suspending agents, isotonic agents, binders, disintegrating agents, lubricants, fluidity improvers and taste masking agents. The pharmacologically acceptable carriers and additives are not limited thereto, but rather other ordinarily used carriers and additives can also be suitably used. More specifically, examples of carriers include light silicic anhydride, lactic acid, crystalline cellulose, mannitol, starch, carmellose calcium, carmellose sodium, hydroxypropyl cellulose, hydroxypropyl methyl cellulose, polyvinyl acetal diethylaminoacetate, polyvinylpyrrolidone, gelatin, medium chain fatty acids and triglycerides, polyoxyethylene hydrogenated castor oil 60, sucrose, carboxymethyl cellulose, cornstarch and inorganic salts.

Anti-LAMP5 antibody is an antibody which binds to LAMP5 protein comprised in the pharmaceutical composition of the present invention (such as a cell growth inhibitor and particularly an anticancer drug) as previously illustrated. There are no particular limitations on the cells which bind to the anti-LAMP5 antibody provided they are cells that express LAMP5. Preferable LAMP5-expressing cells in the present invention are cancer cells and more preferably multiple myeloma cells. The method of the present invention can be applied to these cancers, a primary lesion thereof or a metastatic lesion thereof. More preferably, the cancer cells are primary multiple myeloma cells and metastatic multiple myeloma cells.

In the present invention, "contact" is carried out by, for example, adding antibody to a culture fluid of LAMP5-expressing cells cultured in vitro. In this case, the added antibody can be suitably used in the form of a solution or solid obtained by freeze-drying and the like. In the case of adding in the form of a solution, the solution may be an aqueous solution simply comprising only the antibody or may be a solution comprising, for example, the above-mentioned surfactants, vehicles, colorants, fragrances, preservatives, stabilizers, buffers, suspending agents, isotonic agents, binders, disintegrating agents, lubricants, fluidity improvers or taste masking agents. Although there are no particular limitations on the concentration at which the antibody is added, it is preferably within the range of 1 pg/ml to 1 g/ml, more preferably within the range of 1 ng/ml to 1 mg/ml, and even more preferably within the range of 1 µg/ml to 1 mg/ml as the final concentration in the culture fluid.

In addition, in the present invention, "contact" is further carried out in a different manner by administering to a non-human animal to which LAMP5-expressing cells (such as cancer cells) have been grafted into the body thereof or an animal intrinsically having LAMP5-expressing cells (such as cancer cells) in the body thereof. Oral administration or parenteral administration can be used for the administration method. Administration by parenteral administration is particularly preferable and specific examples thereof include injection administration, transnasal administration, transpulmonary administration and transcutaneous administration. Examples of injection administration include intravenous injection, intramuscular injection, intraperitoneal injection and subcutaneous injection, and the pharmaceutical composition of the present invention (for example, a cell growth inhibitor such as an anticancer drug) can be administered systemically or locally. In addition, the administration method can be suitably selected according to the age and symptoms of the test animal. In the case of administering in the form of an aqueous solution, an aqueous solution may be used that simply comprises antibody only, or may be a solution comprising, for example, the above-mentioned surfactants, vehicles, colorants, fragrances, preservatives, stabilizers, buffers, suspending agents, isotonic agents, binders, disintegrating agents, lubricants, fluidity improvers or taste masking agents. The dosage can be selected within a range of, for example, 0.0001 mg to 1000 mg per 1 kg of body weight per administration. Alternatively, the dosage can be selected within the range of 0.001 mg to 100000 mg per patient. However, the antibody dosage of the present invention is not limited to these dosages.

EXAMPLES

Although the following provides a more detailed explanation of the present invention according to examples thereof, the present invention is not limited to these examples.

(Example 1) Expression Analysis of LAMP5 Using Microarray

When expression of LAMP5 in multiple myeloma clinical specimens was examined using the publicly available microarray data set GSE26760, expression of LAMP5

(probe ID: 219463 at) was observed in many of the specimens (FIG. 1). Furthermore, this data set was obtained by purifying CD138-positive myeloma cells obtained from multiple myeloma patients, and microarray analysis was carried out using the Human Genome U133 Plus 2.0 Array (Affymetrix, Inc.) (Initial genome sequencing and analysis of multiple myeloma, Nature (2011) 471:467-72).

(Example 2) Production of Monoclonal Antibody to LAMP5

2-1. Production of LAMP5 Expression Vector cDNA was produced from total RNA, prepared from cancer cell line U-937 (JCRB Cell Bank) using Trizol (Invitrogen Corp.), using SuperScript III Reverse Transcriptase (Invitrogen Corp.). LAMP5 gene amplified by PCR using this cDNA as template and using a forward primer (LAMP5-F, SEQ ID NO: 1) and reverse primer (LAMP5-R, SEQ ID NO: 2) was cloned in pCR2.1-TOPO vector (Invitrogen Corp.) (pCR2.1 LAMP5). The sequence inserted into pCR2.1 LAMP5 was analyzed and confirmed to be the same as the sequence of NCBI reference sequence NM 012261.

Next, in order to produce an expression vector inserted with an HA tag sequence (amino acid sequence: YPYDVP-DYA (SEQ ID NO:82)) immediately under the signal sequence of LAMP5 (amino acid nos. 1 to 29), the signal sequence portion was amplified by PCR using a forward primer having an EcoRI site and Kozak sequence (Eco-Kozak-LAMP5-F, SEQ ID NO: 3) and a reverse primer having an HA tag sequence (HAtag-LAMP5-R, SEQ ID NO: 4), while the portion other than the signal sequence was amplified by PCR using 15 a forward primer having an HA tag sequence (HAtag-LAMP5-F, SEQ ID NO: 5) and a reverse primer having an NotI site (LAMP5-Not-R, SEQ ID NO: 6). pCR2.1 LAMP5 was used as template. A PCR amplification product further amplified using Eco-Kozak-LAMP5-F and LAMP5-Not-R by using an annealed product of the resulting two amplification products was cloned in pCR2.1-TOPO vector (pCR2.1 HA-LAMP5). Continuing, an insertion fragment comprising LAMP5 formed by digesting pCR2.1 HA-LAMP5 with EcoRI and NotI was cloned at the EcoRI-NotI site of mammalian cell expression vector pCOSII (pCOSII HA-LAMP5). The pCOSII 25 vector is a vector that is able to induce gene expression under the control of human EEF1A1 promoter (NCBI reference sequence: NM 001402) while also incorporating a neomycin resistance gene. The nucleotide sequence from the start codon to the stop codon of pCOSII HA-LAMP5 is illustrated in SEQ ID NO: 7 while the amino acid sequence is illustrated in SEQ ID NO: 8.

2-2. Production of Mouse CD40 Ligand Expression Vector

Mouse CD40 ligand (CD40L, NCBI reference: NM 011616), which is a type II membrane protein, is known to increase antibody production ability by activating B cells by binding with CD40 present on B cells (Enforced and prolonged CD40 ligand expression triggers antibody production in vivo, Eur. J. Immunol. (2001) 31: 3484-92; Synergistic antibody induction by antigen—CD40 ligand fusion protein as improved immunogen, Immunology (2005) 115: 215-22). Therefore, in order to efficiently produce antibody to LAMP5, a cell line produced so as to co-express LAMP5 and CD40L was used as immunogen.

After digesting CD40L gene, which was amplified by PCR using a commercially available mouse spleen cDNA library as template and using a forward primer having an EcoRI site and Kozak sequence (mCD40L-1, SEQ ID NO: 9) and a reverse primer having an NotI site (mCD40L-2, SEQ ID NO: 10), with EcoRI and NotI, the digested product was cloned at the EcoRI-NotI site of mammalian cell expression vector pMCH2i (pMCH2i CD40L). pMCH2i vector is a vector that is able to induce gene expression under the control of mouse CMV promoter (NCBI reference sequence: U68299) and incorporates a hygromycin resistance gene. The nucleotide sequence from the start codon to the stop codon of pMCH2i CD40L is illustrated in SEQ ID NO: 11 while the amino acid sequence is illustrated in SEQ ID NO: 12.

2-3. Production of LAMP5/CD40L-Forced Expression Ba/F3 Cell Line for Immunization pCOSII HA-LAMP5 digested with PvuI was introduced into mouse B cell line Ba/F3 (Riken Bioresource Center) by electroporation. A Ba/F3 cell line was established that constantly expresses LAMP5 having an HA tag added to the N-terminal thereof by screening with Geneticin (LAMP5 Ba/F3). Expression of LAMP5 was confirmed by FACS using anti-HA tag antibody (Sigma-Aldrich Co. LLC., Cat. No. H7411-100UG).

Next, after digesting pMCH2i CD40L with PvuI, a Ba/F3 cell line that co-expresses LAMP5 and CD40L was established by introducing into the LAMP5 Ba/F3 cell line by electroporation followed by screening with hygromycin (LAMP5/CD40L Ba/F3). Expression of CD40L was confirmed by FACS using anti-CD40L antibody (Abcam plc, Cat. No. ab24934). The LAMP5/CD40L Ba/F3 cell line was cultured in RPMI1640 medium comprising 10% FBS (fetal bovine serum), 1 ng/ml of mouse IL-3, penicillin/streptomycin, 500 µg/ml of Geneticin and 1 mg/ml of hygromycin.

2-4. Production of LAMP5-Forced Expression CHO Cell Line for Screening

A CHO cell line expressing LAMP5 having a V5 tag (amino acid sequence: GKPIPNPLLGLDST (SEQ ID NO:83)) added to the N-terminal thereof was established in the manner illustrated below for use in screening for anti-LAMP5 antibody.

First, LAMP5 gene having a V5 tag sequence added to the N-terminal thereof and from which the signal sequence had been removed was cloned in mammalian cell expression vector pMCN2 CD43ss. pMCN2 CD43ss vector is a vector that is able to induce gene expression under the control of mouse CMV promoter and incorporates a neomycin resistance gene. In addition, an altered human CD43 signal sequence (amino acid sequence: MASLLLLLGVLVVSP-DALG (SEQ ID NO:84)) was cloned in the same vector, and a protein encoded by the target gene was produced in the form of a membrane protein or secretory protein by cloning the target gene at an SalI-NotI site. First, LAMP5 gene was amplified by PCR using pCR2.1 LAMP5 as template and using a forward primer having an SalI site and V5 tag sequence (SalI-G-V5-LAMP5-F, SEQ ID NO: 13) and a reverse primer having a NotI site (LAMP5-Not-R). The amplification product obtained by digesting with SalI and NotI was cloned at the SalI-NotI site of pMNC2.1 CD43ss vector (pMCN2 CD43ss V5-LAMP5). The nucleotide sequence from the start codon to the stop codon of pMCN2 CD43ss V5-LAMP5 is illustrated in SEQ ID NO: 14 while the amino acid sequence is illustrated in SEQ ID NO: 15.

Continuing, pMCN2 CD43ss V5-LAMP5 digested with PvuI was introduced into CHO cell line DG44 (Invitrogen Corp.) by electroporation. A CHO cell line constantly expressing LAMP5 having a V5 tag added to the N-terminal thereof was established by screening with Geneticin (LAMP5 CHO). The LAMP5 CHO cell line was cultured in CHO-S-SFM II medium comprising HT supplement, penicillin/streptomycin and 500 µg/ml of Geneticin. Expression of LAMP5 was confirmed by FACS using anti-V5 tag antibody (Invitrogen Corp., Cat. No. R960-25).

2-5. Production of Anti-LAMP5 Monoclonal Antibody

5×10$^6$ LAMP5/CD40L Ba/F3 cells per administration were administered four times (days 0, 14, 22 and 29) into the caudal vein of a Balb/c mouse (female, age 6 weeks, Charles River Laboratories Japan, Inc.). Continuing, the same cells were administered 17 times into the abdominal cavity (days 35, 42, 49, 56, 63, 70, 77, 84, 91, 99, 120, 127, 133, 140, 147, 155 and 176). Finally, hybridomas were produced from immune cells isolated from the spleen excised 3 days after a single administration of the same cells into the caudal vein (day 190). In producing the hybridomas, the spleen cells were first mixed with mouse myeloma cell line P3-X63Ag8U1 (ATCC) at a ratio of about 1.5:1. The cells were fused by gradually adding PEG1500 (Roche Diagnostics K.K.) to this mixture. Next, RPMI1640 medium comprising penicillin/streptomycin was added followed by removing the PEG1500 from the mixture by removing the supernatant by centrifugation. Finally, a suspension obtained by adding HAT medium (RPMI1640 medium comprising 10% FBS, penicillin/streptomycin, 1×HAT Media Supplement (Sigma-Aldrich Co. LLC.) and 0.5×BM-Condimed H1 Hybridoma Cloning Supplement (Roche Diagnostics GmbH) was disseminated into eight 96-well flat bottom plates at 1×10$^5$ P3-X63Ag8U1 cells per well. Screening was carried out after culturing for 7 days in a 5% CO$_2$ incubator at 37° C. Screening was carried out by measuring binding of antibody produced in the culture supernatant to LAMP5 CHO cells and parent CHO cells using a flow cytometer (FACS Calibur, Becton, Dickinson and Company). FITC-labeled anti-mouse IgG antibody (Goat F(ab')2 Fragment Anti-Mouse IgG (H+L)-FITC, Beckman Coulter Inc., Cat. No. IM0819) was used for the secondary antibody. Those wells were selected in which antibody was detected that bound only to LAMP5 CHO cells without binding to parent CHO cells. Monocloning of the hybridomas was carried out from the wells by a limiting dilution technique. As a result, anti-LAMP5 monoclonal antibodies D1, D2, D9 and D10 were established. When the isotypes of these antibodies were measured using Isostrip (Roche Diagnostics GmbH), D1, D2 and D9 were mouse IgG1κ while D9 was mouse IgG2bκ.

Next, the established hybridomas were cultured in HAT medium comprising Ultra Low IgG FBS (Invitrogen Corp.) instead of FBS, and antibodies were purified from the culture supernatant using a HiTrap Protein G HP column (GE Healthcare Bio-Sciences Corp.). The concentration of purified antibody was measured using the DC Protein Assay Kit I (Bio-Rad Laboratories, Inc.).

(Example 3) Determination of Variable Region Gene Sequence of Anti-LAMP5 Monoclonal Antibody Gene sequences were determined for the variable region of the anti-LAMP5 monoclonal antibody produced in Example 2. First, cDNA was synthesized using the Smart Race cDNA Amplification Kit (Clontech Laboratories, Inc.) from total RNA prepared using Trizol from 1×10$^7$ hybridoma cells. The primers used consisted of a primer complementary to the heavy chain constant region of mouse IgG1 (SEQ ID NO: 16), a primer complementary to the heavy chain constant region of mouse IgG2b (SEQ ID NO: 17) or a primer complementary to mouse κ chain constant region (SEQ ID NO: 18). Next, the insertion sequences of each of the amplification products cloned in pCR2.1-TOPO vector were determined using a sequencer. The variable region sequences of each antibody are summarized in the following Tables 3 and 4.

TABLE 3

| Antibody | | SEQ ID NO (base sequence) | SEQ ID NO (amino acid sequence) |
|---|---|---|---|
| D1 | Heavy chain variable region | 19 | 20 |
| | Light chain variable region | 21 | 22 |
| D2 | Heavy chain variable region | 23 | 24 |
| | Light chain variable region | 25 | 26 |
| D9 | Heavy chain variable region | 27 | 28 |
| | Light chain variable region | 29 | 30 |
| D10 | Heavy chain variable region | 31 | 32 |
| | Light chain variable region | 33 | 34 |

TABLE 4

| Antibody | | | SEQ ID NO (amino acid sequence) |
|---|---|---|---|
| D1 | Heavy chain | CDR1 | 35 |
| | | CDR2 | 36 |
| | | CDR3 | 37 |
| | Light chain | CDR1 | 38 |
| | | CDR2 | 39 |
| | | CDR3 | 40 |
| D2 | Heavy chain | CDR1 | 41 |
| | | CDR2 | 42 |
| | | CDR3 | 43 |
| | Light chain | CDR1 | 44 |
| | | CDR2 | 45 |
| | | CDR3 | 46 |
| D9 | Heavy chain | CDR1 | 47 |
| | | CDR2 | 48 |
| | | CDR3 | 49 |
| | Light chain | CDR1 | 50 |
| | | CDR2 | 51 |
| | | CDR3 | 52 |
| D10 | Heavy chain | CDR1 | 53 |
| | | CDR2 | 54 |
| | | CDR3 | 55 |
| | Light chain | CDR1 | 56 |
| | | CDR2 | 57 |
| | | CDR3 | 58 |

(Example 4) Binding Analysis of Anti-LAMP5 Monoclonal Antibody to Mouse LAMP5

4-1. Production of Mouse LAMP5-Forced Expression CHO Cell Line

In order to examine cross-reactivity of the produced anti-LAMP5 monoclonal antibody to mouse LAMP5 (mLAMP5), an mLAMP5 expression vector having a V5 tag on the N-terminal thereof was produced in the same manner as LAMP5. First, using a commercially available mouse brain cDNA library as template, mLAMP5 gene was amplified by PCR using a forward primer (mLAMP5-F, SEQ ID NO: 59) and a reverse primer (mLAMP5-R, SEQ ID NO: 60) followed by cloning in pCR2.1-TOPO vector (pCR2.1 mLAMP5). Next, using pCR2.1 mLAMP5 as template, mLAMP5 gene was amplified by PCR using a forward primer having an SalI site and V5 tag sequence (SalI-G-V5-mLAMP5-F, SEQ ID NO: 61) and a reverse primer having a NotI site (mLAMP5-NotI-R, SEQ ID NO: 62). The amplification product digested with SalI and NotI was cloned at the SalI-NotI site of pMCN2 CD43ss vector (pMCN2 CD43ss V5-mLAMP5). The nucleotide sequence from the start codon to the stop codon of pMCN2 CD43ss V5-mLAMP5 is illustrated in SEQ ID NO: 63 while the amino acid sequence is illustrated in SEQ ID NO: 64.

Continuing, pMCN2 CD43ss V5-mLAMP5 digested with PvuI was introduced into CHO cell line DC44 by electroporation. A CHO cell line constantly expressing mLAMP5 having a V5 tag added to the N-terminal thereof was established by screening with Geneticin (mLAMP5 CHO). Expression of mLAMP5 was confirmed by FACS using anti-V5 tag antibody. The mLAMP5 CHO cell line was cultured in CHO-S-SFM II medium comprising HT supplement, penicillin/streptomycin and 500 μg/ml of Geneticin.

4-2. Binding Analysis of Anti-LAMP5 Monoclonal Antibody to Mouse LAMP5

Binding of the anti-LAMP5 monoclonal antibody produced in Example 2 to LAMP5 and mLAMP5 was evaluated by FACS. First, LAMP5 CHO (Example 2) or mLAMP5 CHO was suspended in FACS/PBS (PBS(−) comprising 0.2% bovine serum albumin (BSA) and 0.1% sodium azide) followed by disseminating into the wells of a 96-well round bottom plate at $5 \times 10^4$ cells per well. After adding anti-LAMP5 monoclonal antibody to each well to a final concentration of 10, 2, 0.4, 0.08 or 0.016 μg/ml, the mixture was allowed to react for 1 hour on ice. After reacting, the cell suspensions were washed with FACS/PBS and allowed to react for 1 hour with FITC-labeled anti-mouse IgG antibody on ice. After reacting, the cells were washed with FACS/PBS and then suspended in FACS/PBS comprising 10 μg/ml of propidium iodide (Sigma-Aldrich Co. LLC.). The staining intensity of the cells was measured with a flow cytometer. Only viable cells not stained with propidium iodide were used in data analysis. As a result, clones D1, D2, D9 and D10 all bound concentration-dependently to LAMP5 (FIG. 2A). Clones D1, D2 and D10 in particular bound strongly in comparison with clone D9 (FIG. 2A). On the other hand, although clone D2 bound strongly to mLAMP5, clones D1 and D9 did not bind thereto (FIG. 2B). Clone D10 only bound weakly to mLAMP5 (FIG. 2B). On the basis of the above, each of the four clones produced exhibited different antigen binding properties.

Figure 3A:
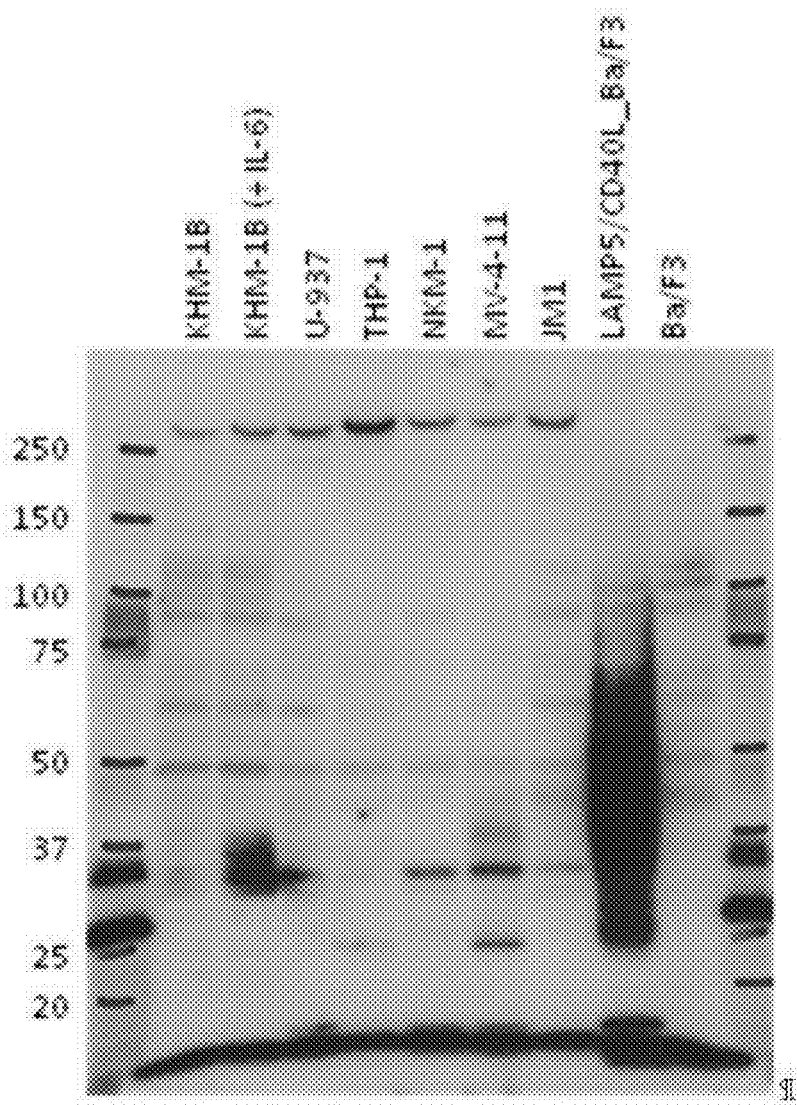
FIG. 3A is a photograph illustrating the results of detecting expression of LAMP5 in cancer cell lines by Western blot analysis using anti-LAMP5 monoclonal antibody.

(Example 5) Expression Analysis of LAMP5 in Cancer Cell Lines 5-1. Expression Analysis of LAMP5 by Western Blotting Expression of LAMP5 in cancer cell lines was evaluated by Western blotting using commercially available anti-LAMP5 monoclonal antibody. The specimens used consisted of multiple myeloma cell line KHM-1B (JCRB Cell Bank), histiocytic lymphoma cell line U-937 (JCRB Cell Bank), acute monocytic leukemia cell line THP-1 (JCRB Cell Bank), acute myeloid leukemia cell line NKM-1 (JCRB Cell Bank), biphenotypic B-myelocytic leukemia cell line MV-4-11 (ATCC), B cell lymphoma cell line JM1 (ATCC), LAMP5/CD40L Ba/F3 (Example 2) and Ba/F3 (Riken Bioresource Center). Furthermore, since interleukin 6 (IL-6) is known to be involved in the pathology of multiple myeloma, expression of LAMP5 was also evaluated in KHM-1B cells cultured in the presence of 10 ng/ml of IL-6 (Peprotech, Inc., Cat. No. 200-06). First, after washing $1 \times 10^7$ cells of each cell line with PBS, the cells were lysed using 1 mL of lysis buffer (50 mM Tris-HCl (pH 7.4), 150 mM NaCl, 1 mM EDTA, 1% Triton X-100 and Protease Inhibitor Cocktail (Sigma-Aldrich Co. LLC.) to obtain a whole cell lysate. After mixing with an equal volume of 2× Sample Buffer (Sigma-Aldrich Co. LLC.), the lysate was subjected to heat treatment followed by subjecting to SDS-PAGE electrophoresis in 30 μL aliquots. After phoresis, the transferred PVDF membrane (Immobilon-P, Millipore Corporation) was allowed to react for 1 hour at room temperature with 8 μg/mL of anti-LAMP5 polyclonal antibody (Anti-C20orf103 (266-280), Antibody Produced in Rabbit (Sigma-Aldrich Co. LLC.), Cat. No. SAB1101729). HRP-labeled anti-rabbit IgG antibody (GE Healthcare Bio-Sciences Corp., Cat. No. NA934-1ML) was used for the secondary antibody. Finally, fluorescence obtained using ECL Western Blotting Detection Reagents (GE Healthcare Bio-Sciences Corp.) was detected by exposing to X-ray film or using an image analyzer (LAS 4000mini, GE Healthcare Bio-Sciences Corp.). As a result, in contrast to an intense band having been detected with LAMP5/CD40L Ba/F3, hardly any band was detected with the parent strain in the form of Ba/F3, thereby confirming that the antibody used specifically detects LAMP5 (FIG. 3A). Moreover, bands were also observed with KHM-1B, U-937, NKM-1, MV-4-11 and JM1 (FIG. 3A).

Figure 3B:
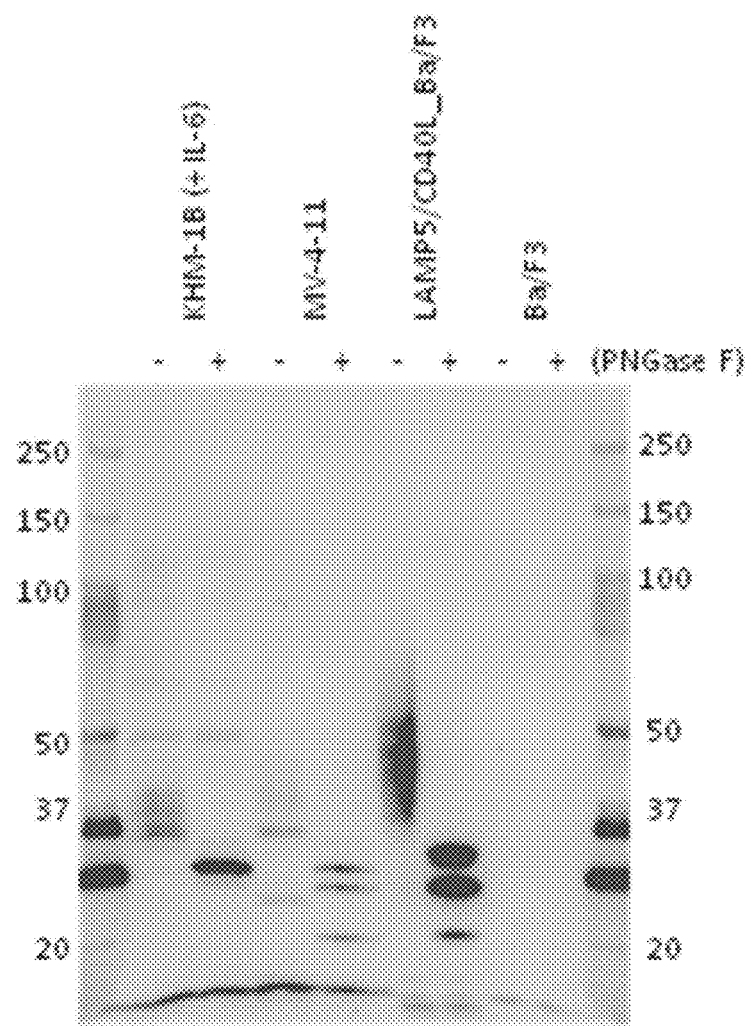
FIG. 3B is a photograph illustrating the results of detecting expression of LAMP5 in deglycosylated cancer cell lines by Western blot analysis using anti-LAMP5 monoclonal antibody.

Since LAMP5 is known to undergo sugar chain modification, whole cell lysates of KHM-1B (cultured in the presence of IL-6), MV-4-11, LAMP5/CD40L Ba/F3 and Ba/F3 subjected to deglycosylation treatment using PNGase F (New England Biolabs Inc.) were subjected to Western blotting. As a result, a band was observed in the vicinity of 31 kDa, which is the molecular weight predicted from the amino acid sequence following deglycosylation treatment (FIG. 3B). Two additional low molecular weight bands were also observed with MV-4-11 and LAMP5/CD40L Ba/F3 (FIG. 3B). On the basis of the above, LAMP5 protein was shown to be expressed in KHM-1B and MV-4-11, and the expressed amount thereof was shown to be increased by IL-6.

5-2. Expression Analysis by FACS

Figure 4A:
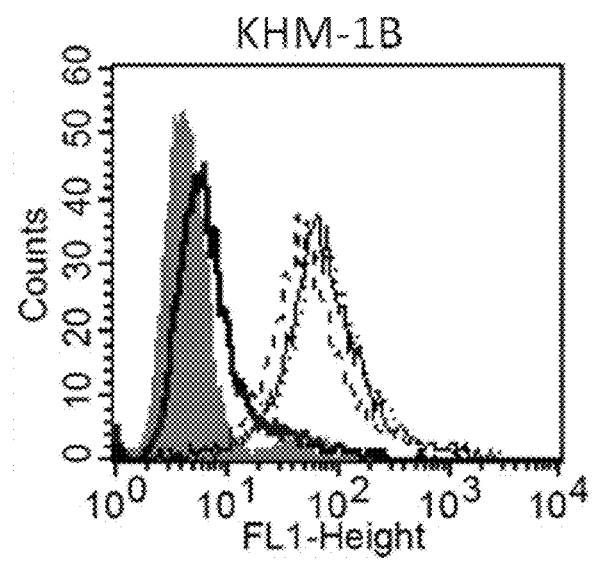
FIG. 4A is a graph illustrating the results of FACS for evaluating binding of anti-LAMP5 monoclonal antibodies D1 (solid line), D2 (broken line), D9 (thick line) and D10 (dotted line) to KHM-1B cells.
Figure 4B:
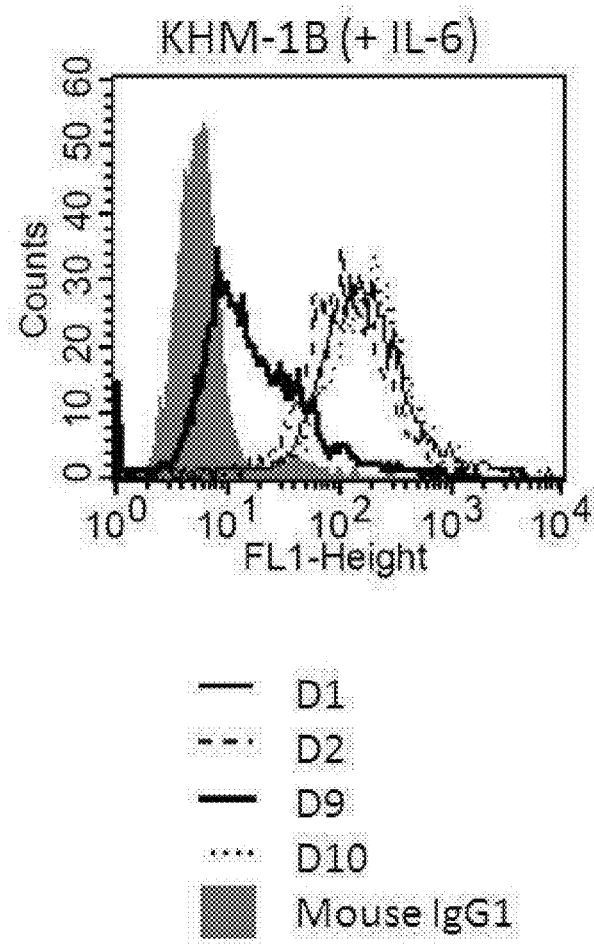
FIG. 4B is a graph illustrating the results of FACS for evaluating binding of anti-LAMP5 monoclonal antibodies D1 (solid line), D2 (broken line), D9 (thick line) and D10 (dotted line) to IL-6-stimulated KHM-1B cells (B).

Next, LAMP5 expression was measured by FACS in KHM-1B cells (with or without IL-6 stimulation). FACS was carried out in the same manner as Example 4 using anti-LAMP5 monoclonal antibodies D1, D2, D9 and D10 and a negative reference in the form of IgG1κ (Pharmingen Inc., Cat. No. 553447) at concentrations of 10 μg/mL. As a result, LAMP5 was detected on the cell membrane of KHM-1B cells, and the expressed amount thereof was confirmed to be increased by IL-6 stimulation (FIG. 4).

(Example 6) Study of ADCC Activity and Cell Growth Inhibitory Activity of Anti-LAMP5 Monoclonal Antibody 6-1. Study of ADCC Activity of Anti-LAMP5 Monoclonal Antibody Antibody-dependent cell-mediated cytotoxicity (ADCC) activity was measured for the anti-LAMP5 monoclonal antibody produced in Example 2. After culturing KHN-1B cells (with or without IL-6 stimulation) for 1.5 hours in the presence of Calcein-AM (Wako Pure Chemical Industries, Ltd., Cat. No. 349-07201) and washing with RPMI1640 medium comprising 10% FBS and penicillin/streptomycin (to simply be referred as the medium), the cells were suspended at a concentration of $2 \times 10^5$ cells/mL using the medium. 50 μL aliquots of the cell suspension were added to each well of a 96-well round bottom plate. Next, anti-LAMP5 monoclonal antibodies D1, D2, D9 and D10 along with mouse IgG1κ used as a negative reference were added at 50 μL/well after diluting with the medium. The final antibody concentration was adjusted to 1 μg/mL. After allowing to stand undisturbed for 15 minutes on ice, effector cells adjusted to a concentration of 5×10⁵ cells/mL with the medium were added at 100 μL/well. Cells constantly expressing in NK-92 cells (ATCC) a chimeric protein obtained by fusing the extracellular region of mouse Fcγ receptor III (NCBI reference sequence: NM 010188) and the transmembrane region and intracellular region of human Fcε receptor I-gamma (NCBI reference sequence: NM 004106) (WO 2008/093688) were used as effector cells. After culturing the plate for 3 hours in a 5% $CO_2$ incubator at 37° C., the fluorescence intensity of culture supernatant recovered at 100 μL per cell was measured using a microplate reader (ARVO SX 1420 Multilabel Counter, PerkinElmer Inc.). The specific calcein release rate (%) was determined by substituting the measured values into the equation illustrated below.

Specific calcein release rate(%)=(A−C)×100/(B−C)

Here, A represents the measured value of each well, B represents the average measured value of those wells in which the cells were lysed with 1% Nonidet P-40, and C represents the average measured value of those wells in which only target cells were added. The experiment was conducted in triplicate followed by calculation of the mean and standard deviation of the specific calcein release rate.

As a result, high specific calcein release rates were observed in the culture supernatants in which clones D1, D2 and D10 reacted in comparison with mouse IgG1κ, and ADCC against KHM-1B cells was shown to be induced by clones D1, D2 and D10 (FIG. 5). In addition, ADCC activity was observed regardless of IL-6 stimulation of the KHM-1B cells (FIG. 5).

6-2. Study of Cell Growth Inhibitory Activity of Anti-LAMP5 Monoclonal Antibody

Figure 6:
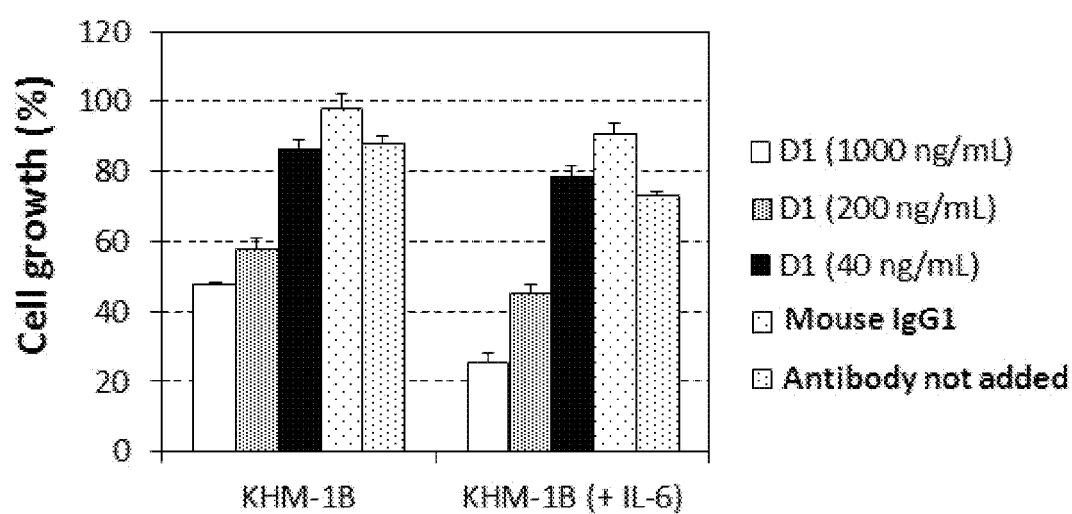
FIG. 6 is a graph illustrating cell growth inhibitory activity of anti-LAMP5 monoclonal antibody D1 against KHM-1B cells (with or without IL-6 stimulation) in the presence of toxin-linked secondary antibody.

Cell growth inhibitory activity of anti-LAMP5 monoclonal antibody D1 was measured in the presence of toxin-bound secondary antibody. Saporin-labeled anti-mouse IgG antibody (Mab-Zap, Advanced Targeting Systems, Inc.) was used for the toxin-labeled secondary antibody. KHM-1B cells (with or without IL-6 stimulation) were disseminated in a 96-well flat bottom plate at 4×10⁴ cells/well followed by the addition of D1 antibody (1000 ng/mL, 200 ng/mL or 40 ng/mL) or mouse IgG1κ (5000 ng/mL). Mab-Zap was added at a concentration of 2500 ng/mL. After culturing the plate for 3 days, cell growth in each well was measured using WST-8 (Cell Count Reagent SF, Nacalai Tesque, Inc.). The experiment was conducted in triplicate and the mean and standard deviation were calculated based on a value of 0% for those wells in which only medium was added and a value of 100% for those wells in which only cells were added. RPMI1640 medium comprising 10% FBS and penicillin/streptomycin was used for the medium, and in the experiment in which the cells were stimulated by IL-6, IL-6 was added at 10 ng/mL. As a result, D1 antibody inhibited cell growth concentration-dependently in the presence of toxin-labeled secondary antibody (FIG. 6). Thus, anti-LAMP5 antibody was shown to have the potential to inhibit the growth of cancer cells by binding a toxin directly thereto.

INDUSTRIAL APPLICABILITY

The monoclonal antibody of the present invention is able to demonstrate cytotoxic activity and internalization activity by binding to LAMP5 expressed on the cell surface. According to the present invention, the present invention can be used in the field of health care in particular since it enables the development of novel anticancer drugs and novel treatment methods for multiple myeloma and other forms of cancer. In addition, the monoclonal antibody of the present invention can also be used as a reagent for detecting, purifying or regulating the function of LAMP5.

SEQUENCE LISTING FREE TEXT

SEQ ID NO: 1: LAMP5-F
SEQ ID NO: 2: LAMP5-R
SEQ ID NO: 3: Eco-Kozak-LAMP5-F
SEQ ID NO: 4: HAtag-LAMP5-R
SEQ ID NO: 5: HAtag-LAMP5-F
SEQ ID NO: 6: LAMP5-Not-R
SEQ ID NO: 7: pCOSII_HA-LAMP5
SEQ ID NO: 8: pCOSII_HA-LAMP5
SEQ ID NO: 9: mCD40L-1
SEQ ID NO: 10: mCD40L-2
SEQ ID NO: 13: SalI-G-V5-LAMP5-F
SEQ ID NO: 14: pMCN2_CD43ss_V5-LAMP5
SEQ ID NO: 15: pMCN2_CD43ss_V5-LAMP5
SEQ ID NO: 16: mIgG_CH primer
SEQ ID NO: 17: mIgG2b_CH primer
SEQ ID NO: 18: Mk_CL primer
SEQ ID NO: 59: mLAMP5-F
SEQ ID NO: 60: mLAMP5-R
SEQ ID NO: 61: SalI-G-V5-mLAMP5-F
SEQ ID NO: 62: mLAMP5-NotI-R
SEQ ID NO: 63: pMCN2_CD43ss_V5-mLAMP5
SEQ ID NO: 64: pMCN2_CD43ss_V5-mLAMP5
SEQ ID NO: 68: Human IgG1 (AAC82527.1) to which an alanine is added N-terminally
SEQ ID NO: 69: Human IgG2 (AAB59393.1) to which an alanine is added N-terminally
SEQ ID NO: 71: Human IgG4 (AAB59394.1) to which an alanine is added N-terminally
SEQ ID NO: 74: Linker
SEQ ID NO: 75: Linker
SEQ ID NO: 76: Linker
SEQ ID NO: 77: Linker
SEQ ID NO: 78: Linker
SEQ ID NO: 79: Linker
SEQ ID NO: 80: Linker
SEQ ID NO: 81: Linker

The invention claimed is:

1. A monoclonal antibody according to any of the following (1) to (9):
   (1) an antibody comprising a heavy chain variable region comprising the CDR1 defined by SEQ ID NO: 35, the CDR2 defined by SEQ ID NO: 36 and the CDR3 defined by SEQ ID NO: 37, and a light chain variable region comprising the CDR1 defined by SEQ ID NO: 38, the CDR2 defined by SEQ ID NO: 39 and the CDR3 defined by SEQ ID NO: 40;
   (2) an antibody comprising a heavy chain variable region comprising the CDR1 defined by SEQ ID NO: 41, the CDR2 defined by SEQ ID NO: 42 and the CDR3 defined by SEQ ID NO: 43, and a light chain variable region comprising the CDR1 defined by SEQ ID NO: 44, the CDR2 defined by SEQ ID NO: 45 and the CDR3 defined by SEQ ID NO: 46;
   (3) an antibody comprising a heavy chain variable region comprising the CDR1 defined by SEQ ID NO: 47, the CDR2 defined by SEQ ID NO: 48 and the CDR3 defined by SEQ ID NO: 49, and a light chain variable region comprising the CDR1 defined by SEQ ID NO: 50, the CDR2 defined by SEQ ID NO: 51 and the CDR3 defined by SEQ ID NO: 52;
   (4) an antibody comprising a heavy chain variable region comprising the CDR1 defined by SEQ ID NO: 53, the CDR2 defined by SEQ ID NO: 54 and the CDR3 defined by SEQ ID NO: 55, and a light chain variable region comprising the CDR1 defined by SEQ ID NO: 56, the CDR2 defined by SEQ ID NO: 57 and the CDR3 defined by SEQ ID NO: 58;
   (5) the monoclonal antibody according to any of (1) to (4), comprising a heavy chain comprising a heavy chain constant region of human IgG and/or a light chain comprising a light chain constant region of human antibody;
   (6) the monoclonal antibody according to (5), wherein the heavy chain comprising a heavy chain constant region of human IgG is a heavy chain comprising the heavy chain constant region defined by SEQ ID NO: 68;
   (7) the monoclonal antibody according to (5) or (6), wherein the light chain comprising a light chain constant region of human antibody is a light chain comprising the light chain constant region defined by SEQ ID NO: 73;
   (8) a monoclonal antibody in which one amino acid is substituted, deleted, added or inserted in the antibody according to any of (1) to (7) and which has binding activity equivalent to that of the monoclonal antibody according to any of (1) to (7) with respect to an epitope present at position 39 to position 289 of the polypeptide defined in SEQ ID NO: 8 expressed on a cell surface; or
   (9) the monoclonal antibody according to (5) or (7), wherein the heavy chain comprising a heavy chain constant region of human IgG is a heavy chain that comprises one substitution of an amino acid selected from the group of amino acids at position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440, as defined by the EU numbering system, in the heavy chain constant region of SEQ ID NO: 68.

2. A pharmaceutical composition comprising:
the monoclonal antibody according to claim 1 as an active ingredient thereof;
a pharmacologically acceptable carrier or additive; and
IL-6 or a salt thereof.

3. An anticancer drug comprising:
the monoclonal antibody according to claim 1 as an active ingredient thereof;
a pharmacologically acceptable carrier or additive; and
IL-6 or a salt thereof, that allows for treating cancer.

4. A pharmaceutical composition comprising the monoclonal antibody according to claim 1 and IL-6 or a salt thereof as an active ingredient.

5. An anticancer drug comprising the monoclonal antibody according to claim 1 and IL-6 or a salt thereof as an active ingredient, that allows for treating cancer.

6. A monoclonal antibody, which binds to an epitope present from position 30 to position 235 of a polypeptide defined in SEQ ID NO: 65 expressed on a cell surface, wherein the monoclonal antibody has internalization activity, and is produced according to a method comprising recovering the monoclonal antibody from a culture fluid of a host cell comprising a vector selected from the group consisting of the following (A) to (D):

(A) the vector according to (1) below and the vector according to (4) below;
(B) the vector according to (2) below and the vector according to (5) below;
(C) the vector according to (3) below and the vector according to (5) below; and
(D) the vector according to any of (6) to (8) below:
(1) a vector comprising a polynucleotide encoding a heavy chain variable region selected from a group consisting of the following (a) to (d):
(a) a heavy chain variable region comprising the CDR1 defined by SEQ ID NO: 35, the CDR2 defined by SEQ ID NO: 36 and the CDR3 defined by SEQ ID NO: 37;
(b) a heavy chain variable region comprising the CDR1 defined by SEQ ID NO: 41, the CDR2 defined by SEQ ID NO: 42 and the CDR3 defined by SEQ ID NO: 43;
(c) a heavy chain variable region comprising the CDR1 defined by SEQ ID NO: 47, the CDR2 defined by SEQ ID NO: 48 and the CDR3 defined by SEQ ID NO: 49; or,
(d) a heavy chain variable region comprising the CDR1 defined by SEQ ID NO: 53, the CDR2 defined by SEQ ID NO: 54 and the CDR3 defined by SEQ ID NO: 55;
(2) a vector comprising a polynucleotide encoding the heavy chain variable region according to any of (a) to (d) of (1) above and the heavy chain constant region of SEQ ID NO: 68;
(3) a vector comprising a variant nucleotide encoding one substitution of an amino acid selected from the group of amino acids at position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440, as defined by the EU numbering system, in a polynucleotide encoding the heavy chain variable region according to any of (a) to (d) of (1) above and the heavy chain constant region of SEQ ID NO: 68;
(4) a vector comprising a polynucleotide encoding a light chain variable region selected from a group consisting of the following (e) to (h):
(e) a light chain variable region comprising the CDR1 defined by SEQ ID NO: 38, the CDR2 defined by SEQ ID NO: 39 and the CDR3 defined by SEQ ID NO: 40;
(f) a light chain variable region comprising the CDR1 defined by SEQ ID NO: 44, the CDR2 defined by SEQ ID NO: 45 and the CDR3 defined by SEQ ID NO: 46;
(g) a light chain variable region comprising the CDR1 defined by SEQ ID NO: 50, the CDR2 defined by SEQ ID NO: 51 and the CDR3 defined by SEQ ID NO: 52; or,
(h) a light chain variable region comprising the CDR1 defined by SEQ ID NO: 56, the CDR2 defined by SEQ ID NO: 57 and the CDR3 defined by SEQ ID NO: 58;
(5) a vector comprising a polynucleotide encoding the light chain variable region according to any of (e) to (h) of (4) above and the light chain constant region of SEQ ID NO: 73;
(6) a vector comprising a polynucleotide encoding the heavy chain variable region and light chain variable region selected from a group consisting of the following (i) to (l):
(i) a heavy chain variable region comprising the CDR1 defined by SEQ ID NO: 35, the CDR2 defined by SEQ ID NO: 36 and the CDR3 defined by SEQ ID NO: 37, and a light chain variable region comprising the CDR1 defined by SEQ ID NO: 38, the CDR2 defined by SEQ ID NO: 39 and the CDR3 defined by SEQ ID NO: 40;
(j) a heavy chain variable region comprising the CDR1 defined by SEQ ID NO: 41, the CDR2 defined by SEQ ID NO: 42 and the CDR3 defined by SEQ ID NO: 43, and a light chain variable region comprising the CDR1 defined by SEQ ID NO: 44, the CDR2 defined by SEQ ID NO: 45 and the CDR3 defined by SEQ ID NO: 46;
(k) a heavy chain variable region comprising the CDR1 defined by SEQ ID NO: 47, the CDR2 defined by SEQ ID NO: 48 and the CDR3 defined by SEQ ID NO: 49, and a light chain variable region comprising the CDR1 defined by SEQ ID NO: 50, the CDR2 defined by SEQ ID NO: 51 and the CDR3 defined by SEQ ID NO: 52; or, (l) a heavy chain variable region comprising the CDR1 defined by SEQ ID NO: 53, the CDR2 defined by SEQ ID NO: 54 and the CDR3 defined by SEQ ID NO: 55, and a light chain variable region comprising the CDR1 defined by SEQ ID NO: 56, the CDR2 defined by SEQ ID NO: 57 and the CDR3 defined by SEQ ID NO: 58;

(7) a vector comprising a polynucleotide encoding the heavy chain variable region and light chain variable region according to any of (i) to (1) of (6) above, and a polynucleotide encoding the light chain constant region of SEQ ID NO: 73, and/or a polynucleotide encoding the heavy chain constant region of SEQ ID NO: 68; or, (8) a vector comprising a variant nucleotide encoding one substitution of an amino acid selected from the group of amino acids at position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440, as defined by the EU numbering system, in a polynucleotide encoding the heavy chain variable region and light chain variable region according to any of (i) to (1) of (6) above, and a polynucleotide encoding the light chain constant region of SEQ ID NO: 73, and/or a polynucleotide encoding the heavy chain constant region of SEQ ID NO: 68.

7. A pharmaceutical composition comprising:
the monoclonal antibody according to claim 6 as an active ingredient thereof;
a pharmacologically acceptable carrier or additive; and
IL-6 or a salt thereof.

8. An anticancer drug comprising:
the monoclonal antibody according to claim 6 as an active ingredient thereof;
a pharmacologically acceptable carrier or additive; and
IL-6 or a salt thereof, that allows for treating cancer.

9. A pharmaceutical composition comprising the monoclonal antibody according to claim 6 and IL-6 or a salt thereof as an active ingredient.

10. An anticancer drug comprising the monoclonal antibody according to claim 6 and IL-6 or a salt thereof as an active ingredient, that allows for treating cancer.

* * * * *

SEQUENCE LISTING

<160> NUMBER OF SEQ ID NOS: 84

<210> SEQ ID NO 1
<211> LENGTH: 22
<212> TYPE: DNA
<213> ORGANISM: Artificial Sequence

```
<220> FEATURE:
<223> OTHER INFORMATION: LAMP5-F

<400> SEQUENCE: 1
atggatctcc aaggaagagg gg                                              22

<210> SEQ ID NO 2
<211> LENGTH: 23
<212> TYPE: DNA
<213> ORGANISM: Artificial Sequence
<220> FEATURE:
<223> OTHER INFORMATION: LAMP5-R

<400> SEQUENCE: 2
ctagcccatg tgcttatact ggg                                             23

<210> SEQ ID NO 3
<211> LENGTH: 31
<212> TYPE: DNA
<213> ORGANISM: Artificial Sequence
<220> FEATURE:
<223> OTHER INFORMATION: Eco-Kozak-LAMP5-F

<400> SEQUENCE: 3
gaattcacca tggatctcca aggaagaggg g                                    31

<210> SEQ ID NO 4
<211> LENGTH: 56
<212> TYPE: DNA
<213> ORGANISM: Artificial Sequence
<220> FEATURE:
<223> OTHER INFORMATION: HAtag-LAMP5-R

<400> SEQUENCE: 4
gttcagcgta atctggaaca tcgtatgggt atgccatgat ttgagccatt gtatgg         56

<210> SEQ ID NO 5
<211> LENGTH: 54
<212> TYPE: DNA
<213> ORGANISM: Artificial Sequence
<220> FEATURE:
<223> OTHER INFORMATION: HAtag-LAMP5-F

<400> SEQUENCE: 5
ggcataccca tacgatgttc cagattacgc tgaacaagaa gtggaaaatc tctc           54

<210> SEQ ID NO 6
<211> LENGTH: 30
<212> TYPE: DNA
<213> ORGANISM: Artificial Sequence
<220> FEATURE:
<223> OTHER INFORMATION: LAMP5-Not-R

<400> SEQUENCE: 6
gcggccgcct agcccatgtg cttatactgg                                      30

<210> SEQ ID NO 7
<211> LENGTH: 870
<212> TYPE: DNA
<213> ORGANISM: Artificial Sequence
<220> FEATURE:
<223> OTHER INFORMATION: pCOSII_HA-LAMP5

<400> SEQUENCE: 7
atggatctcc aaggaagagg ggtccccagc atcgacagac ttcgagttct cctgatgttg     60
```

-continued

```
ttccatacaa tggctcaaat catggcatac ccatacgatg ttccagatta cgctgaacaa    120
gaagtggaaa atctctcagg cctttccact aaccctgaaa aagatatatt tgtggtgcgg    180
gaaaatggga cgacgtgtct catggcagag tttgcagcca aatttattgt accttatgat    240
gtgtgggcca gcaactacgt agatctgatc acagaacagg ccgatatcgc attgacccgg    300
ggagctgagg tgaagggccg ctgtggccac agccagtcgg agctgcaagt gttctgggtg    360
gatcgcgcat atgcactcaa aatgctcttt gtaaaggaaa gccacaacat gtccaaggga    420
cctgaggcga cttggaggct gagcaaagtg cagtttgtct acgactcctc ggagaaaacc    480
cacttcaaag acgcagtcag tgctgggaag cacacagcca actcgcacca cctctctgcc    540
ttggtcaccc ccgctgggaa gtcctatgag tgtcaagctc aacaaaccat ttcactggcc    600
tctagtgatc cgcagaagac ggtcaccatg atcctgtctg cggtccacat ccaaccttt    660
gacattatct cagattttgt cttcagtgaa gagcataaat gcccagtgga tgagcgggag    720
caactggaag aaaccttgcc cctgattttg gggctcatct tgggcctcgt catcatggta    780
acactcgcga tttaccacgt ccaccacaaa atgactgcca accaggtgca gatccctcgg    840
gacagatccc agtataagca catgggctag                                     870
```

<210> SEQ ID NO 8
<211> LENGTH: 289
<212> TYPE: PRT
<213> ORGANISM: Artificial Sequence
<220> FEATURE:
<223> OTHER INFORMATION: pCOSII_HA-LAMP5

<400> SEQUENCE: 8

```
Met Asp Leu Gln Gly Arg Gly Val Pro Ser Ile Asp Arg Leu Arg Val
1               5                   10                  15

Leu Leu Met Leu Phe His Thr Met Ala Gln Ile Met Ala Tyr Pro Tyr
                20                  25                  30

Asp Val Pro Asp Tyr Ala Glu Gln Glu Val Glu Asn Leu Ser Gly Leu
            35                  40                  45

Ser Thr Asn Pro Glu Lys Asp Ile Phe Val Val Arg Glu Asn Gly Thr
        50                  55                  60

Thr Cys Leu Met Ala Glu Phe Ala Ala Lys Phe Ile Val Pro Tyr Asp
65                  70                  75                  80

Val Trp Ala Ser Asn Tyr Val Asp Leu Ile Thr Glu Gln Ala Asp Ile
                85                  90                  95

Ala Leu Thr Arg Gly Ala Glu Val Lys Gly Arg Cys Gly His Ser Gln
            100                 105                 110

Ser Glu Leu Gln Val Phe Trp Val Asp Arg Ala Tyr Ala Leu Lys Met
        115                 120                 125

Leu Phe Val Lys Glu Ser His Asn Met Ser Lys Gly Pro Glu Ala Thr
    130                 135                 140

Trp Arg Leu Ser Lys Val Gln Phe Val Tyr Asp Ser Ser Glu Lys Thr
145                 150                 155                 160

His Phe Lys Asp Ala Val Ser Ala Gly Lys His Thr Ala Asn Ser His
                165                 170                 175

His Leu Ser Ala Leu Val Thr Pro Ala Gly Lys Ser Tyr Glu Cys Gln
            180                 185                 190

Ala Gln Gln Thr Ile Ser Leu Ala Ser Ser Asp Pro Gln Lys Thr Val
        195                 200                 205

Thr Met Ile Leu Ser Ala Val His Ile Gln Pro Phe Asp Ile Ile Ser
    210                 215                 220
```

-continued

```
Asp Phe Val Phe Ser Glu Glu His Lys Cys Pro Val Asp Glu Arg Glu
225                 230                 235                 240

Gln Leu Glu Glu Thr Leu Pro Leu Ile Leu Gly Leu Ile Leu Gly Leu
            245                 250                 255

Val Ile Met Val Thr Leu Ala Ile Tyr His Val His Lys Met Thr
        260                 265                 270

Ala Asn Gln Val Gln Ile Pro Arg Asp Arg Ser Gln Tyr Lys His Met
        275                 280                 285

Gly

<210> SEQ ID NO 9
<211> LENGTH: 40
<212> TYPE: DNA
<213> ORGANISM: Artificial Sequence
<220> FEATURE:
<223> OTHER INFORMATION: mCD40L-1

<400> SEQUENCE: 9
taagaattcc accatgatag aaacatacag ccaaccttcc                              40

<210> SEQ ID NO 10
<211> LENGTH: 32
<212> TYPE: DNA
<213> ORGANISM: Artificial
<220> FEATURE:
<223> OTHER INFORMATION: mCD40L-2

<400> SEQUENCE: 10
ttagcggccg ctcagagttt gagtaagcca aa                                      32

<210> SEQ ID NO 11
<211> LENGTH: 783
<212> TYPE: DNA
<213> ORGANISM: Mus musculus

<400> SEQUENCE: 11
atgatagaaa catacagcca accttccccc agatccgtgg caactggact tccagcgagc         60
atgaagattt tatgtatttt acttactgtt ttccttatca cccaaatgat tggatctgtg        120 cttttttgctg tgtatcttca tagaagattg ataaggtcg aagaggaagt aaaccttcat        180
gaagattttg tattcataaa aaagctaaag agatgcaaca aaggagaagg atctttatcc        240
ttgctgaact gtgaggagat gagaaggcaa tttgaagacc ttgtcaagga tataacgtta        300
aacaaagaag agaaaaaaga aaacagcttt gaaatgcaaa gaggtgatga ggatcctcaa        360
attgcagcac acgttgtaag cgaagccaac agtaatgcag catccgttct acagtgggcc        420
aagaaaggat attataccat gaaaagcaac ttggtaatgc ttgaaaatgg gaaacagctg        480
acggttaaaa gagaaggact ctattatgtc tacactcaag tcaccttctg ctctaatcgg        540
gagccttcga gtcaacgccc attcatcgtc ggcctctggc tgaagcccag cagtggatct        600
gagagaatct tactcaaggc ggcaaatacc cacagttcct cccagctttg cgagcagcag        660
tctgttcact gggcggagt gtttgaatta caagctggtg cttctgtgtt tgtcaacgtg         720
actgaagcaa gccaagtgat ccacagagtt ggcttctcat cttttggctt actcaaactc        780
tga                                                                     783

<210> SEQ ID NO 12
<211> LENGTH: 260
<212> TYPE: PRT
```

<213> ORGANISM: Mus musculus

<400> SEQUENCE: 12

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 13
<211> LENGTH: 78
<212> TYPE: DNA
<213> ORGANISM: Artificial Sequence
<220> FEATURE:
<223> OTHER INFORMATION: SalI-G-V5-LAMP5-F

<400> SEQUENCE: 13
taagtcgacg gtggtaagcc tatccctaac cctctcctcg gtctcgattc tacggaacaa      60
gaagtggaaa atctctca                                                   78

<210> SEQ ID NO 14
<211> LENGTH: 864
<212> TYPE: DNA
<213> ORGANISM: Artificial Sequence
<220> FEATURE:
<223> OTHER INFORMATION: pMCN2_CD43ss_V5-LAMP5

<400> SEQUENCE: 14

```
atggctagcc ttctccttct ccttggggtg ctggtggtaa gcccagacgc tctgggggtc      60
gacggtggta agcctatccc taaccctctc ctcggtctcg attctacgga acaagaagtg     120
gaaaatctct caggcctttc cactaaccct gaaaaagata tatttgtggt gcgggaaaat     180
gggacgacgt gtctcatggc agagtttgca gccaaattta ttgtacctta tgatgtgtgg     240
gccagcaact acgtagatct gatcacagaa caggccgata tcgcattgac ccggggagct     300
gaggtgaagg gccgctgtgg ccacagccag tcggagctgc aagtgttctg ggtggatcgc     360
gcatatgcac tcaaaatgct ctttgtaaag gaaagccaca acatgtccaa gggacctgag     420
gcgacttgga ggctgagcaa agtgcagttt gtctacgact cctcggagaa aacccacttc     480
aaagacgcag tcagtgctgg gaagcacaca gccaactcgc accacctctc tgccttggtc     540
accccgctg ggaagtccta tgagtgtcaa gctcaacaaa ccatttcact ggcctctagt     600
gatccgcaga agacggtcac catgatcctg tctgcggtcc acatccaacc ttttgacatt     660
atctcagatt ttgtcttcag tgaagagcat aaatgcccag tggatgagcg ggagcaactg     720
gaagaaacct tgcccctgat tttggggctc atcttgggcc tcgtcatcat ggtaacactc     780
gcgatttacc acgtccacca caaaatgact gccaaccagg tgcagatccc tcgggacaga     840
tcccagtata agcacatggg ctag                                            864
```

<210> SEQ ID NO 15
<211> LENGTH: 287
<212> TYPE: PRT
<213> ORGANISM: Artificial Sequence
<220> FEATURE:
<223> OTHER INFORMATION: pMCN2_CD43ss_V5-LAMP5

<400> SEQUENCE: 15

Met Ala Ser Leu Leu Leu Leu Gly Val Leu Val Val Ser Pro Asp
1               5                   10                  15

Ala Leu Gly Val Asp Gly Gly Lys Pro Ile Pro Asn Pro Leu Leu Gly
            20                  25                  30

Leu Asp Ser Thr Glu Gln Glu Val Glu Asn Leu Ser Gly Leu Ser Thr
        35                  40                  45

Asn Pro Glu Lys Asp Ile Phe Val Val Arg Glu Asn Gly Thr Thr Cys
    50                  55                  60

Leu Met Ala Glu Phe Ala Ala Lys Phe Ile Val Pro Tyr Asp Val Trp
65                  70                  75                  80

Ala Ser Asn Tyr Val Asp Leu Ile Thr Glu Gln Ala Asp Ile Ala Leu
                85                  90                  95

Thr Arg Gly Ala Glu Val Lys Gly Arg Cys Gly His Ser Gln Ser Glu
            100                 105                 110

Leu Gln Val Phe Trp Val Asp Arg Ala Tyr Ala Leu Lys Met Leu Phe
        115                 120                 125

Val Lys Glu Ser His Asn Met Ser Lys Gly Pro Glu Ala Thr Trp Arg
    130                 135                 140

Leu Ser Lys Val Gln Phe Val Tyr Asp Ser Ser Glu Lys Thr His Phe
145                 150                 155                 160

Lys Asp Ala Val Ser Ala Gly Lys His Thr Ala Asn Ser His His Leu
                165                 170                 175

Ser Ala Leu Val Thr Pro Ala Gly Lys Ser Tyr Glu Cys Gln Ala Gln
            180                 185                 190

Gln Thr Ile Ser Leu Ala Ser Ser Asp Pro Lys Thr Val Thr Met
        195                 200                 205

```
Ile Leu Ser Ala Val His Ile Gln Pro Phe Asp Ile Ser Asp Phe
    210                 215                 220
Val Phe Ser Glu Glu His Lys Cys Pro Val Asp Glu Arg Glu Gln Leu
225                 230                 235                 240
Glu Glu Thr Leu Pro Leu Ile Leu Gly Leu Ile Leu Gly Leu Val Ile
                245                 250                 255
Met Val Thr Leu Ala Ile Tyr His Val His His Lys Met Thr Ala Asn
                260                 265                 270
Gln Val Gln Ile Pro Arg Asp Arg Ser Gln Tyr Lys His Met Gly
                275                 280                 285

<210> SEQ ID NO 16
<211> LENGTH: 21
<212> TYPE: DNA
<213> ORGANISM: Artificial Sequence
<220> FEATURE:
<223> OTHER INFORMATION: mIgG_CH primer

<400> SEQUENCE: 16
gggccagtgg atagacagat g                                              21

<210> SEQ ID NO 17
<211> LENGTH: 24
<212> TYPE: DNA
<213> ORGANISM: Artificial Sequence
<220> FEATURE:
<223> OTHER INFORMATION: mIgG2b_CH primer

<400> SEQUENCE: 17 cagggggccag tggatagact gatg                                           24

<210> SEQ ID NO 18
<211> LENGTH: 23
<212> TYPE: DNA
<213> ORGANISM: Artificial Sequence
<220> FEATURE:
<223> OTHER INFORMATION: Mk_CL primer

<400> SEQUENCE: 18
gctcactgga tggtgggaag atg                                            23

<210> SEQ ID NO 19
<211> LENGTH: 354
<212> TYPE: DNA
<213> ORGANISM: Mus musculus

<400> SEQUENCE: 19
gagatccagc tgcagcagtc tggacctgac ctggtgaagc ctggggcttc agtgaaggta      60
tcctgcaagg cttctggttt tgcattcagt acctacaaca tgtactgggt gaagcagagc     120
catggaaaga gccttgagtg gattggatat attgatcctt acaatggtga tattacctac     180
aaccagaagt tcaagggcaa ggccacattg actgttgaca gtcctccag cacagcctac      240
atgcatctca acagcctgac atctgaggac tctgcagtct attactgtgc aagaagggac     300
tacttttatg ctatggacta ctggggtcaa ggaacctcag tcaccgtctc ctca           354

<210> SEQ ID NO 20
<211> LENGTH: 118
<212> TYPE: PRT
<213> ORGANISM: Mus musculus

<400> SEQUENCE: 20
```

```
Glu Ile Gln Leu Gln Gln Ser Gly Pro Asp Leu Val Lys Pro Gly Ala
1               5                   10                  15

Ser Val Lys Val Ser Cys Lys Ala Ser Gly Phe Ala Phe Ser Thr Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Asp Ile Thr Tyr Asn Gln Lys Phe
    50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Arg Asp Tyr Phe Tyr Ala Met Asp Tyr Trp Gly Gln Gly Thr
            100                 105                 110

Ser Val Thr Val Ser Ser
            115
```

<210> SEQ ID NO 21
<211> LENGTH: 321
<212> TYPE: DNA
<213> ORGANISM: Mus musculus

<400> SEQUENCE: 21

```
gacattgtga tgacccagtc tcacaaattc atgtccacat cagtaggaga cagggtcagc    60
atcacctgca aggccagtca gggtgtgggt actgctgtag cctggtatca acagaaacca   120
ggacaatctc ctaaactact gatttactgg gcatccaccc ggcacactgg agtccctgat   180
cgcttcacag gcagtggatc tgggacagat ttcactctct ccgttaccaa tgtgcagtct   240
gaagacttgg cagattattt ctgtcaccaa tatagcagct atcctctcac gttcggttct   300
gggaccaagc tggagctgaa a                                            321
```

<210> SEQ ID NO 22
<211> LENGTH: 107
<212> TYPE: PRT
<213> ORGANISM: Mus musculus

<400> SEQUENCE: 22

```
Asp Ile Val Met Thr Gln Ser His Lys Phe Met Ser Thr Ser Val Gly
1               5                   10                  15

Asp Arg Val Ser Ile Thr Cys Lys Ala Ser Gln Gly Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Ser Val Thr Asn Val Gln Ser
65                  70                  75                  80

Glu Asp Leu Ala Asp Tyr Phe Cys His Gln Tyr Ser Ser Tyr Pro Leu
                85                  90                  95

Thr Phe Gly Ser Gly Thr Lys Leu Glu Leu Lys
            100                 105
```

<210> SEQ ID NO 23
<211> LENGTH: 357
<212> TYPE: DNA
<213> ORGANISM: Mus musculus

<400> SEQUENCE: 23

```
gaagtgaagc ttgaggagtc tggaggaggc ttggtgcaac ctggaggatc catgaaactc    60
tcttgtactg cctctggatt cactttcagt gacgcctgga tggactgggt ccgccagtct   120
ccagagaagg ggcttgagtg ggtcgctgaa attagaggca aagctgataa tcatgcaacc   180
tattatgctg agtctgtgaa ggggagattc accatttcaa gagatgattc aaaagtagt   240
gtctacctgc aaatgaacag tttgagaact gaagacactg ccatttatta ctgtatccct   300
tattatcggt atgctatgga ctactggggt caaggaacct cagtcaccgt ctcctca      357
```

<210> SEQ ID NO 24
<211> LENGTH: 119
<212> TYPE: PRT
<213> ORGANISM: Mus musculus

<400> SEQUENCE: 24

Glu Val Lys Leu Glu Glu Ser Gly Gly Gly Leu Val Gln Pro Gly Gly
1               5                   10                  15
Ser Met Lys Leu Ser Cys Thr Ala Ser Gly Phe Thr Phe Ser Asp Ala
            20                  25                  30
Trp Met Asp Trp Val Arg Gln Ser Pro Glu Lys Gly Leu Glu Trp Val
        35                  40                  45
Ala Glu Ile Arg Gly Lys Ala Asp Asn His Ala Thr Tyr Tyr Ala Glu
    50                  55                  60
Ser Val Lys Gly Arg Phe Thr Ile Ser Arg Asp Asp Ser Lys Ser Ser
65                  70                  75                  80
Val Tyr Leu Gln Met Asn Ser Leu Arg Thr Glu Asp Thr Ala Ile Tyr
                85                  90                  95
Tyr Cys Ile Pro Tyr Tyr Arg Tyr Ala Met Asp Tyr Trp Gly Gln Gly
            100                 105                 110
Thr Ser Val Thr Val Ser Ser
        115

<210> SEQ ID NO 25
<211> LENGTH: 318
<212> TYPE: DNA
<213> ORGANISM: Mus musculus

<400> SEQUENCE: 25

```
caaattgttc tcacccagtc tccagcaatc atgtctgcat ctccagggga gaaagtcacc    60
ataacctgca ctgccagttc aagtgtcagt tacatgcact ggttccagca gaagccaggc   120
acttctccca aactctggat ttatgccact tcctacctgg cttctggagt ccctactcgc   180
ttcagtggca gtggatctgg gacctcttac tctctcacaa tcagccgaat ggaggctgaa   240
gatgctgcca cttattactg ccagcaaaag agtaattacc cgtggacgtt cggtggaggc   300
accaacctgg aaatcaag                                                 318
```

<210> SEQ ID NO 26
<211> LENGTH: 106
<212> TYPE: PRT
<213> ORGANISM: Mus musculus

<400> SEQUENCE: 26

Gln Ile Val Leu Thr Gln Ser Pro Ala Ile Met Ser Ala Ser Pro Gly
1               5                   10                  15
Glu Lys Val Thr Ile Thr Cys Thr Ala Ser Ser Ser Val Ser Tyr Met
            20                  25                  30

```
His Trp Phe Gln Gln Lys Pro Gly Thr Ser Pro Lys Leu Trp Ile Tyr
         35                  40                  45

Ala Thr Ser Tyr Leu Ala Ser Gly Val Pro Thr Arg Phe Ser Gly Ser
     50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Lys Ser Asn Tyr Pro Trp Thr
                 85                  90                  95

Phe Gly Gly Gly Thr Asn Leu Glu Ile Lys
            100                 105
```

<210> SEQ ID NO 27
<211> LENGTH: 348
<212> TYPE: DNA
<213> ORGANISM: Mus musculus

<400> SEQUENCE: 27

```
gaagtgaagc tggtggagtc tgggggaggc ttagtgaagc ctggagggtc cctgaaactc      60
tcctgtgcag cctctggatt cactttcagt agctatgcca tgtcttgggt tcgccagact     120
ccagagaaga ggctggagtg ggtcgcatcc attagtagtg gtggtagcac ctactatcca     180
gacagtgtga aggccgatt caccatctcc agagataatg ccaggaacat cctgtacctg      240
caaatgagca gtctgaggtc tgaggacacg gccatgtatt actgtgcaag gttgattacg     300
acgaggtttg cttactgggg ccaagggact ctggtcactg tctctgca                  348
```

<210> SEQ ID NO 28
<211> LENGTH: 116
<212> TYPE: PRT
<213> ORGANISM: Mus musculus

<400> SEQUENCE: 28

```
Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
             20                  25                  30

Ala Met Ser Trp Val Arg Gln Thr Pro Glu Lys Arg Leu Glu Trp Val
         35                  40                  45

Ala Ser Ile Ser Ser Gly Gly Ser Thr Tyr Tyr Pro Asp Ser Val Lys
     50                  55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Met Tyr Tyr Cys Ala
                 85                  90                  95

Arg Leu Ile Thr Thr Arg Phe Ala Tyr Trp Gly Gln Gly Thr Leu Val
            100                 105                 110

Thr Val Ser Ala
        115
```

<210> SEQ ID NO 29
<211> LENGTH: 324
<212> TYPE: DNA
<213> ORGANISM: Mus musculus

<400> SEQUENCE: 29

```
gaaaatgtgc tcacccagtc tccagcaatc atgtctgcat ctccagggga aaaggtcacc      60
atgacctgca gggccagctc aagtgtaagt tccagttact tgcactggta ccagcagaag     120
```

```
tcaggtgcct cccccaaact ctggatttat agcacatcca acttggcttc tggagtccct    180
gctcgcttca gtggcagtgg gtctgggacc tcttactctc tcacaatcag cagtgtggag    240
gctgaagatg ctgccactta ttactgccag cagtacagtg gttacccact cacgttcggc    300
tcggggacaa agttggaaat aaaa                                           324
```

<210> SEQ ID NO 30
<211> LENGTH: 108
<212> TYPE: PRT
<213> ORGANISM: Mus musculus

<400> SEQUENCE: 30

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ser Gly Thr Lys Leu Glu Ile Lys
            100                 105
```

<210> SEQ ID NO 31
<211> LENGTH: 354
<212> TYPE: DNA
<213> ORGANISM: Mus musculus

<400> SEQUENCE: 31

```
gagatccagc tgcagcagtc tggacctgag ctggtgaagc ctggggcttc agtgaaggta    60
tcctgcaagg cttctggtta tgcattcact agctacaaca tgtactgggt gaagcagagc    120
catggaaaga gccttgagtg gattggatat attgatcctt acaatggtgg tattagctac    180
aaccagaagt tcaagggcaa ggccacattg actgttgaca gtcctccag cacagcctac    240 atgcatctca acagcctgac atctgaggac tctgcagtct attactgtgc aagaagggac    300 tactttatg ctatggacta ctggggtcaa ggaacctcag tcaccgtctc ctca           354
```

<210> SEQ ID NO 32
<211> LENGTH: 118
<212> TYPE: PRT
<213> ORGANISM: Mus musculus

<400> SEQUENCE: 32

```
Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Ile Ser Tyr Asn Gln Lys Phe
    50                  55                  60

Lys Gly Lys Ala Thr Leu Thr Val Asp Lys Ser Ser Ser Thr Ala Tyr
```

```
                65                  70                  75                  80
Met His Leu Asn Ser Leu Thr Ser Glu Asp Ser Ala Val Tyr Tyr Cys
                            85                  90                  95

Ala Arg Arg Asp Tyr Phe Tyr Ala Met Asp Tyr Trp Gly Gln Gly Thr
                100                 105                 110

Ser Val Thr Val Ser Ser
            115
```

<210> SEQ ID NO 33
<211> LENGTH: 321
<212> TYPE: DNA
<213> ORGANISM: Mus musculus

<400> SEQUENCE: 33

```
gacattgtga tgacccagtc tcacaaattc atgtccacat cagtaggaga cagggtcagc      60
atcacctgca aggccagtca gggtgtgggt actgctgtag cctggtatca acagaaacca     120
gggcaatctc ctaaactact gatttactgg gcatccaccc ggcacactgg agtccctgat     180
cgcttcacag gcagtggatc tgggacagat ttcactctca ccattaccaa tgtgcagtct     240
gaagacttgg cagattattt ctgtcagcaa tatagcagct atcctctcac gttcggttct     300
gggaccaagc tggagctgaa a                                                321
```

<210> SEQ ID NO 34
<211> LENGTH: 107
<212> TYPE: PRT
<213> ORGANISM: Mus musculus

<400> SEQUENCE: 34

```
Asp Ile Val Met Thr Gln Ser His Lys Phe Met Ser Thr Ser Val Gly
1               5                   10                  15

Asp Arg Val Ser Ile Thr Cys Lys Ala Ser Gln Gly Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ser Gly Thr Lys Leu Glu Leu Lys
            100                 105
```

<210> SEQ ID NO 35
<211> LENGTH: 5
<212> TYPE: PRT
<213> ORGANISM: Mus musculus

<400> SEQUENCE: 35

```
Thr Tyr Asn Met Tyr
1               5
```

<210> SEQ ID NO 36
<211> LENGTH: 17
<212> TYPE: PRT
<213> ORGANISM: Mus musculus

<400> SEQUENCE: 36

```
Tyr Ile Asp Pro Tyr Asn Gly Asp Ile Thr Tyr Asn Gln Lys Phe Lys
1               5                   10                  15
Gly

<210> SEQ ID NO 37
<211> LENGTH: 9
<212> TYPE: PRT
<213> ORGANISM: Mus musculus

<400> SEQUENCE: 37

Arg Asp Tyr Phe Tyr Ala Met Asp Tyr
1               5

<210> SEQ ID NO 38
<211> LENGTH: 11
<212> TYPE: PRT
<213> ORGANISM: Mus musculus

<400> SEQUENCE: 38

Lys Ala Ser Gln Gly Val Gly Thr Ala Val Ala
1               5                   10

<210> SEQ ID NO 39
<211> LENGTH: 7
<212> TYPE: PRT
<213> ORGANISM: Mus musculus

<400> SEQUENCE: 39

Trp Ala Ser Thr Arg His Thr
1               5

<210> SEQ ID NO 40
<211> LENGTH: 9
<212> TYPE: PRT
<213> ORGANISM: Mus musculus

<400> SEQUENCE: 40

His Gln Tyr Ser Ser Tyr Pro Leu Thr
1               5

<210> SEQ ID NO 41
<211> LENGTH: 5
<212> TYPE: PRT
<213> ORGANISM: Mus musculus

<400> SEQUENCE: 41

Asp Ala Trp Met Asp
1               5

<210> SEQ ID NO 42
<211> LENGTH: 17
<212> TYPE: PRT
<213> ORGANISM: Mus musculus

<400> SEQUENCE: 42

Glu Ile Arg Gly Lys Ala Asp Asn His Ala Thr Tyr Tyr Ala Glu Ser
1               5                   10                  15
Val

<210> SEQ ID NO 43
<211> LENGTH: 8
<212> TYPE: PRT
<213> ORGANISM: Mus musculus
```

```
<400> SEQUENCE: 43

Tyr Tyr Arg Tyr Ala Met Asp Tyr
1               5

<210> SEQ ID NO 44
<211> LENGTH: 10
<212> TYPE: PRT
<213> ORGANISM: Mus musculus

<400> SEQUENCE: 44

Thr Ala Ser Ser Ser Val Ser Tyr Met His
1               5                   10

<210> SEQ ID NO 45
<211> LENGTH: 7
<212> TYPE: PRT
<213> ORGANISM: Mus musculus

<400> SEQUENCE: 45

Ala Thr Ser Tyr Leu Ala Ser
1               5

<210> SEQ ID NO 46
<211> LENGTH: 9
<212> TYPE: PRT
<213> ORGANISM: Mus musculus

<400> SEQUENCE: 46

Gln Gln Lys Ser Asn Tyr Pro Trp Thr
1               5

<210> SEQ ID NO 47
<211> LENGTH: 5
<212> TYPE: PRT
<213> ORGANISM: Mus musculus

<400> SEQUENCE: 47

Ser Tyr Ala Met Ser
1               5

<210> SEQ ID NO 48
<211> LENGTH: 14
<212> TYPE: PRT
<213> ORGANISM: Mus musculus

<400> SEQUENCE: 48

Ser Ile Ser Ser Gly Gly Ser Thr Tyr Tyr Pro Asp Ser Val
1               5                   10

<210> SEQ ID NO 49
<211> LENGTH: 8
<212> TYPE: PRT
<213> ORGANISM: Mus musculus

<400> SEQUENCE: 49

Leu Ile Thr Thr Arg Phe Ala Tyr
1               5

<210> SEQ ID NO 50
<211> LENGTH: 12
<212> TYPE: PRT
<213> ORGANISM: Mus musculus

<400> SEQUENCE: 50
```

```
Arg Ala Ser Ser Ser Val Ser Ser Ser Tyr Leu His
1               5                   10

<210> SEQ ID NO 51
<211> LENGTH: 7
<212> TYPE: PRT
<213> ORGANISM: Mus musculus

<400> SEQUENCE: 51

Ser Thr Ser Asn Leu Ala Ser
1               5

<210> SEQ ID NO 52
<211> LENGTH: 9
<212> TYPE: PRT
<213> ORGANISM: Mus musculus

<400> SEQUENCE: 52

Gln Gln Tyr Ser Gly Tyr Pro Leu Thr
1               5

<210> SEQ ID NO 53
<211> LENGTH: 5
<212> TYPE: PRT
<213> ORGANISM: Mus musculus

<400> SEQUENCE: 53

Ser Tyr Asn Met Tyr
1               5

<210> SEQ ID NO 54
<211> LENGTH: 17
<212> TYPE: PRT
<213> ORGANISM: Mus musculus

<400> SEQUENCE: 54

Tyr Ile Asp Pro Tyr Asn Gly Gly Ile Ser Tyr Asn Gln Lys Phe Lys
1               5                   10                  15

Gly

<210> SEQ ID NO 55
<211> LENGTH: 9
<212> TYPE: PRT
<213> ORGANISM: Mus musculus

<400> SEQUENCE: 55

Arg Asp Tyr Phe Tyr Ala Met Asp Tyr
1               5

<210> SEQ ID NO 56
<211> LENGTH: 11
<212> TYPE: PRT
<213> ORGANISM: Mus musculus

<400> SEQUENCE: 56

Lys Ala Ser Gln Gly Val Gly Thr Ala Val Ala
1               5                   10

<210> SEQ ID NO 57
<211> LENGTH: 7
<212> TYPE: PRT
<213> ORGANISM: Mus musculus

<400> SEQUENCE: 57
```

```
<210> SEQ ID NO 58
<211> LENGTH: 9
<212> TYPE: PRT
<213> ORGANISM: Mus musculus

<400> SEQUENCE: 58

Gln Gln Tyr Ser Ser Tyr Pro Leu Thr
1               5

<210> SEQ ID NO 59
<211> LENGTH: 25
<212> TYPE: DNA
<213> ORGANISM: Artificial Sequence
<220> FEATURE:
<223> OTHER INFORMATION: mLAMP5-F

<400> SEQUENCE: 59
atggatctcc gagtaagaac ccttc                                              25

<210> SEQ ID NO 60
<211> LENGTH: 26
<212> TYPE: DNA
<213> ORGANISM: Artificial Sequence
<220> FEATURE:
<223> OTHER INFORMATION: mLAMP5-R

<400> SEQUENCE: 60
ctagcccatg tgcttgtact gggaac                                             26

<210> SEQ ID NO 61
<211> LENGTH: 78
<212> TYPE: DNA
<213> ORGANISM: Artificial Sequence
<220> FEATURE:
<223> OTHER INFORMATION: SalI-G-V5-mLAMP5-F

<400> SEQUENCE: 61
taagtcgacg gtggtaagcc tatccctaac cctctcctcg gtctcgattc tacggaacaa        60
gaagtggaaa atctttcg                                                      78

<210> SEQ ID NO 62
<211> LENGTH: 35
<212> TYPE: DNA
<213> ORGANISM: Artificial Sequence
<220> FEATURE:
<223> OTHER INFORMATION: mLAMP5-NotI-R

<400> SEQUENCE: 62
aatgcggccg cctagcccat gtgcttgtac tggga                                   35

<210> SEQ ID NO 63
<211> LENGTH: 864
<212> TYPE: DNA
<213> ORGANISM: Artificial Sequence
<220> FEATURE:
<223> OTHER INFORMATION: pMCN2_CD43ss_V5-mLAMP5

<400> SEQUENCE: 63
atggctagcc ttctccttct ccttggggtg ctggtggtaa gcccagacgc tctggggtc         60 gacggtggta agcctatccc taaccctctc ctcggtctcg attctacgga acaagaagtg       120
gaaaatcttt cgggcctttc cacgaacccc gagaaagaca tatttgtggt gcgggaaaat      180
```

```
gggacgacgt gtctcatggc agagtttgca gccaaattta ttgtacctta tgatgtgtgg    240
gccagcaatt atgtggatct gatcacagaa caggctgaga tctccttgac ccggggagct    300
gaggtgaagg ccactgtgg ccacaacgag tcggagctgg aggtgttctg ggtagatcac     360
gcctacacac tcagaatgct ctttgtaaag gaaagtcaca acacttccaa aggaccagag    420
gcgacttgga atctgaacaa ggtgcatttt gtctatgatt cctcggagaa gactcacttt    480
aaagcccctg tgaaggttaa taagtacatc gccagctctc atcacctctc tgccttggtc    540
accccagctg ggatgtccta tgagtgtcag gctcagcaga ccatttctct ggcctccagt    600
gaccctcaga agactgtcac catgatcctg tccgcagtgc atccagcc ctttgatatc      660 atctctgact ttgtcttcag tgaagaacat aaatgtccag tggatgagca agagcagttg    720
gaagagaccc tgcccctgat cctgggcctc atcttgggcc ttgtcattgt cataacactt    780
gtgatctacc acatccacca taaaatgact gccaatcaag tgcagatccc cagggaccgt    840
tcccagtaca agcacatggg ctag                                           864

<210> SEQ ID NO 64
<211> LENGTH: 287
<212> TYPE: PRT
<213> ORGANISM: Artificial Sequence
<220> FEATURE:
<223> OTHER INFORMATION: pMCN2_CD43ss_V5-mLAMP5

<400> SEQUENCE: 64

Met Ala Ser Leu Leu Leu Leu Gly Val Leu Val Val Ser Pro Asp
1               5                   10                  15

Ala Leu Gly Val Asp Gly Gly Lys Pro Ile Pro Asn Pro Leu Leu Gly
            20                  25                  30

Leu Asp Ser Thr Glu Gln Glu Val Glu Asn Leu Ser Gly Leu Ser Thr
        35                  40                  45

Asn Pro Glu Lys Asp Ile Phe Val Val Arg Glu Asn Gly Thr Thr Cys
    50                  55                  60

Leu Met Ala Glu Phe Ala Ala Lys Phe Ile Val Pro Tyr Asp Val Trp
65                  70                  75                  80

Ala Ser Asn Tyr Val Asp Leu Ile Thr Glu Gln Ala Glu Ile Ser Leu
                85                  90                  95

Thr Arg Gly Ala Glu Val Lys Gly His Cys Gly His Asn Glu Ser Glu
            100                 105                 110

Leu Glu Val Phe Trp Val Asp His Ala Tyr Thr Leu Arg Met Leu Phe
        115                 120                 125

Val Lys Glu Ser His Asn Thr Ser Lys Gly Pro Glu Ala Thr Trp Asn
    130                 135                 140

Leu Asn Lys Val His Phe Val Tyr Asp Ser Ser Glu Lys Thr His Phe
145                 150                 155                 160

Lys Ala Pro Val Lys Val Asn Lys Tyr Ile Ala Ser Ser His His Leu
                165                 170                 175

Ser Ala Leu Val Thr Pro Ala Gly Met Ser Tyr Glu Cys Gln Ala Gln
            180                 185                 190

Gln Thr Ile Ser Leu Ala Ser Ser Asp Pro Lys Thr Val Thr Met
        195                 200                 205

Ile Leu Ser Ala Val His Ile Gln Pro Phe Asp Ile Ile Ser Asp Phe
    210                 215                 220

Val Phe Ser Glu Glu His Lys Cys Pro Val Asp Glu Gln Glu Gln Leu
225                 230                 235                 240
```

```
Glu Glu Thr Leu Pro Leu Ile Leu Gly Leu Ile Leu Gly Leu Val Ile
                245                 250                 255

Val Ile Thr Leu Val Ile Tyr His Ile His His Lys Met Thr Ala Asn
            260                 265                 270

Gln Val Gln Ile Pro Arg Asp Arg Ser Gln Tyr Lys His Met Gly
        275                 280                 285

<210> SEQ ID NO 65
<211> LENGTH: 280
<212> TYPE: PRT
<213> ORGANISM: Homo sapiens

<400> SEQUENCE: 65

Met Asp Leu Gln Gly Arg Gly Val Pro Ser Ile Asp Arg Leu Arg Val
1               5                   10                  15

Leu Leu Met Leu Phe His Thr Met Ala Gln Ile Met Ala Glu Gln Glu
            20                  25                  30

Val Glu Asn Leu Ser Gly Leu Ser Thr Asn Pro Glu Lys Asp Ile Phe
        35                  40                  45

Val Val Arg Glu Asn Gly Thr Thr Cys Leu Met Ala Glu Phe Ala Ala
    50                  55                  60

Lys Phe Ile Val Pro Tyr Asp Val Trp Ala Ser Asn Tyr Val Asp Leu
65                  70                  75                  80

Ile Thr Glu Gln Ala Asp Ile Ala Leu Thr Arg Gly Ala Glu Val Lys
                85                  90                  95

Gly Arg Cys Gly His Ser Gln Ser Glu Leu Gln Val Phe Trp Val Asp
            100                 105                 110

Arg Ala Tyr Ala Leu Lys Met Leu Phe Val Lys Glu Ser His Asn Met
        115                 120                 125

Ser Lys Gly Pro Glu Ala Thr Trp Arg Leu Ser Lys Val Gln Phe Val
    130                 135                 140

Tyr Asp Ser Ser Glu Lys Thr His Phe Lys Asp Ala Val Ser Ala Gly
145                 150                 155                 160

Lys His Thr Ala Asn Ser His His Leu Ser Ala Leu Val Thr Pro Ala
                165                 170                 175

Gly Lys Ser Tyr Glu Cys Gln Ala Gln Gln Thr Ile Ser Leu Ala Ser
            180                 185                 190

Ser Asp Pro Gln Lys Thr Val Thr Met Ile Leu Ser Ala Val His Ile
        195                 200                 205

Gln Pro Phe Asp Ile Ile Ser Asp Phe Val Phe Ser Glu Glu His Lys
    210                 215                 220

Cys Pro Val Asp Glu Arg Glu Gln Leu Glu Glu Thr Leu Pro Leu Ile
225                 230                 235                 240

Leu Gly Leu Ile Leu Gly Leu Val Ile Met Val Thr Leu Ala Ile Tyr
                245                 250                 255

His Val His His Lys Met Thr Ala Asn Gln Val Gln Ile Pro Arg Asp
            260                 265                 270

Arg Ser Gln Tyr Lys His Met Gly
        275                 280

<210> SEQ ID NO 66
<211> LENGTH: 843
<212> TYPE: DNA
<213> ORGANISM: Homo sapiens

<400> SEQUENCE: 66
```

```
atggatctcc aaggaagagg ggtccccagc atcgacagac ttcgagttct cctgatgttg    60
ttccatacaa tggctcaaat catggcagaa caagaagtgg aaaatctctc aggcctttcc   120
actaaccctg aaaaagatat atttgtggtg cgggaaaatg ggacgacgtg tctcatggca   180
gagtttgcag ccaaatttat tgtacccttat gatgtgtggg ccagcaacta cgtagatctg   240
atcacagaac aggccgatat cgcattgacc cggggagctg aggtgaaggg ccgctgtggc   300
cacagccagt cggagctgca agtgttctgg gtggatcgcg catatgcact caaaatgctc   360
tttgtaaagg aaagccacaa catgtccaag ggacctgagg cgacttggag gctgagcaaa   420
gtgcagtttg tctacgactc ctcggagaaa acccacttca agacgcagt cagtgctggg   480
aagcacacag ccaactcgca ccacctctct gccttggtca cccccgctgg aagtcctat   540
gagtgtcaag ctcaacaaac catttcactg gcctctagtg atccgcagaa acggtcacc   600
atgatcctgt ctgcggtcca catccaacct tttgacatta tctcagattt tgtcttcagt   660
gaagagcata atgcccagt ggatgagcgg gagcaactgg aagaaacctt gcccctgatt   720
ttggggctca tcttgggcct cgtcatcatg gtaacactcg cgatttacca cgtccaccac   780
aaaatgactg ccaaccaggt gcagatccct cgggacagat cccagtataa gcacatgggc   840
tag                                                                  843

<210> SEQ ID NO 67
<211> LENGTH: 183
<212> TYPE: PRT
<213> ORGANISM: Homo sapiens

<400> SEQUENCE: 67

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180

<210> SEQ ID NO 68
<211> LENGTH: 330
<212> TYPE: PRT
```

<213> ORGANISM: Artificial Sequence
<220> FEATURE:
<223> OTHER INFORMATION: human IgG1(AAC82527.1) to which an alanine is
      added N-terminally

<400> SEQUENCE: 68

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 69
<211> LENGTH: 326
<212> TYPE: PRT
<213> ORGANISM: Artificial Sequence
<220> FEATURE:
<223> OTHER INFORMATION: human IgG2(AAB59393.1) to which an alanine is
      added N-terminally

<400> SEQUENCE: 69

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 70
<211> LENGTH: 377
<212> TYPE: PRT
<213> ORGANISM: Homo sapiens

<400> SEQUENCE: 70

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 71
<211> LENGTH: 327
<212> TYPE: PRT
<213> ORGANISM: Artificial Sequence
<220> FEATURE:
<223> OTHER INFORMATION: human IgG4(AAB59394.1) to which an alanine is
      added N-terminally

<400> SEQUENCE: 71

Ala Ser Thr Lys Gly Pro Ser Val Phe Pro Leu Ala Pro Cys Ser Arg
1               5                   10                  15

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 72
<211> LENGTH: 105
<212> TYPE: PRT
<213> ORGANISM: Homo sapiens

<400> SEQUENCE: 72

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
```

```
                50                  55                  60
Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
                100                 105

<210> SEQ ID NO 73
<211> LENGTH: 107
<212> TYPE: PRT
<213> ORGANISM: Homo sapiens

<400> SEQUENCE: 73

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 74
<211> LENGTH: 4
<212> TYPE: PRT
<213> ORGANISM: Artificial Sequence
<220> FEATURE:
<223> OTHER INFORMATION: linker

<400> SEQUENCE: 74

Gly Gly Gly Ser
  1

<210> SEQ ID NO 75
<211> LENGTH: 4
<212> TYPE: PRT
<213> ORGANISM: Artificial Sequence
<220> FEATURE:
<223> OTHER INFORMATION: linker

<400> SEQUENCE: 75

Ser Gly Gly Gly
  1

<210> SEQ ID NO 76
<211> LENGTH: 5
<212> TYPE: PRT
<213> ORGANISM: Artificial Sequence
<220> FEATURE:
<223> OTHER INFORMATION: linker

<400> SEQUENCE: 76

Gly Gly Gly Gly Ser
  1               5
```

<210> SEQ ID NO 77
<211> LENGTH: 5
<212> TYPE: PRT
<213> ORGANISM: Artificial Sequence
<220> FEATURE:
<223> OTHER INFORMATION: linker

<400> SEQUENCE: 77

Ser Gly Gly Gly Gly
1               5

<210> SEQ ID NO 78
<211> LENGTH: 6
<212> TYPE: PRT
<213> ORGANISM: Artificial Sequence
<220> FEATURE:
<223> OTHER INFORMATION: linker

<400> SEQUENCE: 78

Gly Gly Gly Gly Gly Ser
1               5

<210> SEQ ID NO 79
<211> LENGTH: 6
<212> TYPE: PRT
<213> ORGANISM: Artificial Sequence
<220> FEATURE:
<223> OTHER INFORMATION: linker

<400> SEQUENCE: 79

Ser Gly Gly Gly Gly Gly
1               5

<210> SEQ ID NO 80
<211> LENGTH: 7
<212> TYPE: PRT
<213> ORGANISM: Artificial Sequence
<220> FEATURE:
<223> OTHER INFORMATION: linker

<400> SEQUENCE: 80

Gly Gly Gly Gly Gly Gly Ser
1               5

<210> SEQ ID NO 81
<211> LENGTH: 7
<212> TYPE: PRT
<213> ORGANISM: Artificial Sequence
<220> FEATURE:
<223> OTHER INFORMATION: linker

<400> SEQUENCE: 81

Ser Gly Gly Gly Gly Gly Gly
1               5

<210> SEQ ID NO 82
<211> LENGTH: 9
<212> TYPE: PRT
<213> ORGANISM: Artificial Sequence
<220> FEATURE:
<223> OTHER INFORMATION: HA tag sequence

<400> SEQUENCE: 82

Tyr Pro Tyr Asp Val Pro Asp Tyr Ala
1               5

```
<210> SEQ ID NO 83
<211> LENGTH: 14
<212> TYPE: PRT
<213> ORGANISM: Artificial Sequence
<220> FEATURE:
<223> OTHER INFORMATION: V5 tag

<400> SEQUENCE: 83

Gly Lys Pro Ile Pro Asn Pro Leu Leu Gly Leu Asp Ser Thr
1               5                   10

<210> SEQ ID NO 84
<211> LENGTH: 19
<212> TYPE: PRT
<213> ORGANISM: Artificial Sequence
<220> FEATURE:
<223> OTHER INFORMATION: CD43 signal sequence

<400> SEQUENCE: 84

Met Ala Ser Leu Leu Leu Leu Leu Gly Val Leu Val Val Ser Pro Asp
1               5                   10                  15

Ala Leu Gly
```